(12) United States Patent
Steinberg et al.

(10) Patent No.: US 12,297,466 B2
(45) Date of Patent: *May 13, 2025

(54) ENGINEERED CAS9 NUCLEASES

(71) Applicant: Editas Medicine, Inc., Cambridge, MA (US)

(72) Inventors: Barrett Ethan Steinberg, Somerville, MA (US); Derek Cerchione, Cambridge, MA (US)

(73) Assignee: Editas Medicine, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/375,462

(22) Filed: Jul. 14, 2021

(65) Prior Publication Data

US 2022/0177861 A1 Jun. 9, 2022

Related U.S. Application Data

(60) Continuation of application No. 16/544,452, filed on Aug. 19, 2019, now Pat. No. 11,098,297, which is a division of application No. 16/003,967, filed on Jun. 8, 2018, now Pat. No. 10,428,319.

(60) Provisional application No. 62/665,388, filed on May 1, 2018, provisional application No. 62/517,811, filed on Jun. 9, 2017.

(51) Int. Cl.
| | |
|---|---|
| *C12N 9/22* | (2006.01) |
| *C12N 1/21* | (2006.01) |
| *C12N 15/10* | (2006.01) |
| *C12N 15/11* | (2006.01) |

(52) U.S. Cl.
CPC .............. *C12N 9/22* (2013.01); *C12N 15/102* (2013.01); *C12N 15/11* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 7,476,500 B1 | 1/2009 | Liu et al. |
| 8,546,553 B2 | 10/2013 | Terns et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,023,649 B2 | 5/2015 | Mali et al. |
| 9,074,199 B1 | 7/2015 | Chavez et al. |
| 9,234,213 B2 | 1/2016 | Wu |
| 9,260,723 B2 | 2/2016 | Mali et al. |
| 9,260,752 B1 | 2/2016 | May et al. |
| 9,267,135 B2 | 2/2016 | Church et al. |
| 9,322,037 B2 | 4/2016 | Liu et al. |
| 9,388,430 B2 | 7/2016 | Liu et al. |
| 9,404,098 B2 | 8/2016 | Terns et al. |
| 9,410,198 B2 | 8/2016 | May et al. |
| 9,422,553 B2 | 8/2016 | Terns et al. |
| 9,512,446 B1 | 12/2016 | Joung et al. |
| 9,567,603 B2 | 2/2017 | Joung et al. |
| 9,567,604 B2 | 2/2017 | Joung et al. |
| 9,587,252 B2 | 3/2017 | Church et al. |
| 9,637,739 B2 | 5/2017 | Siksnys et al. |
| 9,663,782 B2 | 5/2017 | Yu et al. |
| 9,688,971 B2 | 6/2017 | Doudna et al. |
| 9,725,714 B2 | 8/2017 | May et al. |
| 9,738,908 B2 | 8/2017 | Wu |
| 9,752,132 B2 | 9/2017 | Joung et al. |
| 9,790,490 B2 | 10/2017 | Zhang et al. |
| 9,803,194 B2 | 10/2017 | May et al. |
| 9,809,814 B1 | 11/2017 | May et al. |
| 9,822,370 B2 | 11/2017 | Musunuru et al. |
| 9,822,372 B2 | 11/2017 | Zhang et al. |
| 9,840,713 B2 | 12/2017 | Zhang |
| 9,873,894 B2 | 1/2018 | Conway et al. |
| 9,879,269 B2 | 1/2018 | Barrangou et al. |
| 9,885,026 B2 | 2/2018 | Brouns et al. |
| 9,902,974 B2 | 2/2018 | Conway et al. |
| 9,909,122 B2 | 3/2018 | May et al. |

(Continued)

FOREIGN PATENT DOCUMENTS

| | | |
|---|---|---|
| KR | 10-2015-0016588 A | 2/2015 |
| KR | 102350405 B1 | 1/2022 |

(Continued)

OTHER PUBLICATIONS

Liang et al., Rapid and highly efficient mammalian cell engineering viaCas9 protein transfection, J. Biotechnol. 208, 2015, 44-53. (Year: 2015).*

Uniprot, Accession No. Q99ZW2, 2016, www.uniprot.org. (Year: 2016).*

Cho et al., Targeted genome engineering in human cells with the Cas9 RNArna-guided endonuclease, Nature Biotechnol. 31, 2013, 230-32. (Year: 2013).*

Kleinstiver et al., High-fidelity CRISPR-Cas9 nucleases with no detectable genome-wide off-target effects, Nature 529, 2016, 490-94 (Year: 2016).*

(Continued)

*Primary Examiner* — Todd M Epstein
(74) *Attorney, Agent, or Firm* — Choate, Hall & Stewart LLP; Rolando Medina; Meaghan E. Bychowski

(57) ABSTRACT

The present disclosure relates to Cas9 nuclease variants and methods of producing and using such variants.

6 Claims, 23 Drawing Sheets

Specification includes a Sequence Listing.

(56) References Cited

U.S. PATENT DOCUMENTS

| | | | |
|---|---|---|---|
| 9,926,545 B2 | 3/2018 | Joung et al. |
| 9,926,546 B2 | 3/2018 | Joung et al. |
| 9,944,912 B2 | 4/2018 | Joung et al. |
| 9,963,689 B2 | 5/2018 | Doudna et al. |
| 9,970,001 B2 | 5/2018 | Miller |
| 9,970,024 B2 | 5/2018 | Church et al. |
| 10,066,233 B2 | 9/2018 | Barrangou et al. |
| 10,077,453 B2 | 9/2018 | Liu et al. |
| 10,093,910 B2 | 10/2018 | Joung et al. |
| 10,100,291 B2 | 10/2018 | Chavez et al. |
| 10,113,167 B2 | 10/2018 | Doudna et al. |
| 10,113,179 B2 | 10/2018 | Begemann et al. |
| 10,113,207 B2 | 10/2018 | Wang |
| 10,119,133 B2 | 11/2018 | Joung et al. |
| 10,125,361 B2 | 11/2018 | May et al. |
| 10,202,589 B2 | 2/2019 | Joung et al. |
| 10,202,619 B2 | 2/2019 | Wu |
| 10,227,611 B2 | 3/2019 | Doudna et al. |
| 10,266,850 B2 | 4/2019 | Doudna et al. |
| 10,301,651 B2 | 5/2019 | Doudna et al. |
| 10,308,961 B2 | 6/2019 | Doudna et al. |
| 10,329,587 B2 | 6/2019 | Church et al. |
| 10,351,878 B2 | 7/2019 | Doudna et al. |
| 10,358,658 B2 | 7/2019 | Doudna et al. |
| 10,358,659 B2 | 7/2019 | Doudna et al. |
| 10,377,998 B2 | 8/2019 | Zhang et al. |
| 10,378,027 B2 | 8/2019 | Joung et al. |
| 10,385,360 B2 | 8/2019 | Doudna et al. |
| 10,392,607 B2 | 8/2019 | Sternberg et al. |
| 10,400,253 B2 | 9/2019 | Doudna et al. |
| 10,407,697 B2 | 9/2019 | Doudna et al. |
| 10,415,059 B2 | 9/2019 | Joung et al. |
| 10,415,061 B2 | 9/2019 | Doudna et al. |
| 10,421,980 B2 | 9/2019 | Doudna et al. |
| 10,428,319 B2 | 10/2019 | Steinberg et al. |
| 10,428,352 B2 | 10/2019 | Doudna et al. |
| 10,435,679 B2 | 10/2019 | Chavez et al. |
| 10,435,708 B2 | 10/2019 | Mali et al. |
| 10,443,076 B2 | 10/2019 | Doudna et al. |
| 10,717,978 B2 | 7/2020 | Vakulskas et al. |
| 11,098,297 B2 | 8/2021 | Steinberg et al. |
| 2010/0076057 A1 | 3/2010 | Sontheimer et al. |
| 2010/0093617 A1 | 4/2010 | Barrangou et al. |
| 2013/0011828 A1 | 1/2013 | Barrangou et al. |
| 2013/0345064 A1 | 12/2013 | Liu et al. |
| 2014/0068797 A1 | 3/2014 | Doudna et al. |
| 2014/0093941 A1 | 4/2014 | Terns et al. |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0242664 A1 | 8/2014 | Zhang et al. |
| 2014/0242699 A1 | 8/2014 | Zhang |
| 2014/0256046 A1 | 9/2014 | Zhang et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273233 A1 | 9/2014 | Chen et al. |
| 2014/0287938 A1 | 9/2014 | Zhang et al. |
| 2014/0294773 A1 | 10/2014 | Brouns et al. |
| 2014/0302563 A1 | 10/2014 | Doudna et al. |
| 2014/0310830 A1 | 10/2014 | Zhang et al. |
| 2014/0315985 A1 | 10/2014 | May et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0356956 A1 | 12/2014 | Church et al. |
| 2014/0357523 A1 | 12/2014 | Zeiner et al. |
| 2014/0357530 A1 | 12/2014 | Zhang et al. |
| 2014/0377868 A1 | 12/2014 | Joung et al. |
| 2015/0020223 A1 | 1/2015 | Zhang et al. |
| 2015/0024499 A1 | 1/2015 | Brouns et al. |
| 2015/0024500 A1 | 1/2015 | Yu et al. |
| 2015/0031132 A1 | 1/2015 | Church et al. |
| 2015/0031133 A1 | 1/2015 | Church et al. |
| 2015/0031134 A1 | 1/2015 | Zhang et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056705 A1 | 2/2015 | Conway et al. |
| 2015/0071889 A1 | 3/2015 | Musunuru et al. |
| 2015/0071898 A1 | 3/2015 | Liu et al. |
| 2015/0071899 A1 | 3/2015 | Liu et al. |
| 2015/0079681 A1 | 3/2015 | Zhang |
| 2015/0176013 A1 | 6/2015 | Musunuru et al. |
| 2015/0184139 A1 | 7/2015 | Zhang et al. |
| 2015/0203872 A1 | 7/2015 | Zhang |
| 2015/0232833 A1 | 8/2015 | Mali et al. |
| 2015/0232882 A1 | 8/2015 | Zhang et al. |
| 2015/0240261 A1 | 8/2015 | Siksnys et al. |
| 2015/0247150 A1 | 9/2015 | Zhang et al. |
| 2015/0259684 A1 | 9/2015 | Church et al. |
| 2015/0259704 A1 | 9/2015 | Church et al. |
| 2015/0284727 A1 | 10/2015 | Kim et al. |
| 2015/0291961 A1 | 10/2015 | Siksnys et al. |
| 2015/0291965 A1 | 10/2015 | Zhang et al. |
| 2015/0291966 A1 | 10/2015 | Zhang et al. |
| 2015/0322457 A1 | 11/2015 | Kim et al. |
| 2015/0344912 A1 | 12/2015 | Kim et al. |
| 2015/0353905 A1 | 12/2015 | Weiss et al. |
| 2015/0353917 A1 | 12/2015 | Miller |
| 2015/0356239 A1 | 12/2015 | Zhang et al. |
| 2016/0002670 A1 | 1/2016 | Church et al. |
| 2016/0010076 A1 | 1/2016 | Joung et al. |
| 2016/0010154 A1 | 1/2016 | Laganiere et al. |
| 2016/0017366 A1 | 1/2016 | Chen et al. |
| 2016/0024523 A1 | 1/2016 | Joung et al. |
| 2016/0024524 A1 | 1/2016 | Joung et al. |
| 2016/0032274 A1 | 2/2016 | Church et al. |
| 2016/0046949 A1 | 2/2016 | May et al. |
| 2016/0046961 A1 | 2/2016 | Jinek et al. |
| 2016/0046962 A1 | 2/2016 | May et al. |
| 2016/0046963 A1 | 2/2016 | May et al. |
| 2016/0046978 A1 | 2/2016 | May et al. |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0068887 A1 | 3/2016 | May et al. |
| 2016/0076020 A1 | 3/2016 | May et al. |
| 2016/0090607 A1 | 3/2016 | Conway et al. |
| 2016/0102324 A1 | 4/2016 | Duchateau et al. |
| 2016/0108470 A1 | 4/2016 | May et al. |
| 2016/0115488 A1 | 4/2016 | Zhang et al. |
| 2016/0115489 A1 | 4/2016 | Zhang et al. |
| 2016/0122774 A1 | 5/2016 | Duchateau et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0138046 A1 | 5/2016 | Wu |
| 2016/0145646 A1 | 5/2016 | Frendewey et al. |
| 2016/0153003 A1 | 6/2016 | Joung et al. |
| 2016/0153004 A1 | 6/2016 | Zhang et al. |
| 2016/0153006 A1 | 6/2016 | Zhang et al. |
| 2016/0160210 A1 | 6/2016 | Mali et al. |
| 2016/0168592 A1 | 6/2016 | Church et al. |
| 2016/0175462 A1 | 6/2016 | Zhang et al. |
| 2016/0184362 A1 | 6/2016 | Duchateau et al. |
| 2016/0186152 A1 | 6/2016 | Brouns et al. |
| 2016/0186213 A1 | 6/2016 | Zhang et al. |
| 2016/0186214 A1 | 6/2016 | Brouns et al. |
| 2016/0201089 A1 | 7/2016 | Gersbach et al. |
| 2016/0208243 A1 | 7/2016 | Zhang et al. |
| 2016/0215276 A1 | 7/2016 | Liu et al. |
| 2016/0222416 A1 | 8/2016 | Church et al. |
| 2016/0237455 A1 | 8/2016 | Glucksmann et al. |
| 2016/0237456 A1 | 8/2016 | Church et al. |
| 2016/0251640 A1 | 9/2016 | May et al. |
| 2016/0272965 A1 | 9/2016 | Zhang et al. |
| 2016/0281072 A1 | 9/2016 | Zhang |
| 2016/0298097 A1 | 10/2016 | Chavez et al. |
| 2016/0298125 A1 | 10/2016 | Chen et al. |
| 2016/0298132 A1 | 10/2016 | Chen et al. |

(56) References Cited

U.S. PATENT DOCUMENTS

| | | |
|---|---|---|
| 2016/0298133 A1 | 10/2016 | Chen et al. |
| 2016/0298134 A1 | 10/2016 | Chen et al. |
| 2016/0298135 A1 | 10/2016 | Chen et al. |
| 2016/0298136 A1 | 10/2016 | Chen et al. |
| 2016/0298137 A1 | 10/2016 | Chen et al. |
| 2016/0298138 A1 | 10/2016 | Chen et al. |
| 2016/0304907 A1 | 10/2016 | Mali et al. |
| 2016/0312198 A1 | 10/2016 | Joung et al. |
| 2016/0312199 A1 | 10/2016 | Joung et al. |
| 2016/0312280 A1 | 10/2016 | May et al. |
| 2016/0319260 A1 | 11/2016 | Joung et al. |
| 2016/0319261 A1 | 11/2016 | Joung et al. |
| 2016/0319281 A1 | 11/2016 | Tsai et al. |
| 2016/0319349 A1 | 11/2016 | May et al. |
| 2016/0340662 A1 | 11/2016 | Zhang et al. |
| 2016/0355796 A1 | 12/2016 | Davidson et al. |
| 2016/0355797 A1 | 12/2016 | Konermann et al. |
| 2016/0355816 A1 | 12/2016 | Terns et al. |
| 2017/0037416 A1 | 2/2017 | Barrangou et al. |
| 2017/0044569 A9 | 2/2017 | Church et al. |
| 2017/0051276 A1 | 2/2017 | May et al. |
| 2017/0051310 A1 | 2/2017 | Doudna et al. |
| 2017/0051312 A1 | 2/2017 | Jinek et al. |
| 2017/0058271 A1 | 3/2017 | Joung et al. |
| 2017/0073705 A1 | 3/2017 | Chen et al. |
| 2017/0081650 A1 | 3/2017 | Joung et al. |
| 2017/0107536 A1 | 4/2017 | Zhang et al. |
| 2017/0152508 A1 | 6/2017 | Joung et al. |
| 2017/0152528 A1 | 6/2017 | Zhang |
| 2017/0166893 A1 | 6/2017 | Doudna et al. |
| 2017/0166903 A1 | 6/2017 | Zhang et al. |
| 2017/0175142 A1 | 6/2017 | Zhang et al. |
| 2017/0175144 A1 | 6/2017 | Zhang et al. |
| 2017/0191078 A1 | 7/2017 | Zhang et al. |
| 2017/0191082 A1 | 7/2017 | Chen et al. |
| 2017/0198269 A1 | 7/2017 | Zhang et al. |
| 2017/0211142 A1 | 7/2017 | Smargon et al. |
| 2017/0233703 A1 | 8/2017 | Xie et al. |
| 2017/0268022 A1 | 9/2017 | Liu et al. |
| 2017/0298330 A1 | 10/2017 | Sato et al. |
| 2017/0306307 A1 | 10/2017 | Zhang et al. |
| 2017/0306335 A1 | 10/2017 | Zhang et al. |
| 2017/0327805 A1 | 11/2017 | Joung et al. |
| 2017/0327806 A1 | 11/2017 | Joung et al. |
| 2017/0327820 A1 | 11/2017 | May et al. |
| 2017/0349915 A1 | 12/2017 | May et al. |
| 2018/0002682 A1 | 1/2018 | Sternberg et al. |
| 2018/0030425 A1 | 2/2018 | Joung et al. |
| 2018/0066242 A1 | 3/2018 | Zhang et al. |
| 2018/0073002 A1 | 3/2018 | Deiters et al. |
| 2018/0080051 A1 | 3/2018 | Sheikh et al. |
| 2018/0100148 A1 | 4/2018 | Vakulskas et al. |
| 2018/0119121 A1 | 5/2018 | Brouns et al. |
| 2018/0119175 A1 | 5/2018 | Conway et al. |
| 2018/0127780 A1 | 5/2018 | Liu et al. |
| 2018/0135073 A1 | 5/2018 | Chen et al. |
| 2018/0148735 A1 | 5/2018 | Begemann et al. |
| 2018/0155708 A1 | 6/2018 | Church et al. |
| 2018/0155716 A1 | 6/2018 | Zhang et al. |
| 2018/0163188 A1 | 6/2018 | Xie et al. |
| 2018/0163213 A1 | 6/2018 | Aneja et al. |
| 2018/0187176 A1 | 7/2018 | Behlke et al. |
| 2018/0187195 A1 | 7/2018 | Siksnys et al. |
| 2018/0208931 A1 | 7/2018 | Doudna et al. |
| 2018/0216088 A1 | 8/2018 | Joung et al. |
| 2018/0230495 A1 | 8/2018 | Doudna et al. |
| 2018/0230496 A1 | 8/2018 | Doudna et al. |
| 2018/0230497 A1 | 8/2018 | Doudna et al. |
| 2018/0237801 A1 | 8/2018 | Doudna et al. |
| 2018/0245100 A1 | 8/2018 | Doudna et al. |
| 2018/0245101 A1 | 8/2018 | Doudna et al. |
| 2018/0251791 A1 | 9/2018 | Doudna et al. |
| 2018/0251793 A1 | 9/2018 | Doudna et al. |
| 2018/0251794 A1 | 9/2018 | Doudna et al. |
| 2018/0251795 A1 | 9/2018 | Charpentier et al. |
| 2018/0265864 A1 | 9/2018 | Li et al. |
| 2018/0273981 A1 | 9/2018 | Doudna et al. |
| 2018/0282713 A1 | 10/2018 | Van Der Oost |
| 2018/0282714 A1 | 10/2018 | Joung et al. |
| 2018/0282764 A1 | 10/2018 | Jinek et al. |
| 2018/0291383 A1 | 10/2018 | Musunuru et al. |
| 2018/0298360 A1 | 10/2018 | Sternberg et al. |
| 2018/0298406 A1 | 10/2018 | Doudna et al. |
| 2018/0298407 A1 | 10/2018 | Doudna et al. |
| 2018/0312824 A1 | 11/2018 | Zhang et al. |
| 2018/0312874 A1 | 11/2018 | Doudna et al. |
| 2018/0312875 A1 | 11/2018 | Doudna et al. |
| 2018/0312876 A1 | 11/2018 | Doudna et al. |
| 2018/0319850 A1 | 11/2018 | Payne et al. |
| 2018/0320163 A1 | 11/2018 | Koonin et al. |
| 2018/0320197 A1 | 11/2018 | Gersbach et al. |
| 2018/0320201 A1 | 11/2018 | Vakulskas et al. |
| 2018/0327761 A1 | 11/2018 | Duchateau et al. |
| 2018/0346927 A1 | 12/2018 | Doudna et al. |
| 2018/0355332 A1 | 12/2018 | Steinberg et al. |
| 2019/0002889 A1 | 1/2019 | Cheng et al. |
| 2019/0002921 A1 | 1/2019 | Doudna et al. |
| 2019/0002922 A1 | 1/2019 | Doudna et al. |
| 2019/0002923 A1 | 1/2019 | Doudna et al. |
| 2019/0010471 A1 | 1/2019 | Zhang et al. |
| 2019/0010481 A1 | 1/2019 | Joung et al. |
| 2019/0010520 A1 | 1/2019 | Doudna et al. |
| 2019/0048340 A1 | 2/2019 | Charpentier et al. |
| 2019/0062790 A1 | 2/2019 | Doudna et al. |
| 2019/0071688 A1 | 3/2019 | Begemann et al. |
| 2019/0083656 A1 | 3/2019 | Khalili et al. |
| 2019/0085329 A1 | 3/2019 | Siksnys et al. |
| 2019/0093129 A1 | 3/2019 | Doudna et al. |
| 2019/0106687 A1 | 4/2019 | Joung et al. |
| 2019/0106711 A1 | 4/2019 | Doudna et al. |
| 2019/0106712 A1 | 4/2019 | Doudna et al. |
| 2019/0106713 A1 | 4/2019 | Doudna et al. |
| 2019/0106714 A1 | 4/2019 | Doudna et al. |
| 2019/0106715 A1 | 4/2019 | Doudna et al. |
| 2019/0161743 A1 | 5/2019 | Church et al. |
| 2019/0218602 A1 | 7/2019 | Zhang et al. |
| 2019/0264186 A1 | 8/2019 | Yamano et al. |
| 2019/0284583 A1 | 9/2019 | Doudna et al. |
| 2020/0056164 A1 | 2/2020 | Steinberg et al. |

FOREIGN PATENT DOCUMENTS

| | | |
|---|---|---|
| WO | WO-01/88197 A2 | 11/2001 |
| WO | WO-2007/025097 A2 | 3/2007 |
| WO | WO-2010/011961 A2 | 1/2010 |
| WO | WO-2011/091324 A2 | 7/2011 |
| WO | WO-2013/098244 A1 | 7/2013 |
| WO | WO-2013/141680 A1 | 9/2013 |
| WO | WO-2013/142578 A1 | 9/2013 |
| WO | WO-2013/176772 A1 | 11/2013 |
| WO | WO-2014/018423 A2 | 1/2014 |
| WO | WO-2014/065596 A1 | 5/2014 |
| WO | WO-2014/089290 A1 | 6/2014 |
| WO | WO-2014/093479 A1 | 6/2014 |
| WO | WO-2014/093595 A1 | 6/2014 |
| WO | WO-2014/093622 A2 | 6/2014 |
| WO | WO-2014/093635 A1 | 6/2014 |
| WO | WO-2014/093655 A2 | 6/2014 |
| WO | WO-2014/093661 A2 | 6/2014 |
| WO | WO-2014/093694 A1 | 6/2014 |
| WO | WO-2014/093701 A1 | 6/2014 |
| WO | WO-2014/093709 A1 | 6/2014 |
| WO | WO-2014/093712 A1 | 6/2014 |
| WO | WO-2014/093718 A1 | 6/2014 |
| WO | WO-2014/099744 A1 | 6/2014 |
| WO | WO-2014/099750 A2 | 6/2014 |
| WO | WO-2014/113493 A1 | 7/2014 |
| WO | WO-2014/144288 A1 | 9/2014 |
| WO | WO-2014/144592 A2 | 9/2014 |
| WO | WO-2014/144761 A2 | 9/2014 |
| WO | WO-2014/145599 A2 | 9/2014 |
| WO | WO-2014/150624 A1 | 9/2014 |
| WO | WO-2014/152432 A2 | 9/2014 |
| WO | WO-2014/165825 A2 | 10/2014 |

(56) References Cited

FOREIGN PATENT DOCUMENTS

| | | |
|---|---|---|
| WO | WO-2014/186585 A2 | 11/2014 |
| WO | WO-2014/191518 A1 | 12/2014 |
| WO | WO-2014/191521 A2 | 12/2014 |
| WO | WO-2014/197568 A2 | 12/2014 |
| WO | WO-2014/197748 A2 | 12/2014 |
| WO | WO-2014/204578 A1 | 12/2014 |
| WO | WO-2014/204724 A1 | 12/2014 |
| WO | WO-2014/204725 A1 | 12/2014 |
| WO | WO-2014/204727 A1 | 12/2014 |
| WO | WO-2014/204728 A1 | 12/2014 |
| WO | WO-2014/204729 A1 | 12/2014 |
| WO | WO-2015/006290 A1 | 1/2015 |
| WO | WO-2015/006294 A2 | 1/2015 |
| WO | WO-2015/010114 A1 | 1/2015 |
| WO | WO-2015/013583 A2 | 1/2015 |
| WO | WO-2015/021426 A1 | 2/2015 |
| WO | WO-2015/035162 A2 | 3/2015 |
| WO | WO-2015/048577 A2 | 4/2015 |
| WO | WO-2015/077318 A1 | 5/2015 |
| WO | WO-2015/086798 A2 | 6/2015 |
| WO | WO-2015/089351 A1 | 6/2015 |
| WO | WO-2015/089354 A1 | 6/2015 |
| WO | WO-2015/089427 A1 | 6/2015 |
| WO | WO-2015/089486 A2 | 6/2015 |
| WO | WO-2015/161276 A2 | 10/2015 |
| WO | WO-2015/188056 A1 | 12/2015 |
| WO | WO-2015/188065 A1 | 12/2015 |
| WO | WO-2016/022363 A2 | 2/2016 |
| WO | WO-2016/028682 A1 | 2/2016 |
| WO | WO-2016/057821 A2 | 4/2016 |
| WO | WO-2016/073990 A2 | 5/2016 |
| WO | WO-2016/081923 A2 | 5/2016 |
| WO | WO-2016/084088 A1 | 6/2016 |
| WO | WO-2016/100272 A1 | 6/2016 |
| WO | WO-2016/106236 A1 | 6/2016 |
| WO | WO-2016/106244 A1 | 6/2016 |
| WO | WO-2016/112242 A1 | 7/2016 |
| WO | WO-2016/114972 A1 | 7/2016 |
| WO | WO-2016/141224 A1 | 9/2016 |
| WO | WO-2016/161207 A1 | 10/2016 |
| WO | WO-2016/164797 A1 | 10/2016 |
| WO | WO-2016/166340 A1 | 10/2016 |
| WO | WO-2016/167300 A1 | 10/2016 |
| WO | WO-2016/196655 A1 | 12/2016 |
| WO | WO-2016/205613 A1 | 12/2016 |
| WO | WO-2016/205711 A1 | 12/2016 |
| WO | WO-2016/205745 A2 | 12/2016 |
| WO | WO-2016/205749 A1 | 12/2016 |
| WO | WO-2016/205759 A1 | 12/2016 |
| WO | WO-2017/015015 A1 | 1/2017 |
| WO | WO-2017/019895 A1 | 2/2017 |
| WO | WO-2017/040348 A1 | 3/2017 |
| WO | WO-2017/048969 A1 | 3/2017 |
| WO | WO-2017/064546 A1 | 4/2017 |
| WO | WO-2017/066588 A2 | 4/2017 |
| WO | WO-2017/070633 A2 | 4/2017 |
| WO | WO-2017/081288 A1 | 5/2017 |
| WO | WO-2017/099494 A1 | 6/2017 |
| WO | WO-2017/127807 A1 | 7/2017 |
| WO | WO-2017/136335 A1 | 8/2017 |
| WO | WO-2017/161068 A1 | 9/2017 |
| WO | WO-2017/181107 A2 | 10/2017 |
| WO | WO-2017/184768 A1 | 10/2017 |
| WO | WO-2017/189308 A1 | 11/2017 |
| WO | WO-2017/197238 A1 | 11/2017 |
| WO | WO-2017/219027 A1 | 12/2017 |
| WO | WO-2017/219033 A1 | 12/2017 |
| WO | WO-2017/222773 A1 | 12/2017 |
| WO | WO-2018/022634 A1 | 2/2018 |
| WO | WO-2018/035250 A1 | 2/2018 |
| WO | WO-2018/035387 A1 | 2/2018 |
| WO | WO-2018/035388 A1 | 2/2018 |
| WO | WO-2018/049073 A1 | 3/2018 |
| WO | WO-2018/049077 A1 | 3/2018 |
| WO | WO-2018/049079 A1 | 3/2018 |
| WO | WO-2018/052247 A1 | 3/2018 |
| WO | WO-2018/053053 A1 | 3/2018 |
| WO | WO-2018/064352 A1 | 4/2018 |
| WO | WO-2018/064371 A1 | 4/2018 |
| WO | WO-2018/068053 A2 | 4/2018 |
| WO | WO-2018/069474 A1 | 4/2018 |
| WO | WO-2018/071868 A1 | 4/2018 |
| WO | WO-2018/071892 A1 | 4/2018 |
| WO | WO-2018/074979 A1 | 4/2018 |
| WO | WO-2018/089664 A1 | 5/2018 |
| WO | WO-2018/098383 A1 | 5/2018 |
| WO | WO-2018/108272 A1 | 6/2018 |
| WO | WO-2018/108338 A1 | 6/2018 |
| WO | WO-2018/108339 A1 | 6/2018 |
| WO | WO-2018/109101 A1 | 6/2018 |
| WO | WO-2018/112451 A1 | 6/2018 |
| WO | WO-2018/118968 A1 | 6/2018 |
| WO | WO-2018/119010 A1 | 6/2018 |
| WO | WO-2018/129368 A2 | 7/2018 |
| WO | WO-2018/149888 A1 | 8/2018 |
| WO | WO-2018/170015 A1 | 9/2018 |
| WO | WO-2018/172556 A1 | 9/2018 |
| WO | WO-2018/183766 A1 | 10/2018 |
| WO | WO-2018/188571 A1 | 10/2018 |
| WO | WO-2018/191715 A2 | 10/2018 |
| WO | WO-2018/195540 A1 | 10/2018 |
| WO | WO-2018/195545 A2 | 10/2018 |
| WO | WO-2018/197495 A1 | 11/2018 |
| WO | WO-2018/209712 A1 | 11/2018 |
| WO | WO-2018/213351 A1 | 11/2018 |
| WO | WO-2018/221685 A1 | 12/2018 |
| WO | WO-2018/226855 A1 | 12/2018 |
| WO | WO-2018/227114 A1 | 12/2018 |
| WO | WO-2019/006471 A2 | 1/2019 |
| WO | WO-2019/009682 A2 | 1/2019 |
| WO | WO-2019/018041 A1 | 1/2019 |
| WO | WO-2019/036513 A1 | 2/2019 |
| WO | WO-2019/040650 A1 | 2/2019 |
| WO | WO-2019/046540 A1 | 3/2019 |
| WO | WO-2019/049913 A1 | 3/2019 |
| WO | WO-2019/051419 A1 | 3/2019 |
| WO | WO-2019/060469 A2 | 3/2019 |
| WO | WO-2019/067322 A1 | 4/2019 |
| WO | WO-2019/072596 A1 | 4/2019 |
| WO | WO-2019/074542 A1 | 4/2019 |
| WO | WO-2019/083532 A1 | 5/2019 |
| WO | WO-2019/089796 A1 | 5/2019 |
| WO | WO-2019/089804 A1 | 5/2019 |
| WO | WO-2019/089808 A1 | 5/2019 |
| WO | WO-2019/089820 A1 | 5/2019 |
| WO | WO-2019/090173 A1 | 5/2019 |
| WO | WO-2019/090174 A1 | 5/2019 |
| WO | WO-2019/090175 A1 | 5/2019 |
| WO | WO-2019/092042 A1 | 5/2019 |
| WO | WO-2019/092505 A1 | 5/2019 |
| WO | WO-2019/099943 A1 | 5/2019 |
| WO | WO-2019/126709 A1 | 6/2019 |
| WO | WO-2019/126716 A1 | 6/2019 |
| WO | WO-2019/126762 A2 | 6/2019 |
| WO | WO-2019/126774 A1 | 6/2019 |
| WO | WO-2019/168953 A1 | 9/2019 |
| WO | WO-2019/178427 A1 | 9/2019 |
| WO | WO-2019/178428 A1 | 9/2019 |
| WO | WO-2019/183150 A1 | 9/2019 |

OTHER PUBLICATIONS

Altschul, S.F. et al., Basic local alignment search tool, J. Mol. Biol., 215(3): 403-410 (1990).
Altschul, S.F. et al., Gapped Blast and PSI-Blast: a new generation of protein database search programs, Nucleic Acids Res., 25:3389-3402, (1997).
Altschul, S.F. et al., Local alignment statistics, Methods in Enzymology, 26: 460-480 (1996).
Anders, C. et al., Structural basis of PAM-dependent target DNA recognition by the Cas9 endonuclease, Nature, 513(7519):569-73 (2014).
Briner, A. E. et al. Guide RNA functional modules direct Cas9 activity and orthogonality Molecular Cell, 56(2), 333-339 (2014).

(56) References Cited

OTHER PUBLICATIONS

Chen, J.S. et al., Enhanced proofreading governs CRISPR-Cas9 targeting accuracy, Nature, 550:407-410 (2017).

Cong, L. et al., Multiplex genome engineering using CRISPR/Cas systems, Science, 339(6121):819-23 (2013).

Esvelt, K. M. and Wang, H.H., Genome-scale engineering for systems and synthetic biology Molecular Systems Biology, 9:641 (2013).

Guo, H. H. et al, Protein tolerance to random amino acid change, PNAS. 101(25): 9205-9210 (2004).

Hsu, P.D. et al., DNA targeting specificity of RNA-guided Cas9 nucleases, Nat Biotechnol, 31(9): 827-832 (2013).

Hu, J. H. et al,Evolved Cas9 variants with broad PAM compatibility and high DNA specificity, Nature, 556(7699): 57-63 (2018).

International Search Report for PCT/US2018/025282 (Selection Methods, filed Mar. 29, 2018), issued by ISA/EPO, 10 pages (Jul. 20, 2018).

International Search Report for PCT/US2018/036695 (Engineered CAS9 Nucleases, filed Jun. 8, 2018), issued by ISA/EPO, 5 pages (Sep. 14, 2018).

Jiang, W. et al. RNA-guided editing of bacterial genomes using CRISPR-Cas systems, Nat Biotechnol., 31(3): 233-239 (2013).

Jinek, M. et al., A programmable dual-RNA-guided DNA endonuclease in adaptive, bacterial immunity, Science, 337(6096): 816-821 (2012).

Jinek, M. et al., Structures of Cas9 endonucleases reveal RNA-mediated conformational activation, Science, 343(6176), 1247997 (2014).

Kim, D. et al., Digenome-seq: genome-wide profiling of CRISPR-Cas9 off-target effects in human cells, Nature Methods, 12:237-243 (2015).

Kim, T. K. and Eberwine, J. H., Mammalian cell transfection: the present and the future, Anal. Bioanal. Chem. 397:3173-78 (2010).

Kleinstiver, B. P. et al, High-fidelity CRISPR-Cas9 nucleases with no detectable genome-wide off-target effects, Nature, 529: 490-95 (2016).

Kleinstiver, B.P. et al., Broadening the targeting range of *Staphylococcus aureus* CRISPR-Cas9 by modifying PAM recognition, Nature Biotechnology, 33:1293-1298 (2015).

Kleinstiver, B.P. et al., Engineered CRISPR-Cas9 nucleases with altered PAM specificities, Nature, 523:481-485 (2015).

Mali, P. et al., RNA-guided human genome engineering via Cas9, Science, 339(6121): 823-826 (2013).

Mout, R. et al., Direct Cytosolic Delivery of CRISPR/Cas9-Ribonucleoprotein for Efficient Gene Editing, ACS Nano 11:2452-58 (2017).

Nishimasu, H. et al., Crystal structure of Cas9 in complex with guide RNA and target DNA. Cell, 156: 935-949 (2014).

Nishimasu, H. et al., Crystal Structure of *Staphylococcus aureus* Cas9, Cell, 162:1113-1126 (2015).

O'Geen et al., A genome-wide analysis of Cas9 binding specificity using ChIP-seq and targeted sequence capture, Nucleic Acids Res. 43:3389-3404 (2015).

Palva, I. et al., Secretion of interferon by Bacillus subtilis, Gene, 22:229-235 (1983).

Ran, F. A. et al., Double nicking by RNA-guided CRISPR Cas9 for enhanced genome editing specificity, Cell 154(6), 1380-1389 (2013).

Roy, A. C. et al, Perpetuating the homing endonuclease life cycle: identification of mutations that modulate and change I-TevI cleavage preference, Nucleic Acids Research,44(15): 7350-7359 (2016).

Shmakov, S. et al., Discovery and Functional Characterization of Diverse Class 2 CRISPR-Cas Systems, Molecular cell, 60:385-397 (2015).

Slaymaker, I. M., et al, Rationally engineered Cas9 nucleases with improved specificity, Science, 351(6268):84-88 (2016).

Steinberg, B. et al, Directed evolution of targeted Cas9 cleavage to the LCAIO splice donor mutation, (May 5, 2017), XP055491620, Retrieved from <<http://www.editasmedicine.com/data/documents/ 170502 directed evolution of targeted cas9 cleavage to the IcaIO splice 1497464968.pdf>>.Accessed on Jul. 10, 2018.

Steinberg, B. et al, Directed evolution of Cas9 to reduce identified off-target cleavage, Editas Medicine, Jun. 13, 2017 (Jun. 13, 2017), XP055491603, Retrieved from the Internet: URL:http://www. editasmedicine.com/data/documents/bigsky 2017 pdl final 14973793951497468459.pdf >> Accessed on Jul. 10, 2018.

Thyme, S. B. et al, Reprogramming homing endonuclease specificity through computational design and directed evolution, Nucleic Acid Research, 42(4): 2564-2576 (2013).

Tsai, S. Q. et al, Circle-seq: a highly sensitive in vitro screen for genome-wide CRISPR-Cas9 nuclease off-targets, Nature Methods, 14:607-614 (2017).

Tsai, S. Q. et al. Guide-seq enables genome-wide profiling of off-target cleavage by CRISPR-Cas nucleases, Nat. Biotechnol., 33:187-197 (2015).

Wang, L. et al., A Novel Genetic System Based on Zinc Finger Nucleases for the Identification of Interactions between Proteins In Vivo, PLoS One, 8(12):e85650 (2013).

Written Opinion for PCT/US2018/025282 (Selection Methods, filed Mar. 29, 2018), issued by ISA/EPO, 19 pages (Jul. 20, 2018).

Written Opinion for PCT/US2018/036695 (Engineered CAS9 Nucleases, filed Jun. 8, 2018), issued by ISA/EPO, 8 pages (Sep. 14, 2018).

Yamano, T. et al. Crystal Structure of Cpf1 in Complex with Guide RNA and Target DNA, Cell, 165(4): 949-962 (2016).

Zetsche et al., Cpf1 Is a Single RNA-Guided Endonuclease of a Class 2 CRISPR-Cas System, Cell, 163:759-771 ( 2015).

Zuris, J. A. et al., Cationic lipid-mediated delivery of proteins enables efficient protein-based genome editing in vitro and in vivo, Nature Biotechnol., 33(1):73-80 (2015).

\* cited by examiner

```
NmCas9    1 AAFKPNSINYILGLDIGIASVGWAMVEIDEEENP--------------IR   36
            ....|.:||||..||||::  .||.:.|                  |:
SpCas9    1 -----MDKKYSIGLDIGTNSVGWAVI-TDEYKVPSKKFKVLGNTDRHSIK   44

NmCas9   37 LIDLGVRVFERAEVPKTGDSLAMARRLARSVRRLTRRRAHRLLRTRRLLK   86
            ...:|..:|:..|.       |.|.||.|:.||...||.:|:........
SpCas9   45 KNLIGALLFDSGET-------AEATRLKRTARRRYTRRKNRICYLQEIFS   87

NmCas9   87 REGVLQAANF----------------------DENGLIKSLPNTPW     110
            .|......:|                       ||....:..| |.:
SpCas9   88 NEMAKVDDSFFHRLEESFLVEEDKKHERHPIFGNIVDEVAYHEKYP-TIY  136

NmCas9  111 QLRAAALDR------KLTPLEWSAVLLHLIKHRGY---------        139
            .||...:|.      :|..|    .|.|:||.||:
SpCas9  137 HLRKKLVDSTDKADLRLIYL----ALAHMIKFRGHFLIEGDLNPDNSDVD  182

NmCas9  140 ----LSQRKNE----------GETADKELGALL----------        158
                |.|..|:           |...|...|.|.|
SpCas9  183 KLFIQLVQTYNQLFEENPINASGVDAKAILSARLSKSRRLENLIAQLPGE  232

NmCas9  159 --KGVAGNAHALQTG---------DFRTPAELALNK--FEKESGHIRNQR  195
              .|:.||..||..|         |....|:.|:|    :..:..::..|.
SpCas9  233 KKNGLFGNLIALSLGLTPNFKSNFDLAEDAKLQLSKDTYDDDLDNLLAQI  282

NmCas9  196 SD-YSHTF-----------------------SRKDLQAELI--------  212
            .| |:..|                       :::..|.|.:|
SpCas9  283 GDQYADLFLAAKNLSDAILLSDILRVNTEITKAPLSASMIKRYDEHHQDL  332

NmCas9  213 ----------------LLFEKQKEFGNPHVSGG---------         229
                            :.|::.|........:..||
SpCas9  333 TLLKALVRQQLPEKYKEIFFDQSKNGYAGYIDGGASQEEFYKFIKPILEK  382

NmCas9  230 --------LKEGIETLLMTQRPALSG----------------         247
                    :|...|.||..||...:|
SpCas9  383 MDGTEELLVKLNREDLLRKQRTFDNGSIPHQIHLGELHAILRRQEDFYPF  432

NmCas9  248 -----DAVQKMLGHCTFE-P--AEPKAAKNTYTAERFIWLTK-------  281
                 :.::|:|  ||. |  ..|.|..|:    ||.|:|:
SpCas9  433 LKDNREKIEKIL---TFRIPYYVGPLARGNS----RFAWMTRKSEETITP  475

NmCas9  282 ------------------------------LN                  283
                                          |.
SpCas9  476 WNFEEVVDKGASAQSFIERMTNFDKNLPNEKVLPKHSLLYEYFTVYNELT  525

NmCas9  284 NLRILEQGSERP--LTDTERATLMDEPYRKS-KLTYAQARKLLGLEDTAF  330
            .::.:.:|..:|  |:..:..::|..::.: |:|..|.   ||  :
SpCas9  526 KVKYVTEGMRKPAFLSGEQKKAIVDLLFKTNRKVTVKQLK-----ED--Y  568
```

Figure 17

```
NmCas9   331  FKGLRYGKDNAEASTLME-----MKAYHAISRALEKEGLKDKKSPLNLSP   375
              |.:..  .|:.|.|.:.:      :..||.:.:..:.:..|:.       :.
SpCas9   569  FKKIEC-FDSVEISGVEDRFNASLGTYHDLLKIIKDKDFLDNEE----NE   613

NmCas9   376  ELQDEIGTAFSLFKTDEDITGRLK-------DRIQPEILEALLKHISFDK   418
              :.:.:|....:||:..|..|||      |:..:    ||....:..
SpCas9   614  DILEDIVLTLTLFEDREMIEERLKTYAHLFDDKVMKQ-----LKRRRYTG   658

NmCas9   419  FVQISLKALRRIVPLMEQGKRYDEACAE-IYGDHYGKKNTEEKIYLPPIP   467
              :.::|.|.:..|      :.|:..:...: :..|.:.:|...|:....:.
SpCas9   659  WGRLSRKLINGI------RDKQSGKTILDFLKSDGFANRNFMQLIHDDSLT   703

NmCas9   468  ADE-----------------IRN----PVVLRALSQARKVINGVVRRYG-   495
              ..|                   |.|       |.:.:.:.|..||:..:|:..|
SpCas9   704  FKEDIQKAQVSGQGDSLHEHIANLAGSPAIKKGILQTVKVVDELVKVMGR   753

NmCas9   496  -SPARIHIETARE---VGKSFKDRKEIEKRQEENRKDREKAAAKFREYFP   541
              .|..|.||.|||   ..|.|:.:|..||.||..|  |.:.....:|:
SpCas9   754  HKPENIVIEMARENQTTQKGQKNSRERMKRIEEGIK---ELGSQILKEH--   799

NmCas9   542  NFVGEPKSKDIL---KLRLYEQQHGKCLYSGKEINLGRLNEKGYVEIDHA   588
              |......|    ||.||..|:.:.|..:|:::.||::   .::||.
SpCas9   800  -----PVENTQLQNEKLYLYYLQNGRDMYVDQELDINRLSD---YDVDHI   841

NmCas9   589  LPFSRTWDDSFNNKVLVLGSENQNKGNQTPYEYFNGKDNSREWQEFKARV   638
              :|.|...|||.:||||....:.:.|.:..|.....|.:..|...|::
SpCas9   842  VPQSFLKDDSIDNKVLTRSDKNRGKSDNVPSEEVVKKMKNYWRQLLNAKL   891

NmCas9   639  ETSR-FPR-SKKQRILLQKFDEDGFKERNLNDTRYVNRFLCQFVADRMRL   686
              .|.| |.. :|.:|..|.:.|..|.:.||.:|.|.:|:.:.:.:.||.
SpCas9   892  ITQRKFDNLTKAERGGLSELDKAGFIKRQLVETRQITKHVAQILDSRMNT   941

NmCas9   687  T-GKGKK------RVFASNGQITNLLRGFWGLRKVRAENDRHHALDAVVA   730
              .  .:..|    :|.....:.:.:.|..:....|||.|:.|||.|.:.|
SpCas9   942  KYDENDKLIREVKVITLKSKLVSDFRKDFQFYKVREINNYHHAHDAYLNA   991

NmCas9   731  CSTVAMQQKI----TRFVRYKEMNAFDGKTI----DKETGEVLHQKTHFP   772
              ....|:..:.   :.||  |.:.....:|.:.:   ::|.|:.......:.
SpCas9   992  VVGTALIKKYPKLESEFV-YGDYKVYDVRKMIAKSEQEIGKATAKYFFYS   1040

NmCas9   773  QPWEFFAQEVMIRVFGKPDGKPEFEEADTLEKLRTLLAEKLSSRP-----   817
              ....||..|:                              ||...::..||
SpCas9   1041 NIMNFFKTEI-------------------------TLANGEIRKRPLIETN   1066

NmCas9   818  EAVHEYVTPLFVSRAPNRKMSGQGHMETVKSAKRLDEGVSVLRVPLTQLK   867
              ....|.|........|..||:........|.:.:.|.:..:|.:...:  |.
SpCas9   1067 GETGEIVWDKGRDFATVRKVLSMPQVNIVKKTEVQTGGFSKESI-----LP   1112
```

Figure 17 cont'd

```
NmCas9   868 LKDLEKMVNRER--EPKLYEALKARLEAHKDDPAKAFAE-PFYKYDKAGN  914
             .::.:|::.|::  :||.|...        |.|..|::. ...|.:|  .
SpCas9  1113 KRNSDKLIARKKDWDPKKYGGF--------DSPTVAYSVLVVAKVEK--G 1152

NmCas9   915 RTQQVKAVRVEQVQKTGVWVRNHNGIADNATMVRVDVFE-------KGDK  957
             :::::|:|:   :..|:.:.........|.   :|..|       |.|.
SpCas9  1153 KSKKLKSVK----ELLGITIMERSSFEKNP----IDFLEAKGYKEVKKDL 1194

NmCas9   958 YYLVPIYS---------------WQVAKG---ILPDRAV-----------  978
             ...:|.||               .::.||   .||.:.|
SpCas9  1195 IIKLPKYSLFELENGRKRMLASAGELQKGNELALPSKYVNFLYLASHYEK 1244

NmCas9   979 VQG---KDEEDWQLIDDSFNFKFSLHPNDLVEVITKKARMFGYFASCHRGT 1026
             ::|   :|.|...||...:       |.:.|.|:|.:.:
SpCas9  1245 LKGSPEDNEQKQLFVEQ-------HKHYLDEIIEQIS------------- 1274

NmCas9  1027 GNINIRIHDLDHKIGKNGILEGIGVKTALSFQKYQIDELGKEIRPCRLKK 1076
                        :...|..||....:...||......|:
SpCas9  1275 -----------EFSKRVILADANLDKVLSAYNKHRDK------------- 1300

NmCas9  1077 RPPVR--------------------------------------------- 1081
                  |:|
SpCas9  1301 --PIREQAENIIHLFTLTNLGAPAAFKYFDTTIDRKRYTSTKEVLDATLI 1348

NmCas9  1082 -------------------  1081

SpCas9  1349 HQSITGLYETRIDLSQLGGD   1368
```

Figure 17 cont'd

| Genome Editing System Components |||| 
|---|---|---|---|
| RNA-guided Nuclease | gRNA | Donor Template | Comments |
| Protein | RNA | [N/A] | An RNA-guided nuclease protein complexed with a gRNA molecule (an RNP complex) |
| Protein | RNA | DNA | An RNP complex as described above plus a single-stranded or double stranded donor template. |
| Protein | DNA | [N/A] | An RNA-guided nuclease protein plus gRNA transcribed from DNA. |
| Protein | DNA | DNA | An RNA-guided nuclease protein plus gRNA-encoding DNA and a separate DNA donor template. |
| Protein | DNA || An RNA-guided nuclease protein and a single DNA encoding both a gRNA and a donor template. |
| DNA ||| A DNA or DNA vector encoding an RNA-guided nuclease, a gRNA and a donor template. |
| DNA | DNA | [N/A] | Two separate DNAs, or two separate DNA vectors, encoding the RNA-guided nuclease and the gRNA, respectively. |
| DNA | DNA | DNA | Three separate DNAs, or three separate DNA vectors, encoding the RNA-guided nuclease, the gRNA and the donor template, respectively. |
| DNA || [N/A] | A DNA or DNA vector encoding an RNA-guided nuclease and a gRNA |

Figure 19

| | | | |
|---|---|---|---|
| DNA | | DNA | A first DNA or DNA vector encoding an RNA-guided nuclease and a gRNA, and a second DNA or DNA vector encoding a donor template. |
| DNA | | DNA | A first DNA or DNA vector encoding an RNA-guided nuclease and second DNA or DNA vector encoding a gRNA and a donor template. |
| | DNA | | A first DNA or DNA vector encoding an RNA-guided nuclease and a donor template, and a second DNA or DNA vector encoding a gRNA |
| | DNA | | |
| | DNA | | A DNA or DNA vector encoding an RNA-guided nuclease and a donor template, and a gRNA |
| | RNA | | |
| RNA | | [N/A] | An RNA or RNA vector encoding an RNA-guided nuclease and comprising a gRNA |
| RNA | | DNA | An RNA or RNA vector encoding an RNA-guided nuclease and comprising a gRNA, and a DNA or DNA vector encoding a donor template. |
| RNA | RNA | [N/A] | An RNA or RNA vector encoding an RNA-guided nuclease and a gRNA |
| RNA | RNA | DNA | An RNA or RNA vector encoding an RNA-guided nuclease, a gRNA, and a DNA or DNA vector encoding a donor template |
| RNA | DNA | [N/A] | An RNA or RNA vector encoding an RNA-guided nuclease and a DNA or DNA vector encoding a gRNA. |
| RNA | DNA | DNA | An RNA or RNA vector encoding an RNA-guided nuclease, a DNA or DNA vector encoding a gRNA, and a DNA or DNA vector encoding a donor template. |
| RNA | | DNA | An RNA or RNA vector encoding an RNA-guided nuclease and a single DNA encoding both a gRNA and a donor template. |

Figure 19 (cont.)

ENGINEERED CAS9 NUCLEASES

CROSS REFERENCE TO RELATED APPLICATIONS

This application is a continuation of U. S. Non-Provisional application Ser. No. 16/544,452, filed Aug. 19, 2019, which is a division of U.S. Non-Provisional application Ser. No. 16/003,967, filed Jun. 8, 2018, which claims priority to U.S. Provisional Application 62/517,811, filed Jun. 9, 2017 and to U.S. Provisional Application No. 62/665,388 filed May 1, 2018, the contents of all of which are hereby incorporated by reference in their entireties.

SEQUENCE LISTING

The present specification makes reference to a Sequence Listing (submitted electronically as a .txt file named "2011271-0108SL.txt" on Jul. 14, 2021. The .txt file was generated on Nov. 6, 2019 and is 41,553 bytes in size. The entire contents of the Sequence Listing are herein incorporated by reference.

FIELD

The present disclosure relates to CRISPR/Cas-related methods and components for editing a target nucleic acid sequence, or modulating expression of a target nucleic acid sequence, and applications thereof in connection with. More particularly, the disclosure relates to engineered Cas9 nucleases with altered and improved target specificity.

BACKGROUND

CRISPRs (Clustered Regularly Interspaced Short Palindromic Repeats) evolved in bacteria and archaea as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complementary to the viral genome, mediates targeting of an RNAguided nuclease protein such as Cas9 or Cpf1 to a target sequence in the viral genome. The RNA-guided nuclease, in turn, cleaves and thereby silences the viral target.

CRISPR systems have been adapted for genome editing in eukaryotic cells. These systems generally include a protein component (the RNA-guided nuclease) and a nucleic acid component (generally referred to as a guide RNA or "gRNA"). These two components form a complex that interacts with specific target DNA sequences recognized by, or complementary to, the two components of the system and optionally edits or alters the target sequence, for example by means of site-specific DNA cleavage.

The value of nucleases such as these as a tool for the treatment of inherited diseases is widely recognized. For example, the U.S. Food and Drug Administration (FDA) held a Science Board Meeting on Nov. 15, 2016 addressing the use of such systems and potential regulatory considerations raised by them. In that meeting, the FDA noted that while Cas9/guide RNA (gRNA) ribonucleoprotein (RNP) complexes may be customized to generate precise edits at a locus of interest, the complexes may also interact with, and cut at, other "off-target" loci. The potential for off-target cuts ("off-targets"), in turn, raises at least a potential regulatory consideration with respect to the approval of therapeutics utilizing these nucleases.

SUMMARY

The present disclosure addresses potential regulatory considerations by providing, in part, engineered RNA-guided nucleases that exhibit improved specificity for targeting a DNA sequence, e.g., relative to a wild-type nuclease. Improved specificity can be, e.g., (i) increased on-target binding, cleavage and/or editing of DNA and/or (ii) decreased off-target binding, cleavage and/or editing of DNA, e.g., relative to a wild-type RNA-guided nuclease and/or to another variant nuclease.

In one aspect, the present disclosure provides an isolated *Staphylococcus pyogenes* Cas9 (SPCas9) polypeptide comprising an amino acid substitution, relative to a wild-type SPCas9, at one or more of the following positions: D23, D1251, Y128, T67, N497, R661, Q695, and/or Q926. In some embodiments, the isolated SPCas9 polypeptide comprises an amino acid sequence having at least 80%, 85%, 90%, 95%, 96%, 97%, 98%, or 99% identity to the amino acid sequence of SEQ ID NO: 13, wherein the polypeptide comprises an amino acid substitution at one or more of the following positions of SEQ ID NO:13: D23, D1251, Y128, T67, N497, R661, Q695, and/or Q926.

In some embodiments, the isolated polypeptide comprises one or more of the following amino acid substitutions: D23A, Y128V, T67L, N497A, D1251G, R661A, Q695A, and/or Q926A. In some embodiments, the isolated polypeptide comprises the following amino acid substitutions: D23A/Y128V/D1251G/T67L.

In another aspect, the disclosure provides a fusion protein comprising an isolated polypeptide described herein, fused to a heterologous functional domain, with an optional intervening linker, wherein the linker does not interfere with activity of the fusion protein. In some embodiments, the heterologous functional domain is selected from the group consisting of: VP64, NF-kappa B p65, Krueppel-associated box (KRAB) domain, ERF repressor domain (ERD), mSin3A interaction domain (SID), Heterochromatin Protein 1 (HP1), DNA methyltransferase (DNMT), TET protein, histone acetyltransferase (HAT), histone deacetylase (HDAC), histone methyltransferase (HMT), or histone demethylase (HDM), MS2, Csy4, lambda N protein, and Fok1.

In another aspect, the disclosure features a genome editing system comprising an isolated polypeptide described herein.

In another aspect, the disclosure features a nucleic acid encoding an isolated polypeptide described herein. In another aspect, the disclosure features a vector comprising the nucleic acid.

In another aspect, the disclosure features a composition comprising an isolated polypeptide described herein, a genome editing system described herein, a nucleic acid described herein, and/or a vector described herein and, optionally, a pharmaceutically acceptable carrier.

In another aspect, the disclosure features a method of altering a cell, comprising contacting the cell with such composition. In another aspect, the disclosure features a method of treating a patient, comprising administering to the patient such composition.

In another aspect, the disclosure features a polypeptide comprising an amino acid sequence at least about 80% identical (e.g., at least about 85%, 90%, 92%, 94%, 95%, 96%, 97%, 98%, or 99% identical) to SEQ ID NO:13 and having an amino acid substitution at one or more of positions D23, T67, Y128 and D1251 of SEQ ID NO:13. In some embodiments, the polypeptide comprises an amino acid substitution at D23. In some embodiments, the polypeptide comprises an amino acid substitution at D23 and at least one amino acid substitution at T67, Y128 or D1251. In some embodiments, the polypeptide comprises an amino acid substitution at D23 and at least two substitutions at T67, Y128 or D1251. In some embodiments, the polypeptide comprises an amino acid substitution at T67. In some embodiments, the polypeptide comprises an amino acid substitution at T67 and at least one amino acid substitution at D23, Y128 or D1251. In some embodiments, the polypeptide comprises an amino acid substitution at T67 and at least two substitutions at D23, Y128 or D1251. In some embodiments, the polypeptide comprises an amino acid substitution at Y128. In some embodiments, the polypeptide comprises an amino acid substitution at Y128 and at least one amino acid substitution at D23, T67 or D1251. In some embodiments, the polypeptide comprises an amino acid substitution at Y128 and at least two substitutions at D23, T67 or D1251. In some embodiments, the polypeptide comprises an amino acid substitution at D1251. In some embodiments, the polypeptide comprises substitution at D1251 and at least one amino acid substitution at D23, T67 or Y128. In some embodiments, the polypeptide comprises an amino acid substitution at D1251 and at least two substitutions at D23, T67 or Y128. In some embodiments, the polypeptide comprises amino acid substitutions at D23, T67, Y128 and D1251. In some embodiments, the polypeptide further includes at least one additional amino acid substitution described herein.

In some embodiments, the polypeptide, when contacted with a target double stranded DNA (dsDNA), rate of off-target editing is less than the observed rate of off-target editing of the target by a wild-type SPCas9. In some embodiments, rate of off-target editing by the polypeptide is about 5%, 10%, 15%, 20%, 25%, 30%, 40%, 50%, 60%, 70%, 80%, 90%, or 95% less than that of wild-type SPCas9. In some embodiments, rate of off-target editing is measured by assessing a level (e.g., fraction or percentage) of indels at the off-target site.

In another aspect, the disclosure features a fusion protein comprising the polypeptide and one or more of a nuclear localization sequence, cell penetrating peptide sequence, and/or affinity tag. In another aspect, the disclosure features a fusion protein comprising the polypeptide fused to a heterologous functional domain, with an optional intervening linker, wherein the linker does not interfere with activity of the fusion protein.

In some embodiments, the heterologous functional domain is a transcriptional transactivation domain. In some embodiments, the transcriptional transactivation domain is from VP64, or NFk-B p65. In some embodiments, the heterologous functional domain is a transcriptional silencer or transcriptional repression domain. In some embodiments, the transcriptional repression domain is a Krueppel-associated box (KRAB) domain, ERF repressor domain (ERD), or mSin3A interaction domain (SID). In some embodiments, the transcriptional silencer is Heterochromatin Protein 1 (HP1). In some embodiments, the heterologous functional domain is an enzyme that modifies the methylation state of DNA (e.g., a DNA methyltransferase (DNMT) or a TET protein). In some embodiments, the TET protein is TET1. In some embodiments, the heterologous functional domain is an enzyme that modifies a histone subunit (e.g., a histone acetyltransferase (HAT), histone deacetylase (HDAC), histone methyltransferase (HMT), or histone demethylase). In some embodiments, the heterologous functional domain is a biological tether (e.g., MS2, Csy4 or lambda N protein). In some embodiments, the heterologous functional domain is Fok1.

In another aspect, the disclosure features an isolated nucleic acid encoding the polypeptide described herein. In another aspect, the disclosure features a vector comprising such isolated nucleic acid. In another aspect, the disclosure features a host cell comprising such vector.

In another aspect, the disclosure features a polypeptide comprising an amino acid sequence at least about 80% identical (e.g., at least about 85%, 90%, 92%, 94%, 95%, 96%, 97%, 98%, or 99% identical) to SEQ ID NO:13 and comprising one or more of the following amino acid substitutions: D23A, T67L, Y128V, and D1251G. In some embodiments, the polypeptide comprises D23A; and/or the polypeptide comprises D23A and at least one of T67L, Y128V and D1251 G; and/or the polypeptide comprises D23A and at least two of T67L, Y128V and D1251 G; and/or the polypeptide comprises T67L; and/or the polypeptide comprises T67L and at least one of D23A, Y128V and D1251G; and/or the polypeptide comprises T67L and at least two of D23A, Y128V and D1251G; and/or the polypeptide comprises Y128V; and/or the polypeptide comprises Y128V and at least one of D23A, T67L and D1251G; and/or the polypeptide comprises Y128V and at least two of D23A, T67L and D1251G; and/or the polypeptide comprises D1251 G; and/or the polypeptide comprises D1251 G and at least one of D23A, T67L and Y128V; and/or the polypeptide comprises D1251G and at least two of D23A, T67L and Y128V; and/or the polypeptide comprises D23A, T67L, Y128V and D1251G.

In some embodiments, the polypeptide is contacted with double stranded DNA (dsDNA) target, rate of off-target editing is less than the observed rate of off-target editing of the target by a wild-type SPCas9. In some embodiments, rate of off-target editing by the polypeptide is about 5%, 10%, 15%, 20%, 30%, 40%, 50%, 60%, 70%, 80%, 90%, or 95% less than that of wild-type SPCas9. In some embodiments, rate of off-target editing is measured by assessing a level (e.g., fraction or percentage) of indels at the off-target site.

In another aspect, the disclosure features a fusion protein comprising the polypeptide, and one or more of a nuclear localization sequence, cell penetrating peptide sequence, and/or affinity tag.

In another aspect, the disclosure features a fusion protein comprising the polypeptide fused to a heterologous functional domain, with an optional intervening linker, wherein the linker does not interfere with activity of the fusion protein. In some embodiments, the heterologous functional domain is a transcriptional transactivation domain (e.g., a transactivation domain from VP64, or NFk-B p65). In some embodiments, the heterologous functional domain is a transcriptional silencer or transcriptional repression domain (e.g., a Krueppel-associated box (KRAB) domain, ERF repressor domain (ERD), or mSin3A interaction domain (SID)). In some embodiments, the transcriptional silencer is Heterochromatin Protein 1 (HP1). In some embodiments, the heterologous functional domain is an enzyme that modifies the methylation state of DNA (e.g., a DNA methyltransferase (DNMT) or a TET protein). In some embodiments, the TET protein is TET1. In some embodiments, the heterologous functional domain is an enzyme that modifies a histone subunit (e.g., a histone acetyltransferase (HAT), histone deacetylase (HDAC), histone methyltransferase (HMT), or histone demethylase). In some embodiments, the heterologous functional domain is a biological tether (e.g., MS2, Csy4 or lambda N protein). In some embodiments, the heterologous functional domain is Fok1.

In another aspect, the disclosure features an isolated nucleic acid encoding such polypeptide. In another aspect, the disclosure features a vector comprising such isolated nucleic acid. In another aspect, the disclosure features a host cell comprising such vector.

In another aspect, the disclosure features a method of genetically engineering a population of cells, the method comprising expressing in the cells or contacting the cells with a polypeptide of the disclosure (e.g., a variant nuclease described herein) and a guide nucleic acid having a region complementary to a target sequence on a target nucleic acid of the genome of the cells, whereby the genomes of at least a plurality of the cells are altered.

In some embodiments, rate of off-target editing by the polypeptide is less than the observed rate of off-target editing of the target sequence by a wild-type SPCas9. In some embodiments, rate of off-target editing by the polypeptide is about 5%, 10%, 15%, 20%, 25%, 30%, 40%, 50%, 60%, 70%, 80%, 90%, or 95% less than that of wild-type SPCas9. In some embodiments, rate of off-target editing is measured by assessing a level (e.g., fraction or percentage) of indels at the off-target site.

In some embodiments, the polypeptide and guide nucleic acid are administered as a ribonucleic protein (RNP). In some embodiments, the RNP is administered at a dose of $1 \times 10^{-4}$ µM to 1 µM RNP.

In another aspect, the disclosure features a method of editing a population of double stranded DNA(dsDNA) molecules, the method comprising contacting the dsDNA molecules with a polypeptide of the disclosure (e.g., a variant nuclease described herein), and a guide nucleic acid having a region complementary to a target sequence of the dsDNA molecules, whereby a plurality of the dsDNA molecules is edited.

In some embodiments, rate of off-target editing by the polypeptide is less than the observed rate of off-target editing of the target sequence by a wild-type SPCas9. In some embodiments, rate of off-target editing by the polypeptide is about 5%, 10%, 15%, 20%, 25%, 30%, 40%, 50%, 60%, 70%, 80%, 90%, or 95% less than that of wild-type SPCas9. In some embodiments, rate of off-target editing is measured by assessing a level (e.g., fraction or percentage) of indels at the off-target site.

In some embodiments, the polypeptide and guide nucleic acid are administered as a ribonucleic protein (RNP). In some embodiments, the RNP is administered at a dose of $1 \times 10^{-4}$ µM to 1 µM RNP.

BRIEF DESCRIPTION OF THE DRAWINGS

FIG. 17 shows an alignment of S. pyogenes and N. meningitidis Cas9 sequences.

FIG. 19 depicts several exemplary implementations of a genome editing system comprising a single gRNA and an optional donor template.

DETAILED DESCRIPTION

Definitions

Figure 1:
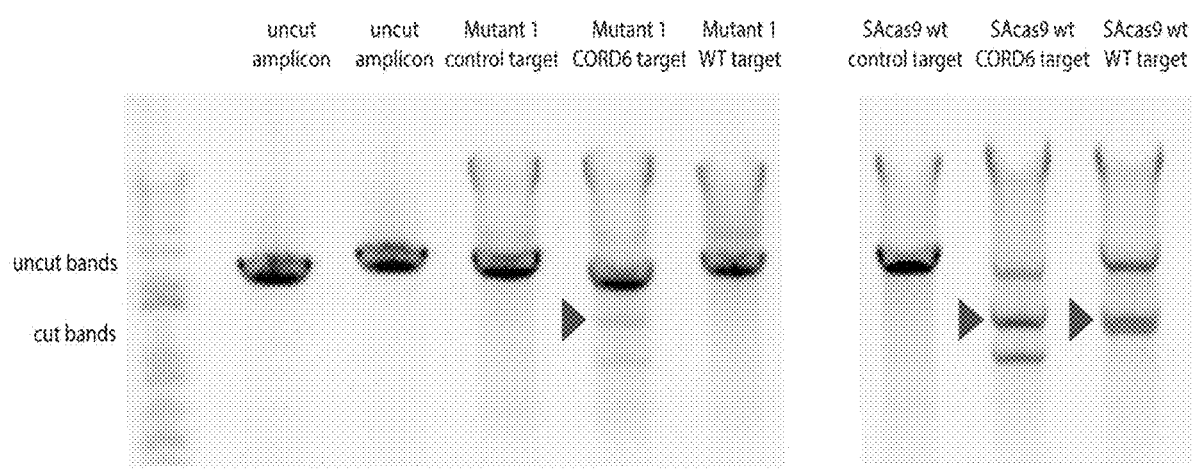
FIG. 1 depicts the results of an in vitro lysate cleavage assay of a highly selected Cas9 mutant obtained as described in Example 1. The mutant demonstrates cutting only on the CORD6 target, while the wildtype enzyme cleaves both targets (i.e., CORD6 target and wildtype target) efficiently. Bands corresponding to cleavage products are indicated by triangles.

Throughout the specification, several terms are employed that are defined in the following paragraphs. Other definitions are also found within the body of the specification.

As used herein, the terms "about" and "approximately," in reference to a number, is used herein to include numbers that fall within a range of 20%, 10%, 5%, or 1% in either direction (greater than or less than) of the number unless otherwise stated or otherwise evident from the context (except where such number would exceed 100% of a possible value).

As used herein, the term "cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or cohesive ends.

As used herein, a "conservative substitution" refers to a substitution of an amino acid made among amino acids within the following groups: i) methionine, isoleucine, leucine, valine, ii) phenylalanine, tyrosine, tryptophan, iii) lysine, arginine, histidine, iv) alanine, glycine, v) serine, threonine, vi) glutamine, asparagine and vii) glutamic acid, aspartic acid. In some embodiments, a conservative amino acid substitution refers to an amino acid substitution that does not alter the relative charge or size characteristics of the protein in which the amino acid substitution was made.

As used herein, a "fusion protein" refers to a protein created through the joining of two or more originally separate proteins, or portions thereof. In some embodiments, a linker or spacer will be present between each protein.

As used herein, the term "heterologous," in reference to polypeptide domains, refers to the fact that the polypeptide domains do not naturally occur together (e.g., in the same polypeptide). For example, in fusion proteins generated by the hand of man, a polypeptide domain from one polypeptide may be fused to a polypeptide domain from a different polypeptide. The two polypeptide domains would be considered "heterologous" with respect to each other, as they do not naturally occur together.

As used herein, the term "host cell" is a cell that is manipulated according to the present invention, e.g., into which nucleic acids are introduced. A "transformed host cell" is a cell that has undergone transformation such that it has taken up exogenous material such as exogenous genetic material, e.g., exogenous nucleic acids.

As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. The comparison of sequences and determination of percent identity between two sequences can be accomplished using a mathematical algorithm. As is well known in the art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999.

The term "library", as used herein in the context of polynucleotides, refers to a population of two or more different polynucleotides. In some embodiments, a library comprises at least two polynucleotides comprising different sequences encoding nucleases and/or at least two polynucleotides comprising different sequences encoding guide RNAs. In some embodiments, a library comprises at least $10^1$, at least $10^2$, at least 10, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$ different polynucleotides. In some embodiments, the members of the library may comprise randomized sequences, for example, fully or partially randomized sequences. In some embodiments, the library comprises polynucleotides that are unrelated to each other, e.g., nucleic acids comprising fully randomized sequences. In other embodiments, at least some members of the library may be related, for example, they may be variants or derivatives of a particular sequence.

As used herein, the term "operably linked" refers to a juxtaposition wherein the components described are in a relationship permitting them to function in their intended manner. A regulatory element "operably linked" to a functional element is associated in such a way that expression and/or activity of the functional element is achieved under conditions compatible with the regulatory element. In some embodiments, "operably linked" regulatory elements are contiguous (e.g., covalently linked) with the coding elements of interest; in some embodiments, regulatory elements act in trans to or otherwise at a from the functional element of interest.

As used herein, the term "nuclease" refers to a polypeptide capable of cleaving the phosphodiester bonds between the nucleotide subunits of nucleic acids; the term "endonuclease" refers to a polypeptide capable of cleaving the phosphodiester bond within a polynucleotide chain.

As used herein, the terms "nucleic acid", "nucleic acid molecule" or "polynucleotide" are used herein interchangeably. They refer to a polymer of deoxyribonucleotides or ribonucleotides in either single- or double-stranded form, and unless otherwise stated, encompass known analogs of natural nucleotides that can function in a similar manner as naturally occurring nucleotides. The terms encompass nucleic acid-like structures with synthetic backbones, as well as amplification products. DNAs and RNAs are both polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

As used herein, the term "oligonucleotide" refers to a string of nucleotides or analogues thereof. Oligonucleotides may be obtained by a number of methods including, for example, chemical synthesis, restriction enzyme digestion or PCR. As will be appreciated by one skilled in the art, the length of an oligonucleotide (i.e., the number of nucleotides) can vary widely, often depending on the intended function or use of the oligonucleotide. Throughout the specification, whenever an oligonucleotide is represented by a sequence of letters (chosen from the four base letters: A, C, G, and T, which denote adenosine, cytidine, guanosine, and thymidine, respectively), the nucleotides are presented in the 5' to 3' order from the left to the right. In certain embodiments, the sequence of an oligonucleotide includes one or more degenerate residues described herein.

As used herein, the term "off-target" refers to binding, cleavage and/or editing of an unintended or unexpected region of DNA by an RNA guided nuclease. In some embodiments, a region of DNA is an off-target region when it differs from the region of DNA intended or expected to be bound, cleaved and/or edited by 1, 2, 3, 4, 5, 6, 7 or more nucleotides.

As used herein, the term "on-target" refers to binding, cleavage and/or editing of an intended or expected region of DNA by an RNA guided nuclease.

As used herein, the term "polypeptide" generally has its art-recognized meaning of a polymer of amino acids. The term is also used to refer to specific functional classes of polypeptides, such as, for example, nucleases, antibodies, etc.

As used herein, the term "regulatory element" refers to a DNA sequence that controls or impacts one or more aspects of gene expression. In some embodiments, a regulatory element is or includes a promoter, an enhancer, a silencer, and/or a termination signal. In some embodiments, a regulatory element controls or impacts inducible expression.

As used herein, the term "target site" refers to a nucleic acid sequence that defines a portion of a nucleic acid to which a binding molecule will bind, provided sufficient conditions for binding exist. In some embodiments, a target site is a nucleic acid sequence to which a nuclease described herein binds and/or that is cleaved by such nuclease. In some embodiments, a target site is a nucleic acid sequence to which a guide RNA described herein binds. A target site may be single-stranded or double-stranded. In the context of nucleases that dimerize, for example, nucleases comprising a FokI DNA cleavage domain, a target site typically comprises a left-half site (bound by one monomer of the nuclease), a right-half site (bound by the second monomer of the nuclease), and a spacer sequence between the half sites in which the cut is made. In some embodiments, the left-half site and/or the right-half site is between 10-18 nucleotides long. In some embodiments, either or both half-sites are shorter or longer. In some embodiments, the left and right half sites comprise different nucleic acid sequences. In the context of zinc finger nucleases, target sites may, in some embodiments, comprise two half-sites that are each 6-18 bp long flanking a non-specified spacer region that is 4-8 bp long. In the context of TALENs, target sites may, in some embodiments, comprise two half-sites sites that are each 10-23 bp long flanking a non-specified spacer region that is 10-30 bp long. In the context of RNA-guided (e.g., RNA-programmable) nucleases, a target site typically comprises a nucleotide sequence that is complementary to a guide RNA of the RNA-programmable nuclease, and a protospacer adjacent motif (PAM) at the 3' end or 5' end adjacent to the guide RNA-complementary sequence. For the RNA-guided nuclease Cas9, the target site may be, in some embodiments, 16-24 base pairs plus a 3-6 base pair PAM (e.g., NNN, wherein N represents any nucleotide). Exemplary target sites for RNA-guided nucleases, such as Cas9, are known to those of skill in the art and include, without limitation, NNG, NGN, NAG, NGA, NGG, NGAG and NGCG wherein N represents any nucleotide. In addition, Cas9 nucleases from different species (e.g., *S. thermophilus* instead of *S. pyogenes*) recognizes a PAM that comprises the sequence NGGNG. Additional PAM sequences are known, including, but not limited to NNAGAAW and NAAR (see, e.g., Esvelt and Wang, Molecular Systems Biology, 9:641 (2013), the entire contents of which are incorporated herein by reference). For example, the target site of an RNA-guided nuclease, such as, e.g., Cas9, may comprise the structure [Nz]-[PAM], where each N is, independently, any nucleotide, and z is an integer between 1 and 50. In some embodiments, z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, Z is 20.

As used herein, the term "variant" refers to an entity that shows significant structural identity with a reference entity (e.g., a wild-type sequence) but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a polypeptide may have a characteristic sequence element comprising a plurality of amino acids having designated positions relative to one another in linear or three-dimensional space and/or contributing to a particular biological function; a nucleic acid may have a characteristic sequence element comprising a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide (e.g., a nuclease described herein) that is at least 60%, 65%, 70%, 75%, 80%, 85%, 86%, 87%, 88%, 89%, 90%, 91%, 92%, 93%, 94%, 95%, 96%, 97%, 98% or 99%. Alternatively or additionally, in some embodiments, a variant polypeptide does not share at least one characteristic sequence element with a reference polypeptide. In some embodiments, the reference polypeptide has one or more biological activities.

In some embodiments, a variant polypeptide shares one or more of the biological activities of the reference polypeptide, e.g., nuclease activity. In some embodiments, a variant polypeptide lacks one or more of the biological activities of the reference polypeptide. In some embodiments, a variant polypeptide shows a reduced level of one or more biological activities (e.g., nuclease activity, e.g., off-target nuclease activity) as compared with the reference polypeptide. In some embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). In some embodiments, a variant has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature.

Overview

The present disclosure encompasses, in part, the discovery of RNA-guided nucleases that exhibit improved specificity for targeting a DNA sequence, e.g., relative to a wild-type nuclease. Provided herein are such RNA-guided nuclease variants, compositions and systems that include such nuclease variants, as well as methods of producing and methods of using such nuclease variants, e.g., to edit one or more target nucleic acids.

RNA-Guided Nucleases

RNA-guided nucleases according to the present disclosure include, but are not limited to, naturally-occurring Class 2 CRISPR nucleases such as Cas9, and Cpf1, as well as other nucleases derived or obtained therefrom. For example, other nucleases derived or obtained therefrom include variant nucleases. In some embodiments, a variant nuclease comprises one or more altered enzymatic properties, e.g., altered nuclease activity or altered helicase activity (as compared with a naturally occurring or other reference nuclease molecule (including a nuclease molecule that has already been engineered or altered)). In some embodiments, a variant nuclease can have nickase activity or no cleavage activity (as opposed to double strand nuclease activity). In another embodiment, variant nucleases have an alteration that alters its size, e.g., a deletion of amino acid sequence that reduces its size, e.g., with or without significant effect on one or more, or any nuclease activity. In another embodiment, a variant nuclease can recognize a different PAM sequence. In some embodiments, a different PAM sequence is a PAM sequence other than that recognized by the endogenous wild-type PI domain of the reference nuclease, e.g., a non-canonical sequence.

In functional terms, RNA-guided nucleases are defined as those nucleases that: (a) interact with (e.g., complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g., Cas9 vs. Cpf1), species (e.g., S. pyogenes vs. S. aureus) or variation (e.g., full-length vs. truncated or split; naturally-occurring PAM specificity vs. engineered PAM specificity, etc.) of RNA-guided nuclease.

The PAM sequence takes its name from its sequential relationship to the "protospacer" sequence that is complementary to gRNA targeting domains (or "spacers"). Together with protospacer sequences, PAM sequences define target regions or sequences for specific RNA-guided nuclease/gRNA combinations.

Various RNA-guided nucleases may require different sequential relationships between PAMs and protospacers. In general, Cas9s recognize PAM sequences that are 3' of the protospacer as visualized relative to the guide RNA targeting domain.

Cpf1, on the other hand, generally recognizes PAM sequences that are 5' of the protospacer.

In addition to recognizing specific sequential orientations of PAMs and protospacers, RNA-guided nucleases can also recognize specific PAM sequences. S. aureus Cas9, for instance, recognizes a PAM sequence of NNGRRT or NNGRRV, wherein the N residues are immediately 3' of the region recognized by the gRNA targeting domain. S. pyogenes Cas9 recognizes NGG PAM sequences. And F. novicida Cpf1 recognizes a TTN PAM sequence. PAM sequences have been identified for a variety of RNA-guided nucleases, and a strategy for identifying novel PAM sequences has been described by Shmakov et al., 2015, *Molecular Cell* 60, 385-397, Nov. 5, 2015. It should also be noted that engineered RNA-guided nucleases can have PAM specificities that differ from the PAM specificities of reference molecules (for instance, in the case of an engineered RNA-guided nuclease, the reference molecule may be the naturally occurring variant from which the RNA-guided nuclease is derived, or the naturally occurring variant having the greatest amino acid sequence homology to the engineered RNA-guided nuclease).

In addition to their PAM specificity, RNA-guided nucleases can be characterized by their DNA cleavage activity: naturally-occurring RNA-guided nucleases typically form DSBs in target nucleic acids, but engineered variants have been produced that generate only SSBs (discussed above) Ran & Hsu, et al., *Cell* 154(6), 1380-1389, Sep. 12, 2013 ("Ran"), incorporated by reference herein), or that that do not cut at all.

Cas9

Crystal structures have been determined for S. pyogenes Cas9 (Jinek et al., *Science* 343(6176), 1247997, 2014 ("Jinek 2014"), and for S. aureus Cas9 in complex with a unimolecular guide RNA and a target DNA (Nishimasu 2014; Anders et al., *Nature*. 2014 Sep. 25; 513(7519):569-73 ("Anders 2014"); and Nishimasu 2015).

A naturally occurring Cas9 protein comprises two lobes: a recognition (REC) lobe and a nuclease (NUC) lobe; each of which comprise particular structural and/or functional domains. The REC lobe comprises an arginine-rich bridge helix (BH) domain, and at least one REC domain (e.g., a REC1 domain and, optionally, a REC2 domain). The REC lobe does not share structural similarity with other known proteins, indicating that it is a unique functional domain. While not wishing to be bound by any theory, mutational analyses suggest specific functional roles for the BH and REC domains: the BH domain appears to play a role in gRNA:DNA recognition, while the REC domain is thought to interact with the repeat:anti-repeat duplex of the gRNA and to mediate the formation of the Cas9/gRNA complex.

The NUC lobe comprises a RuvC domain, an HNH domain, and a PAM-interacting (PI) domain. The RuvC domain shares structural similarity to retroviral integrase superfamily members and cleaves the non-complementary (i.e., bottom) strand of the target nucleic acid. It may be formed from two or more split RuvC motifs (such as RuvC I, RuvCII, and RuvCIII in S. pyogenes and S. aureus). The HNH domain, meanwhile, is structurally similar to HNN endonuclease motifs, and cleaves the complementary (i.e., top) strand of the target nucleic acid. The PI domain, as its name suggests, contributes to PAM specificity.

While certain functions of Cas9 are linked to (but not necessarily fully determined by) the specific domains set forth above, these and other functions may be mediated or influenced by other Cas9 domains, or by multiple domains on either lobe. For instance, in S. pyogenes Cas9, as described in Nishimasu 2014, the repeat:antirepeat duplex of the gRNA falls into a groove between the REC and NUC lobes, and nucleotides in the duplex interact with amino acids in the BH, PI, and REC domains. Some nucleotides in the first stem loop structure also interact with amino acids in multiple domains (PI, BH and REC), as do some nucleotides in the second and third stem loops (RuvC and PI domains).

Variant Cas9 Nucleases

The disclosure includes variant RNA-guided nucleases that have an increased level of specificity for their targets, e.g., relative to a wild-type nuclease. For example, variant RNA-guided nucleases of the disclosure exhibit an increased level of on-target binding, editing and/or cleavage activity, relative to a wild-type nuclease. Additionally or alternatively, variant RNA-guided nucleases of the disclosure exhibit a decreased level of off-target binding, editing and/or cleavage activity, relative to a wild-type nuclease.

Variant nucleases described herein include variants of S. pyogenes Cas9 and Neisseria meningitidis (N. meningitidis) (SEQ ID NO: 14). The amino acid sequence of wild-type S. pyogenes Cas9 is provided as SEQ ID NO: 13. A variant nuclease can comprise a substitution of an amino acid, relative to a wild-type nuclease, at a single position or at multiple positions, such as at 2, 3, 4, 5, 6, 7, 8, 9, 10 or more positions. In some embodiments, a variant nuclease comprises an amino acid sequence at least 70%, 75%, 80%, 85%, 90%, 95%, 96%, 97%, 98% or 99% identical to a wild-type nuclease.

One or more wild-type amino acids can be substituted by an alanine. Additionally or alternatively, one or more wild-type amino acids can be substituted by a conservative variant amino acid. Additionally or alternatively, one or more wild-type amino acids can be substituted by a non-conservative variant amino acid.

For example, a variant nuclease described herein can comprise a substitution, relative to wild-type nuclease (e.g., SEQ ID NO: 13), at one, two, three, four, five, six, seven, or all eight of the following positions: D23, D1251, Y128, T67, N497, R661, Q695 and/or Q926 (e.g., an alanine, conservative, and/or non-conservative substitution at one or all of these positions). Exemplary variant nucleases can comprise one, two, three, four, five, six, seven, or all eight of the following substitutions, relative to wild-type nuclease: D23A, D1251G, Y128V, T67L, N497A, R661 A, Q695A and/or Q926A. A particular nuclease variant of the disclosure comprises the following substitutions, relative to wild-type nuclease: D23A, D1251G, Y128V, and T67L.

In some embodiments, a variant nuclease comprises an amino acid sequence that is at least 70%, 75%, 80%, 85%, 90%, 95%, 96%, 97%, 98% or 99% identical to SEQ ID NO:13, and that includes one, two, three, four, five, six, seven, or all eight of the following substitutions: D23A, D1251G, Y128V, T67L, N497A, R661 A, Q695A and/or Q926A. For example, a variant nuclease can comprise an amino acid sequence that is at least 70%, 75%, 80%, 85%, 90%, 95%, 96%, 97%, 98% or 99% identical to SEQ ID NO:13, and that includes the following substitutions: D23A, D1251G, Y128V, and T67L.

In addition to a substitution at one, two, three, four, five, six, seven, or all eight of D23, D1251, Y128, T67, N497, R661, Q695 and/or Q926 (e.g., D23A, D1251G, Y128V, and T67L), an S. pyogenes Cas9 variant can also include a substitution at one or more of the following positions: L169; Y450; M495; W659; M694; H698; A728; E1108; V1015; R71; Y72; R78; R165; R403; T404; F405; K1107; S1109; R1114; S1116; K1118; D1135; S1136; K1200; S1216; E1219; R1333; R1335; T1337; Y72; R75; K76; L101; S104; F105; R115; H116; I135; H160; K163; Y325; H328; R340; F351; D364; Q402; R403; I1110; K1113; R1122; Y1131; R63; R66; R70; R71; R74; R78; R403; T404; N407; R447; I448; Y450; K510; Y515; R661; V1009; Y1013; K30; K33; N46; R40; K44; E57; T62; R69; N77; L455; S460; R467; T472; I473; H721; K742; K1097; V1100; I1102; F1105; K1123; K1124; E1225; Q1272; H1349; S1351; and/or Y1356, e.g., a substitution described in U.S. Pat. No. 9,512,446.

In some embodiments, an S. pyogenes variant can include a substitution at one or more of the following positions: N692, K810, K1003, R1060 and G1218. In some embodiments, an S. pyogenes variant includes one or more of the following substitutions: N692A, K810A, K1003A, R1060A and G1218R.

Table 1 sets out exemplary S. pyogenes Cas9 mutants comprising 3 to 5 substitutions according to certain embodiments of this disclosure. For clarity, this disclosure encompasses Cas9 variant proteins having mutations at 1, 2, 3, 4, 5 or more of the sites set forth above and elsewhere in this disclosure. Exemplary triple, quadruple, quintuple mutants are presented in Table 1 and described, for example, in Chen et al., Nature 550:407-410 (2017); Slaymaker et al. Science 351:84-88 (2015); Kleinstiver et al., Nature 529:490-495; Kleinstiver et al., Nature 523:481-485 (2015); Kleinstiver et al., Nature Biotechnology 33:1293-1298 (2015).

TABLE 1

| Positions |
| --- |
| D1135V/R1335Q/T1337R |
| D1135E/R1335Q/T1337R |
| D1135V/G1218R/R1335E/T1337R |
| N497A/R661A/Q695A/Q926A |
| D1135E/N497A/R661A/Q695A/Q926A |
| N497A/R661A/Q695A/Q926A/L169A |
| N497A/R661A/Q695A/Q926A/Y450A |

TABLE 1-continued

Positions

K810A/K1003A/R1060A
K848A/K1003A/R1060A
N692A/M694A/Q695A/H698A

An *S. pyogenes* Cas9 variant can also include one or more amino acid substitutions that reduce or destroy the nuclease activity of the Cas9: D10, E762, D839, H983, or D986 and H840 or N863. For example, the *S. pyogenes* Cas9 may include amino acid substitutions D10A/D10N and H840A/H840N/H840Y, to render the nuclease portion of the protein catalytically inactive. Substitutions at these positions could be an alanine, or other residues, e.g., glutamine, asparagine, tyrosine, serine, or aspartate, e.g., E762Q, H983N, H983Y, D986N, N863D, N863S, or N863H (Nishimasu et al., *Cell* 156, 935-949 (2014); WO 2014/152432). In some embodiments, the variant includes a single amino acid substitution at D10A or H840A which creates a single-strand nickase enzyme. In some embodiments, the variant polypeptide includes amino acid substitutions at D10A and H840A which inactivates the nuclease activity (e.g., known as dead Cas9 or dCas9). Variant nucleases described herein also include variants of *Neisseria meningitidis* (*N. meningitidis*) (Hou et al., PNAS Early Edition 2013, 1-6; incorporated herein by reference). The amino acid sequence of wild-type *N. meningitidis* Cas9 is provided as SEQ ID NO: 14). Comparision of the *N. meningitidis* and *S. pyogenes* Cas9 sequences indicates that certain regions are conserved (see WO 2015/161276). Accordingly, the disclosure includes *N. meningitidis* Cas9 variants that include one or more of the substitutions described herein in the context of *S. pyogenes* Cas9, e.g., at one or more corresponding amino acid positions of *N. meningitidis* Cas9. For example, substitutions at *N. meningitidis* amino acid positions D29, D983, L101, S66, Q421, E459, Y671 which correspond to *S. pyogenes* amino acid positions D23, D1251, Y128, T67, R661, Q695 and/or Q926, respectively (FIG. 17).

A variant *N. meningitidis* nuclease can comprise a substitution of an amino acid, relative to a wild-type nuclease, at a single position or at multiple positions, such as at 2, 3, 4, 5, 6, 7, 8, 9, 10 or more positions. In some embodiments, a variant *N. meningitidis* nuclease comprises an amino acid sequence at least 70%, 75%, 80%, 85%, 90%, 95%, 96%, 97%, 98% or 99% identical to a wild-type nuclease.

Variant nucleases retain one or more functional activities of a wild-type nuclease, e.g., ability to cleave double stranded DNA, ability to cleave a single strand of DNA (e.g., a nickase), ability to target DNA without cleaving the DNA (e.g., dead nuclease), and/or ability to interact with a guide nucleic acid. In some embodiments, a variant nuclease has the same or about the same level of on-target activity as a wild-type nuclease. In some embodiments, a variant nuclease has one or more functional activities that are improved relative to a wild-type nuclease. For example, a variant nuclease described herein can exhibit an increased level of on-target activity (e.g., 10%, 20%, 30%, 40%, 50%, 60%, 70%, 80%, 90%, 100%, 125%, 150%, 175%, 200% or higher, relative to wild-type) and/or a decreased level of off-target activity (e.g., 90%, 80%, 70%, 60%, 50%, 40%, 30%, 20%, 10%, or 5% of wild-type activity). In some embodiments, when a variant nuclease described herein is contacted with double stranded DNA (dsDNA) (e.g., a target dsDNA), off-target editing (e.g., rate of off-target editing) is less than the observed or measured rate of off-target editing of the target dsDNA by a wild-type nuclease. For example, the rate of off-target editing by a variant nuclease can be about 5%, 10%, 15%, 20%, 25%, 30%, 40%, 50%, 60%, 70%, 80%, 90%, or 95% less than that of a wild-type nuclease.

Activity of a variant nuclease (e.g., on-target and/or off-target activity) can be assessed using any method known in the art, such as GUIDE-seq (see, e.g., Tsai et al. (Nat. Biotechnol. 33:187-197 (2015)); CIRCLE-seq (see, e.g., Tsai et al., Nature Methods 14:607-614 (2017)); Digenome-seq (see, e.g., Kim et al., Nature Methods 12:237-243 (2015)); or ChIP-seq (see, e.g., O'Geen et al., Nucleic Acids Res. 43:3389-3404 (2015)). In some embodiments, rate of off-target editing is assessed by determining the % of indels at an off-target site.

As is well known by one of ordinary skill in the art, various methods exist for introduction of substitutions into an amino acid sequence of a polypeptide. Nucleic acids encoding variant nucleases can be introduced into a viral or a non-viral vector for expression in a host cells (e.g., human cell, animal cell, bacterial cell, yeast cell, insect cell). In some embodiments, nucleic acids encoding variant nucleases are operably linked to one or more regulatory domains for expression of the nuclease. As it will be appreciated by one of ordinary skill in the art, suitable bacterial and eukaryotic promoters are well known in the art and described in e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Paiva et al., 1983, *Gene* 22:229-235).

Cpf1

The crystal structure of Acidaminococcus sp. Cpf1 in complex with crRNA and a double-stranded (ds) DNA target including a TTTN PAM sequence has been solved by Yamano et al. (Cell. 2016 May 5; 165(4): 949-962 ("Yamano"), incorporated by reference herein). Cpf1, like Cas9, has two lobes: a REC (recognition) lobe, and a NUC (nuclease) lobe. The REC lobe includes REC1 and REC2 domains, which lack similarity to any known protein structures. The NUC lobe, meanwhile, includes three RuvC domains (RuvC-I, -II and -III) and a BH domain. However, in contrast to Cas9, the Cpf1 REC lobe lacks an HNH domain, and includes other domains that also lack similarity to known protein structures: a structurally unique PI domain, three Wedge (WED) domains (WED-I, —II and —III), and a nuclease (Nuc) domain.

While Cas9 and Cpf1 share similarities in structure and function, it should be appreciated that certain Cpf1 activities are mediated by structural domains that are not analogous to any Cas9 domains. For instance, cleavage of the complementary strand of the target DNA appears to be mediated by the Nuc domain, which differs sequentially and spatially from the HNH domain of Cas9. Additionally, the non-targeting portion of Cpf1 gRNA (the handle) adopts a pseudoknot structure, rather than a stem loop structure formed by the repeat:antirepeat duplex in Cas9 gRNAs.

Nucleic Acids Encoding RNA-Guided Nucleases

Nucleic acids encoding RNA-guided nucleases, e.g., Cas9, Cpf1 or functional fragments thereof, are provided herein. Exemplary nucleic acids encoding RNA-guided nucleases have been described previously (see, e.g., Cong et al., Science. 2013 Feb. 15; 339(6121):819-23 ("Cong 2013"); Wang et al., PLoS One. 2013 Dec. 31; 8(12):e85650 ("Wang 2013"); Mali 2013; Jinek 2012).

In some cases, a nucleic acid encoding an RNA-guided nuclease can be a synthetic nucleic acid sequence. For example, the synthetic nucleic acid molecule can be chemically modified. In certain embodiments, an mRNA encoding an RNA-guided nuclease will have one or more (e.g., all) of the following properties: it can be capped; polyadenylated; and substituted with 5-methylcytidine and/or pseudouridine.

Synthetic nucleic acid sequences can also be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein. Examples of codon optimized Cas9 coding sequences are presented in WO 2016/073990 ("Cotta-Ramusino").

In addition, or alternatively, a nucleic acid encoding an RNA-guided nuclease may comprise a nuclear localization sequence (NLS). Nuclear localization sequences are known in the art.

Guide RNA (gRNA) Molecules

The terms "guide RNA" and "gRNA" refer to any nucleic acid that promotes the specific association (or "targeting") of an RNA-guided nuclease such as a Cas9 or a Cpf1 to a target sequence such as a genomic or episomal sequence in a cell. gRNAs can be unimolecular (comprising a single RNA molecule, and referred to alternatively as chimeric), or modular (comprising more than one, and typically two, separate RNA molecules, such as a crRNA and a tracrRNA, which are usually associated with one another, for instance by duplexing). gRNAs and their component parts are described throughout the literature, for instance in Briner et al. (Molecular Cell 56(2), 333-339, Oct. 23, 2014 ("Briner"), which is incorporated by reference), and in Cotta-Ramusino.

In bacteria and archea, type II CRISPR systems generally comprise an RNA-guided nuclease protein such as Cas9, a CRISPR RNA (crRNA) that includes a 5' region that is complementary to a foreign sequence, and a trans-activating crRNA (tracrRNA) that includes a 5' region that is complementary to, and forms a duplex with, a 3' region of the crRNA. While not intending to be bound by any theory, it is thought that this duplex facilitates the formation of—and is necessary for the activity of—the Cas9/gRNA complex. As type II CRISPR systems were adapted for use in gene editing, it was discovered that the crRNA and tracrRNA could be joined into a single unimolecular or chimeric guide RNA, in one non-limiting example, by means of a four nucleotide (e.g., GAAA) "tetraloop" or "linker" sequence bridging complementary regions of the crRNA (at its 3' end) and the tracrRNA (at its 5' end). (Mali et al. Science. 2013 Feb. 15; 339(6121): 823-826 ("Mali 2013"); Jiang et al. Nat Biotechnol. 2013 March; 31(3): 233-239 ("Jiang"); and Jinek et al., 2012 Science August 17; 337(6096): 816-821 ("Jinek 2012"), all of which are incorporated by reference herein.)

Guide RNAs, whether unimolecular or modular, include a "targeting domain" that is fully or partially complementary to a target domain within a target sequence, such as a DNA sequence in the genome of a cell where editing is desired. Targeting domains are referred to by various names in the literature, including without limitation "guide sequences" (Hsu et al., Nat Biotechnol. 2013 September; 31(9): 827-832, ("Hsu"), incorporated by reference herein), "complementarity regions" (Cotta-Ramusino), "spacers" (Briner) and generically as "crRNAs" (Jiang). Irrespective of the names they are given, targeting domains are typically 10-30 nucleotides in length, and in certain embodiments are 16-24 nucleotides in length (for instance, 16, 17, 18, 19, 20, 21, 22, 23 or 24 nucleotides in length), and are at or near the 5' terminus of in the case of a Cas9 gRNA, and at or near the 3' terminus in the case of a Cpf1 gRNA.

In addition to the targeting domains, gRNAs typically (but not necessarily, as discussed below) include a plurality of domains that may influence the formation or activity of gRNA/Cas9 complexes. For instance, as mentioned above, the duplexed structure formed by first and secondary complementarity domains of a gRNA (also referred to as a repeat:anti-repeat duplex) interacts with the recognition (REC) lobe of Cas9 and can mediate the formation of Cas9/gRNA complexes. (Nishimasu et al., Cell 156, 935-949, Feb. 27, 2014 ("Nishimasu 2014") and Nishimasu et al., Cell 162, 1113-1126, Aug. 27, 2015 ("Nishimasu 2015"), both incorporated by reference herein). It should be noted that the first and/or second complementarity domains may contain one or more poly-A tracts, which can be recognized by RNA polymerases as a termination signal. The sequence of the first and second complementarity domains are, therefore, optionally modified to eliminate these tracts and promote the complete in vitro transcription of gRNAs, for instance through the use of A-G swaps as described in Briner, or A-U swaps. These and other similar modifications to the first and second complementarity domains are within the scope of the present disclosure.

Along with the first and second complementarity domains, Cas9 gRNAs typically include two or more additional duplexed regions that are involved in nuclease activity in vivo but not necessarily in vitro. (Nishimasu 2015). A first stem-loop one near the 3' portion of the second complementarity domain is referred to variously as the "proximal domain," (Cotta-Ramusino) "stem loop 1" (Nishimasu 2014 and 2015) and the "nexus" (Briner). One or more additional stem loop structures are generally present near the 3' end of the gRNA, with the number varying by species: *S. pyogenes* gRNAs typically include two 3' stem loops (for a total of four stem loop structures including the repeat:anti-repeat duplex), while *S. aureus* and other species have only one (for a total of three stem loop structures). A description of conserved stem loop structures (and gRNA structures more generally) organized by species is provided in Briner.

While the foregoing description has focused on gRNAs for use with Cas9, it should be appreciated that other RNA-guided nucleases have been (or may in the future be) discovered or invented which utilize gRNAs that differ in some ways from those described to this point. For instance, Cpf1 ("CRISPR from *Prevotella* and Franciscella 1") is a recently discovered RNA-guided nuclease that does not require a tracrRNA to function. (Zetsche et al., 2015, Cell 163, 759-771 Oct. 22, 2015 ("Zetsche I"), incorporated by reference herein). A gRNA for use in a Cpf1 genome editing system generally includes a targeting domain and a complementarity domain (alternately referred to as a "handle"). It should also be noted that, in gRNAs for use with Cpf1, the targeting domain is usually present at or near the 3' end, rather than the 5' end as described above in connection with Cas9 gRNAs (the handle is at or near the 5' end of a Cpf1 gRNA).

Those of skill in the art will appreciate, however, that although structural differences may exist between gRNAs from different prokaryotic species, or between Cpf1 and Cas9 gRNAs, the principles by which gRNAs operate are generally consistent. Because of this consistency of operation, gRNAs can be defined, in broad terms, by their targeting domain sequences, and skilled artisans will appreciate that a given targeting domain sequence can be incorporated in any suitable gRNA, including a unimolecular or chimeric gRNA, or a gRNA that includes one or more chemical modifications and/or sequential modifications (substitutions, additional nucleotides, truncations, etc.). Thus, for economy of presentation in this disclosure, gRNAs may be described solely in terms of their targeting domain sequences.

More generally, skilled artisans will appreciate that some aspects of the present disclosure relate to systems, methods and compositions that can be implemented using multiple RNA-guided nucleases. For this reason, unless otherwise specified, the term gRNA should be understood to encompass any suitable gRNA that can be used with any RNA-guided nuclease, and not only those gRNAs that are compatible with a particular species of Cas9 or Cpf1. By way of illustration, the term gRNA can, in certain embodiments, include a gRNA for use with any RNA-guided nuclease occurring in a Class 2 CRISPR system, such as a type II or type V or CRISPR system, or an RNA-guided nuclease derived or adapted therefrom.

Selection Methods

The present disclosure also provides a competitive-based selection strategy that would select for the variants (e.g., among a library of variants/mutants) having the greatest fitness in a set of conditions. Selection methods of the present invention are useful, for example, in directed evolution strategies, e.g., strategies that involve one or more rounds of mutagenesis followed by selection. In certain embodiments, presently disclosed methods allow a higher throughput directed evolution strategy than is typically observed with current polypeptide and/or polypeptide evolution strategies.

Selection Based on Binding to a DNA Target Site in a Phagemid

In one aspect, the present disclosure provides methods of selecting for a version of a polypeptide or polynucleotide of interest based on whether it binds a DNA target site. These methods generally comprise steps of (a) providing a library of polynucleotides, wherein different polynucleotides in the library encode different versions of the polypeptide of interest or serve as templates for different versions of the polynucleotide of interest; (b) introducing the library of polynucleotides into host cells so that each transformed host cell includes a polynucleotide that encodes a version of the polypeptide of interest or serves as a template for a version of the polynucleotide of interest; (c) providing a plurality of bacteriophage comprising a phagemid that encodes a first selection agent and includes a DNA target site; (d) incubating transformed host cells from step (b) together with the plurality of bacteriophage under culture conditions such that the plurality of bacteriophage infect the transformed host cells, wherein expression of the first selection agent confers a survival advantage or disadvantage in infected host cells; and (e) selecting for host cells that exhibit a survival advantage (e.g., a survival advantage described herein) in (d). For example, survival of step (d) is based on various schemes as outlined below.

Binding at the DNA target site decreases expression of a selection agent (as further discussed herein) encoded by or contained on the phagemid. As discussed further herein, the selection agent may confer a survival disadvantage or a survival advantage. A decrease in the expression of the selection agent can occur by transcriptional repression of the selection agent mediated by binding at the DNA target site. In some embodiments, a decrease in the expression of the selection agent occurs by cleavage of the phagemid at or near the DNA target site. For example, the polypeptide or polynucleotide of interest can both bind to and cleave DNA.

Some classes of enzymes bind to a particular DNA recognition site and cleave the DNA at or near the binding site. Accordingly, the site of DNA cleavage can be the same or different than the DNA binding site. In some embodiments in which the DNA cleavage site is different than the DNA binding site, the two sites are near one another (e.g., within 20, 15, 10, or 5 base pairs). Additionally or alternatively, the two sites are not within 20, 15, 10, or 5 base pairs of one another.

When cleavage is involved, it may be cleavage of one strand (also referred to as "nicking") or both strands of the phagemid, which, as discussed below, replicates as double-stranded plasmid when inside host cells.

In certain embodiments, binding at the DNA target site increases expression of a selection agent encoded by the phagemid or whose template is on the phagemid. An increase in the expression of the selection agent can occur, e.g., by transcriptional activation of the selection agent mediated by binding at the DNA target site.

Versions of polypeptides or polynucleotides that bind to the DNA target site can be selected, e.g., in that host cells that were transformed with such versions exhibit a maintenance of cell growth kinetics, an increase in cell growth kinetics (e.g., an increase in cell division), and/or reversal of a decrease in cell growth kinetics (e.g., at least a partial rescue from a decrease in cell growth kinetics; while host cells that were transformed with versions that do not bind the DNA target site do not exhibit an increase in cell growth kinetics (e.g., exhibit a decrease in cell growth kinetics and/or cell division) and/or are killed. In certain embodiments, versions of polypeptides or polynucleotides that bind to the DNA target site are selected in that host cells that were transformed with such versions survive, while host cells that were transformed with versions that do not bind the DNA target site do not survive.

Versions of polypeptides or polynucleotides that do not bind to the DNA target site can be selected, e.g., in that host cells that were transformed with such versions exhibit a maintenance of cell growth kinetics, an increase in cell growth kinetics (e.g., an increase in cell division), and/or reversal of a decrease in cell growth kinetics (e.g., at least a partial rescue from a decrease in cell growth kinetics; while host cells that were transformed with versions that bind the DNA target site do not exhibit an increase in cell growth kinetics (e.g., exhibit a decrease in cell growth kinetics and/or cell division) and/or are killed. In certain embodiments, versions of polypeptides or polynucleotides that do not bind to the DNA target site are selected in that host cells that were transformed with such versions survive, while host cells that were transformed with versions that bind the DNA target site do not survive.

Figure 16:
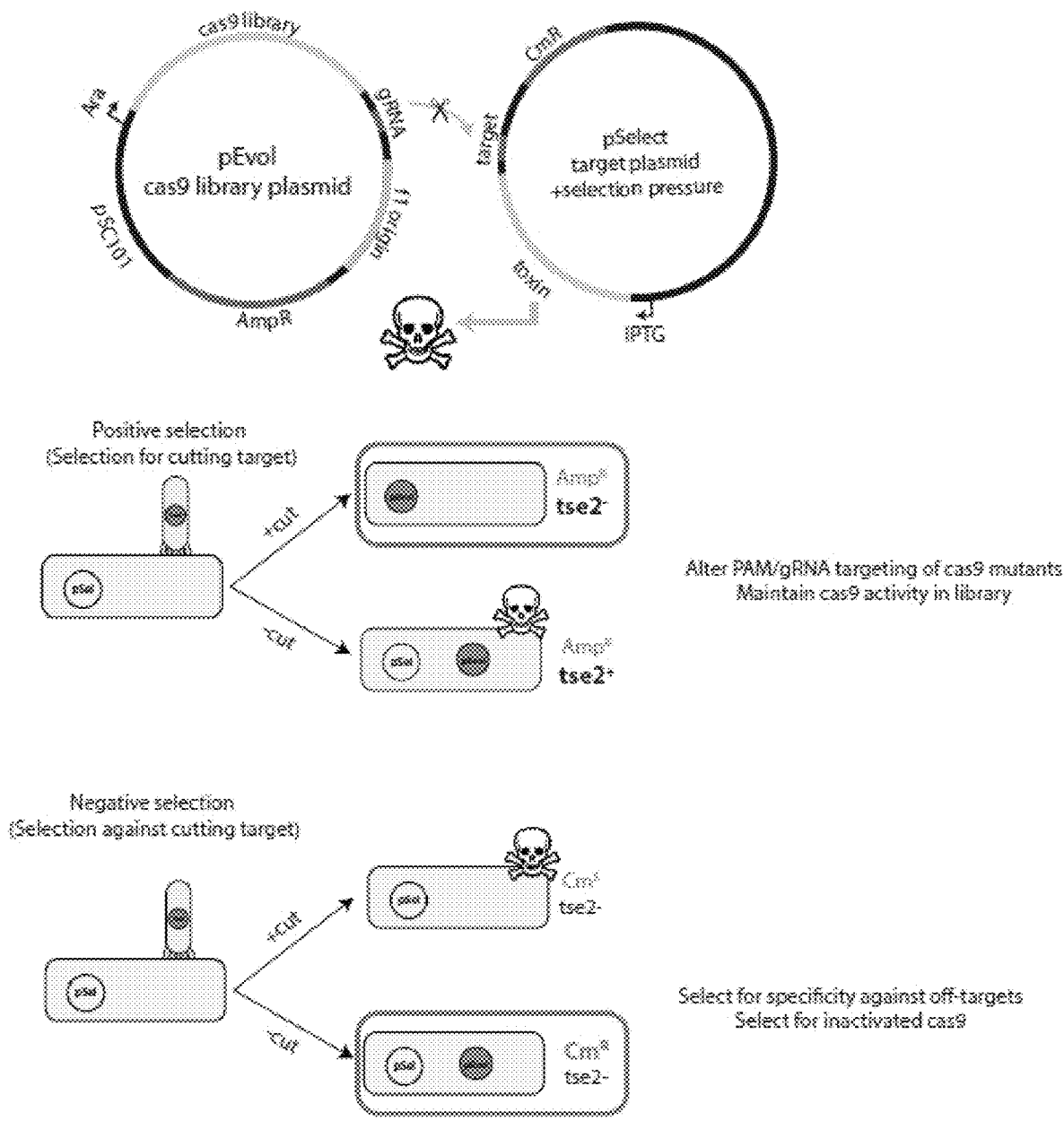
FIG. 16 shows a schematic outlining an evolutionary strategy for selecting against nucleases that show activity at known off-target sites. Phagemid libraries of Cas9 mutants were generated by mutagenesis followed by a round of positive selection for on-target cleavage, which is followed by a round of negative selection for off-target cleavage.

In an alternative embodiment, a phagemid, (e.g., pEvol_CAS), encoding a Cas9 protein and a gRNA targeting a target sequence along with a phage origin F1 element can be constructed (FIG. 16). In some embodiments, the phagemid constitutively expresses beta-lactamase, which confer resistance to ampicillin (AmpR), or a similar antibiotic such as carbecillin, and an inducible arabinose promoter (Ara) to control expression of Cas9. In some embodiments, a pEvol_CAS can be packaged into helper bacteriophage for introduction into transformed host cells. Plasmids, for example pSelect_MUT and pSelect_WT can also be constructed, each containing a potential target site. Alternatively, or additionally these plasmids may also contain a constitutively expressed chloramphenicol resistance gene (CmR) and a bacterial toxin under the control of lac promoter, allowing induction of toxin expression by, for example, IPTG (Isopropyl β-D-1-thiogalactopyranoside).

To engineer allele specificity, phagemid libraries of Cas9 mutants can be generated using, for example, a pEvol_CAS phagemid as the initial template for mutagenesis, and a comprehensive and unbiased mutagenesis method that targets every codon and allows tuning of the mutation rate.

Alternatively or additionally, in some embodiments, each round of evolution comprises subjecting a phagemid library of pEvol_CAS mutants to positive selection for cutting against *E. coli* containing, for example, pSelect_MUT or pSelect_WT in a competitive culture. For example, bacteria containing pSelect_MUT or pSelect_WT can be infected using phage packaging pEvol_CAS mutants and the bacteria can be cultured in ampicillin in a liquid culture.

In some embodiments, after an initial incubation and infection, the stringency of positive selection using a toxin can be assessed by adding, for example, IPTG, to induce toxin expression. In some embodiments, expression of Cas9 and guide RNA can be induced by addition of arabinose. During positive selection, bacteria can be continuously infected by phage present in the liquid culture, thus presenting a continuous challenge to cut the target.

In some embodiments, after an initial incubation and infection, the stringency of negative selection using an antibiotic, e.g., chloramphenicol. In some embodiments, expression of Cas9 and guide RNA can be induced by addition arabinose. During negative selection, bacteria can be continuously infected by phage present in the liquid culture, thus presenting the continuous challenge to not cut the target.

In another aspect, these methods generally comprise steps of (a) providing a polynucleotide that encodes a first selection agent and includes a DNA target site; (b) introducing the polynucleotides into host cells so that each transformed host cell includes a polynucleotide that encodes the first selection agent and the DNA target site; (c) providing a plurality of bacteriophage comprising phagemid that encodes a library of polynucleotides, wherein different polynucleotides in the library encode different versions of the polypeptide of interest or serve as templates for different versions of the polynucleotide of interest; (d) incubating transformed host cells from step (b) together with the plurality of bacteriophage under culture conditions such that the plurality of bacteriophage infect the transformed host cells, wherein expression of the first selection agent confers a survival advantage or disadvantage in infected host cells; and (e) selecting for host cells that exhibit a survival advantage (e.g., a survival advantage described herein) in (d). For example, survival of step (d) is based on various schemes as outlined above.

Selection Based on Binding at the DNA Target Site when Binding Decreases Expression of a Disadvantageous Selection Agent In certain embodiments, the selection agent confers a survival disadvantage (e.g., a decrease in cell growth kinetics (e.g., a growth delay) and/or an inhibition of cell division) in host cells and/or kills the host cells, and binding at the DNA target site decreases expression of the selection agent. Survival is then based on binding at the DNA target site: host cells that were transformed with a polynucleotide from the library that encodes a version of the polypeptide of interest, or that serves as a template for a version of the polynucleotide of interest, that binds to the DNA target site exhibit a maintenance of cell growth kinetics, an increase in cell growth kinetics (e.g., an increase in cell division), and/or reversal of a decrease in cell growth kinetics (e.g., at least a partial rescue from a decrease in cell growth kinetics). Meanwhile, host cells that were transformed with a polynucleotide from the library that encodes a version of the polypeptide of interest, or that serves as a template for a version of the polynucleotide of interest, that does not bind to the DNA target site exhibit a survival disadvantage (e.g., a decrease in cell growth kinetics (e.g., a growth delay) and/or an inhibition of cell division), do not survive and/or are killed).

In some embodiments, expression of the selection agent is decreased by cleaving the phagemid at or near the DNA target site, e.g., by cleaving one strand ("nicking") or both strands of the phagemid.

Polynucleotides in the library can include, e.g., an antibiotic resistance gene, and the selection agent (encoded by the phagemid or whose template is on the phagemid) inhibits a product of the antibiotic resistance gene. Culture conditions during such selection can include, e.g., exposure to the antibiotic to which the antibiotic resistance gene provides resistance. In one example, the antibiotic resistance gene encodes beta lactamase, the antibiotic is ampicillin or penicillin or another beta-lactam antibiotic, and the selection agent is beta lactamase inhibitory protein (BLIP).

Selection Based on Lack of Binding at the DNA Target Site when Binding would Decrease Expression of an Advantageous Selection Agent In certain embodiments, the selection agent confers a survival advantage (e.g., a maintenance of cell growth kinetics, an increase in cell growth kinetics (e.g., an increase in cell division), and/or reversal of a decrease in cell growth kinetics (e.g., at least a partial rescue from a decrease in cell growth kinetics), in host cells, and binding at the DNA target site decreases expression of the selection agent. Survival is then based on a lack of binding at the DNA target site: host cells that were transformed with a polynucleotide from the library that encodes a version of the polypeptide of interest, or that serves as a template for a version of the polynucleotide of interest, that does not bind to the DNA target site exhibit a maintenance of cell growth kinetics, an increase in cell growth kinetics (e.g., an increase in cell division), and/or reversal of a decrease in cell growth kinetics (e.g., at least a partial rescue from a decrease in cell growth kinetics). Meanwhile, host cells that were transformed with a polynucleotide form the library that encodes a version of the polypeptide of interest, or that serves as a template for a version of the polynucleotide of interest, that binds to the DNA target site exhibit a survival disadvantage (e.g., a decrease in cell growth kinetics (e.g., a growth delay), an inhibition of cell division, do not survive and/or are killed).

In some embodiments, expression of the selection agent is decreased by cleaving the phagemid at or near the DNA target site, e.g., by cleaving one strand ("nicking") or both strands of the phagemid.

Selection Based on Binding at the DNA Target Site when Binding Increases Expression of an Advantageous Selection Agent In certain embodiments, the selection agent confers a survival advantage (e.g., a maintenance of cell growth kinetics, an increase in cell growth kinetics, (e.g., an increase in cell division), and/or reversal of a decrease in cell growth kinetics (e.g., at least a partial rescue from a decrease in cell growth kinetics) in host cells, and binding at the DNA target site increases expression of the selection agent. Survival is then based on binding at the DNA target site: host cells that were transformed with a polynucleotide from the library that encodes a version of the polypeptide of interest, or that serves as a template for a version of the polynucleotide of interest, that binds to the DNA target site exhibit a maintenance of cell growth kinetics, an increase in cell growth kinetics (e.g., an increase in cell division), and/or reversal of a decrease in cell growth kinetics (e.g., at least a partial rescue from a decrease in cell growth kinetics). Meanwhile, host cells that were transformed with a polynucleotide form the library that encodes a version of the polypeptide of interest, or that serves as a template for a version of the polynucleotide of interest, that does not bind to the DNA target site exhibit a survival disadvantage (e.g., a decrease in cell growth kinetics (e.g., a growth delay), an inhibition of cell division, do not survive and/or are killed).

Selection Based on Lack of Binding at the DNA Target Site when Binding would Increase Expression of an Disadvantageous Selection Agent In certain embodiments, the selection agent confers a survival disadvantage (e.g., a decrease in cell growth kinetics (e.g., a growth delay) and/or an inhibition of cell division) in host cells and/or kills the host cells, and binding at the DNA target site increases expression of the selection agent. Survival is then based on a lack of binding at the DNA target site: host cells that were transformed with a polynucleotide from the library that encodes a version of the polypeptide of interest, or that serves as a template for a version of the polynucleotide of interest, that does not bind to the DNA target site exhibit a maintenance of cell growth kinetics, an increase in cell growth kinetics (e.g., an increase in cell division), and/or reversal of a decrease in cell growth kinetics (e.g., at least a partial rescue from a decrease in cell growth kinetics). Meanwhile, host cells that were transformed with a polynucleotide form the library that encodes a version of the polypeptide of interest, or that serves as a template for a version of the polynucleotide of interest, that binds to the DNA target site exhibit a survival disadvantage (e.g., a decrease in cell growth kinetics (e.g., a growth delay), an inhibition of cell division, do not survive and/or are killed).

Selection Based on Binding to a DNA Target Site in the Host Cell Genome in the Presence of a Selection Agent In one aspect, the present disclosure provides methods of selecting for a version of a polypeptide or polynucleotide of interest based on whether it binds to a DNA target site in the presence of a selection agent.

As discussed further herein, these methods generally comprise steps of: (a) providing a library of polynucleotides, wherein different polynucleotides in the library encode different versions of the polypeptide or polynucleotide of interest; (b) introducing the library of polynucleotides into host cells so that each transformed host cell includes a polynucleotide that encodes a version of the polypeptide or polynucleotide of interest, wherein the host cell genome includes a DNA target site; (c) providing a plurality of bacteriophage comprising a phagemid that encodes a first selection agent, wherein the first selection agent is a first selection polynucleotide; (d) incubating transformed host cells from step (b) together with the plurality of bacteriophage under culture conditions such that the plurality of bacteriophage infect the transformed host cells, wherein binding of the DNA target site in the presence of the first selection agent confers a survival advantage or disadvantage in infected host cells; and (e) selecting for host cells that survive step (d).

Survival of step (d) is based on various schemes as outlined below.

The DNA target site can be, e.g., in the host cell genome. Additionally or alternatively, the DNA target site can be in an essential survival gene of the host cell. In Additionally or alternatively, the DNA target site can be in a gene whose product prevents a survival gene from being expressed.

In some embodiments, the selection polynucleotide is a guide RNA for a CRISPR-associated (Cas) nuclease.

Survival Based on Lack of Binding at the DNA Target Site when Binding would be Disadvantageous In certain embodiments, binding at the DNA target site in the host cell in the presence of the selection agent (which is a polynucleotide) is disadvantageous (e.g., because binding at the DNA target site results in disruption of an essential survival gene in the host cell). Survival is then based on a lack of binding at the DNA target site: host cells that were transformed with a polynucleotide from the library that encodes a version of the polypeptide of interest, or that serves as a template for a version of the polynucleotide of interest, that does not bind to the DNA target site survive. Meanwhile, host cells that were transformed with a polynucleotide form the library that encodes a version of the polypeptide of interest, or that serves as a template for a version of the polynucleotide of interest, that binds to the DNA target site do not survive.

Survival Binding at the DNA Target Site when Binding would be Advantageous

In certain embodiments, binding at the DNA target site in the host cell in the presence of the selection agent (which is a polynucleotide) is advantageous (e.g., because binding at the DNA target site results expression of a survival gene in the host cell). Survival is then based on binding at the DNA target site: host cells that were transformed with a polynucleotide from the library that encodes a version of the polypeptide of interest, or that serves as a template for a version of the polynucleotide of interest, that binds to the DNA target site survive. Meanwhile, host cells that were transformed with a polynucleotide form the library that encodes a version of the polypeptide of interest, or that serves as a template for a version of the polynucleotide of interest, that does not bind to the DNA target site do not survive.

Selection Based on Induction of Expression of a Polypeptide

In one aspect, the present disclosure provides methods of selecting for a version of a polypeptide or polynucleotide of interest based on modulating or controlling the expression of the polypeptide.

As discussed further herein, these methods generally comprise steps of (a) providing a library of polynucleotides, wherein different polynucleotides in the library encode different versions of the polypeptide of interest or serve as templates for different versions of the polynucleotide of interest; (b) introducing the library of polynucleotides into host cells so that each transformed host cell includes a polynucleotide that encodes a version of the polypeptide of interest or serves as a template for a version of the polynucleotide of interest; (c) inducing expression of the polypeptide to control the amount of polypeptide that is present in the culture; (d) providing a plurality of bacteriophage comprising a phagemid that encodes a first selection agent and includes a DNA target site; (e) incubating transformed host cells from step (b) together with the plurality of bacteriophage under culture conditions such that the plurality of bacteriophage infect the transformed host cells, wherein expression of the first selection agent confers a survival advantage or disadvantage in infected host cells; and (f) selecting for host cells that survive step (d). Survival of step (d) is based on various schemes described herein.

The polynucleotide can include an inducible promoter, e.g., an inducible promoter described herein, and expression is induced by contacting the polynucleotide with one or more induction agents described herein. For example, a polynucleotide can include an arabinose promoter, and expression from the polynucleotide can be induced by contacting the polynucleotide with arabinose. In another example, a polynucleotide can include a tac promoter, and expression from the polynucleotide can be induced by contacting the polynucleotide with IPTG. In yet another example, a polynucleotide can include a rhaBAD promoter, and expression from the polynucleotide can be induced by contacting the polynucleotide with rhamnose.

Libraries of Polynucleotides

Methods of the present disclosure can start, e.g., with a step of providing a library of polynucleotides (such as a plasmid library), in which different polynucleotides in the library encode different versions of polypeptide of interest (or, in the case of a polynucleotide of interest, the library includes different versions of a polynucleotide of interest and/or different versions of a polynucleotide of interest that serve as a template for different versions of the polynucleotide of interest).

A library described herein can include, e.g., polynucleotides operably linked to an inducible promoter. For example, induction of a promoter can induce expression of a polypeptide encoded by a polynucleotide. In some embodiments, induction of a promoter to induce expression of a polypeptide encoded by a polynucleotide affects efficiency of a selection method. For example, efficiency of a selection method can be improved and/or increased relative to efficiency of a selection method that does not use an inducible promoter.

Such libraries may be obtained, e.g., by using or purchasing an existing library, such as one that is commercially available and/or available through public collections. Alternatively or additionally, the library may be obtained from a mutagenesis method. For example, the library can be obtained by a random mutagenesis method or a comprehensive mutagenesis method, e.g., a method that randomly targets a polynucleotide throughout an entire pre-defined target region for mutagenesis.

A library can also be obtained by a targeted mutagenesis method. For example, a subregion of the polynucleotide of interest, or of the polypeptide of interest, can be targeted for mutagenesis. Additionally or alternatively, the entire polynucleotide of interest, or the entire polypeptide of interest, can be targeted for mutagenesis.

Although polypeptides or polynucleotides of interest typically have DNA-binding ability, it is expected that not all versions of the polypeptide or polynucleotide of interest encoded by the different polynucleotides in the library would necessarily be able to bind DNA. Furthermore, among those versions of polypeptide or polynucleotide of interest encoded by the different polynucleotides in the library, it is expected that they may have differing abilities to bind DNA. Indeed, selection methods of the present disclosure involve distinguishing between versions of the polypeptide or polynucleotide of interest that can and cannot bind to a DNA target site. In certain embodiments, many or even most of the versions of the polypeptide or polynucleotide of interest do not bind to DNA.

Similarly, in embodiments in which the polypeptide or polynucleotide of interest can cleave DNA, not all of the versions of the polypeptide or polynucleotide of interest can necessarily cleave DNA.

Host Cells

Methods of the present disclosure can comprise, after the step of providing a library of polynucleotides, introducing the library of polynucleotides into host cells, so that each transformed host cell includes a polynucleotide that encodes a version of the polypeptide of interest or serves as a template for a version of the polynucleotide of interest.

Host cells generally refer cells that can take up exogenous materials, e.g., nucleic acids (such as DNA and RNA), polypeptides, or ribonuclear proteins. Host cells can be, e.g., single cell organisms, such as, e.g., microorganisms, or eukaryotic cells, e.g., yeast cells, mammalian cells (e.g., in culture) etc.

In some embodiments, host cells are prokaryotic cells, e.g., bacterial cells, e.g., *E. coli* bacteria. Bacterial cells can be Gram-negative or Gram-positive and can belong to the Bacteria (formerly called Eubacteria) domain or the Archaea (formerly called Archaebacteria) domain. Any of these types of bacteria may be suitable as host cells so long as they can be grown in a laboratory setting and can take up exogenous materials.

The host cells can be bacterial cells that are competent or made competent, e.g., in that they are able or made to be able to take up exogenous material such as genetic material.

There a variety of mechanisms by which exogenous materials such as genetic material can be introduced into host cells. For example, in bacteria, there are three general mechanisms, classified as transformation (uptake and incorporation of extracellular nucleic acids such as DNA), transduction (e.g., transfer of genetic material from one cell to another by a plasmid or by a virus that infects the cells, like bacteriophage), and conjugation (direct transfer of nucleic acids between two cells that are temporarily joined). Host cells into which genetic material have been introduced by transformation are generally referred to as "transformed host cells."

In some embodiments, the library of polynucleotides is introduced into host cells by transformation. Protocols for transforming host cells are known in the art. For bacterial cells, for example, there are methods based on electroporation, methods based in lipofection, methods based on heat shock, methods based on agitation with glass beads, methods based on chemical transformation, methods based on bombardment with particles coated with exogenous material (such as DNA or RNA, etc. One of ordinary skill in the art will be able to choose a method based on the art and/or protocols provided by manufacturers of the host cells.

Transformed host cells, e.g., can each contain a polynucleotide that encodes a version of the polypeptide of interest or serves as a template for a version of polynucleotide of interest.

A library of polynucleotides can be introduced into a population of host cells such that the population of transformed host cells collectively contain all members of the library. That is, for every version of polynucleotide in the library, at least one host cell in the population contains that version of the polynucleotide, such that all versions of the polynucleotide in the library are represented in the population of transformed host cells.

Bacteriophage

Methods of the present disclosure can comprise, after the step introducing the library of polynucleotides into host cells, providing a plurality of bacteriophage comprising a phagemid that encodes a first selection agent and includes a DNA target site.

Bacteriophage are viruses that infect bacteria and inject their genomes (and/or any phagemids packaged within the bacteriophage) into the cytoplasm of the bacteria. Generally, bacteriophage replicate within the bacteria, though replication-defective bacteriophage exist.

In some embodiments, a plurality of bacteriophage comprising a phagemid as described herein is incubated together with transformed host cells under conditions that allow the bacteriophage to infect the transformed host cells. The bacteriophage can be replication-competent, e.g., the bacteriophage replicate within the transformed host cells, and the replicated viral particles are released as virions in the culture medium, allowing re-infection of other host cells by bacteriophage.

Virions can be released from the host cells without lysing the host cells.

In some embodiments, the plurality of bacteriophage continuously infects (infects and re-infects) transformed host cells, thereby presenting a continuous challenge to the host cell.

The bacteriophage can be "helper phage" in that they preferentially package phagemid over phage DNA. For example, the bacteriophage can preferentially package phagemid over phage DNA by a factor of at least 3:1, at least 4:1, at least 5:1, at least 6:1, at least 7:1, at least 8:1, at least 9:1, or at least 10:1.

In some embodiments, the bacteriophage do not generally lyse their host cells, e.g., the bacteriophage do not lyse their host cells under the conditions in which the transformed host cells are incubated together with the plurality of bacteriophage.

The bacteriophage can be filamentous bacteriophage. Filamentous bacteriophage usually infect Gram-negative bacteria (which include, among other things, *E. coli, P aeruginosa, N. gonorrhoeae,* and *Y. pestis*) and have a genome of single-stranded DNA.

For example, the filamentous bacteriophage can be Ff phage, which infect *E. coli* that carry the F episome. Examples of such phage include, but are not limited to, M13 bacteriophage, fl phage, fd phage, and derivatives and variants thereof.

Additionally or alternatively, the bacteriophage can be an M13 bacteriophage or a derivative or variant thereof, e.g., the bacteriophage can be M13KO7, a derivative of M13 that has a kanamycin resistance marker and a p15A origin of replication. M13KO7 has been characterized has having a high phagemid versus phage packing ratio of approximately 10:1, thereby serving as a useful helper phage.

Additionally or alternatively, the bacteriophage can be VCSM13, a derivative of M13KO7.

The bacteriophage can also be an fl bacteriophage or a derivative or variant thereof. For example, the bacteriophage can be R408, a derivative of fl that does not have any antibiotic selection marker.

Additionally or alternatively, the bacteriophage can be CM13, a derivative of M13KO7 that has been reported to produce virions more reliably than M13KO7.

Pools of bacteriophage containing different phagemids can also used in methods of the disclosure. For example, as discussed further herein, different off-site targets can be presented on different phagemids contained in the same pool of bacteriophage when it is desired, for example, to select against binding and/or cleaving at more than one off-target site.

Phagemids

Phagemids are circular plasmids that have an fl origin of replication from an fl phage, and therefore can be replicated as a plasmid and packaged as single-stranded DNA by bacteriophage. Phagemids also contain an origin of replication for double-stranded replication (e.g., while inside a host cell).

Phagemids suitable for use in the present invention generally encode, or serve as a template for, a selection agent and comprise a DNA target site. Thus, phagemids for use in the present invention typically comprise a regulatory element operably linked to, and driving expression of, a gene element encoding, or serving as a template for, the selection agent.

As noted above, the DNA target site can be included anywhere within the phagemid. For example, the DNA target site can be located within the regulatory element, within the gene element, outside of and distal to both the regulatory element and the gene element, or outside of both elements but near at least one of the elements.

The position of the DNA target site may depend on the embodiment. For example, the DNA target site can be located within the regulatory element. This positioning may be suitable, for example, in embodiments in which the polypeptide of interest is a transcription factor, e.g., a transcriptional activator or repressor, and selection is based on whether or not the transcription factor binds to the DNA target site.

There is no restriction on where the DNA target site may be located, in that binding of the polypeptide of interest anywhere within the phagemid will increase or decrease expression of the selection agent. For example, binding of the polypeptide of interest at the DNA target site can result in cleaving of the phagemid at or near the DNA target site. Cleavage of the phagemid anywhere within the phagemid would cause linearization of the phagemid, which would result in the phagemid not being replicated within the host cell, therefore abrogating expression of the selection agent.

Phagemids can be packaged into bacteriophage using methods known in the art, including protocols provided by manufacturers of the bacteriophage. For example, a commonly used protocol is to make a double-stranded plasmid version of the desired phagemid construct, transform the double-stranded plasmid into host cells such as bacteria, and then inoculate a culture of such transformed host cells with helper bacteriophage, which may package the double-stranded plasmid as a single-stranded phagemid.

Culture Conditions

Methods of the present disclosure can comprise, after the step of providing a plurality of bacteriophage comprising a phagemid that encodes a first selection agent and includes a DNA target site, a step of incubating transformed host cells (into which the library of polynucleotides was introduced) together with a plurality of bacteriophage under culture conditions such that the plurality of bacteriophage infect the transformed host cells. Generally, these conditions are conditions in which expression of the first selection agent confers either a survival disadvantage or a survival advantage, depending on the embodiment.

In certain embodiments, the culture conditions are competitive culture conditions. "Competitive culture conditions" refers to conditions in which a population of organisms (e.g., host cells) is grown together and must compete for the same limited resources, for example, nutrients, oxygen, etc.

Host cells can be incubated in an environment in which there is no or little input of new nutrients. For example, host cells can be incubated in an environment in which there is no or little input of new oxygen, e.g., in sealed containers such as flasks.

Additionally or alternatively, host cells can be incubated in an culture medium that is well-mixed throughout the period of incubation, e.g., a shaking liquid culture. Generally, under such well-mixed conditions, the host cells have similar nutritional requirements and will be in competition for nutrients and/or oxygen (in the case of aerobic organisms) as the nutrients and/or oxygen become depleted by the growing population.

Additionally or alternatively, host cells can be incubated at an approximately constant temperature, e.g., at a temperature most suitable for the type of host cell. For example, for certain bacterial species including E. coli, host cells are typically incubated at a temperature that is around 37° C. In some embodiments, the host cells are incubated within 5° C., 4° C., 3° C., 2° C., or 1° C. of 37° C., e.g., at approximately 37° C.

Host cells can be incubated in a liquid culture that is shaken. This shaking is typically vigorous enough to prevent uneven distribution of nutrients and/or settling of some host cells at the bottom of the culture. For example, host cells can be shaken at least 100 rpm (rotations per minute), at least 125 rpm, at least 150 rpm, at least 175 rpm, at least 200 rpm, at least 225 rpm, at least 250 rpm, at least 275 rpm, or at least 300 rpm. In some embodiments, host cells are shaken at between 100 rpm and 400 μm, e.g., between 200 and 350 rpm, e.g., at approximately 300 rpm.

Host cells can be incubated for a period of time before the plurality of bacteriophage is introduced into the culture. This period of time can allow, for example, the host cell population to recover from being in storage and/or to reach a particular ideal density before introduction of the plurality of bacteriophage. During this period of time before the plurality of bacteriophage is introduced, a selection pressure may be used, or it may not be used.

Culture conditions can comprise, e.g., continuous incubation of the host cells together with the bacteriophage over a period of time, e.g., at least 4 hours, at least 8 hours, at least 12 hours, or at least 16 hours. Additionally or alternatively, culture conditions can comprise continuous incubation of the host cells together with the bacteriophage until the growth of the host cells is saturated.

Culture conditions can allow continuous infection of the host cells by bacteriophage. That is, host cells are infect and re-infected continuously (if they survive) during the incubation period.

Additionally or alternatively, a selection pressure is introduced into the culture. For example, in particular with host cells transformed with exogenous DNA (such as plasmids), a selection pressure can be introduced to favor those host cells that maintain the exogenous DNA. Commonly used schemes include using one or more antibiotics as the selection pressure and a corresponding antibiotic resistance gene in the exogenous DNA that is to be maintained. This selection pressure may be the same as or different than that involving the selection agent as discussed herein, and, in some embodiments, both are used, e.g., sequentially and/or simultaneously.

In some embodiments, for at least a period of time during which transformed host cells are incubated together with bacteriophage, culture conditions include exposure to one or more antibiotics, to which some host cells may have resistance by virtue of an antibiotic resistance gene present on the phagemid, the polynucleotide in the library, or both. For example, both the phagemid and the polynucleotide in the library can have antibiotic resistance genes, e.g., the antibiotic resistance gene can be the same or different. If the phagemid contains one antibiotic resistance gene (a "first antibiotic resistance gene" conferring resistance to a "first antibiotic") and the polynucleotide contains another antibiotic resistance gene (a "second antibiotic resistance gene" conferring resistance to a "second antibiotic"), culture conditions can comprise any of various schemes. As non-limiting examples, these conditions can comprise: 1) simultaneous exposure to both of the first antibiotic and the second antibiotic; 2) sequential exposure to the second antibiotic for a period of time (e.g., during a time period in which the host cells are incubated before bacteriophage are introduced into the culture), followed by exposure to either i) the first antibiotic or ii) both the first antibiotic and the second antibiotic (e.g., during a time period in which the host cells are incubated together with the bacteriophage); or 3) exposure to only one of the relevant antibiotics (e.g., the first antibiotic) during the course of the incubation.

Selection Agents

Methods described herein can comprise a step of providing a plurality of bacteriophage comprising a phagemid encoding or serving as a template for a selection agent. Depending on the embodiment, the selection agent can confer either a survival advantage or a survival disadvantage to the host cell in the conditions in which the host cells are incubated with the bacteriophage. The selection agent can confer either an increase in cell growth kinetics or a decrease in cell growth kinetics to the host cell in the conditions in which the host cells are incubated with the bacteriophage.

The selection agent can be, e.g., a polypeptide and/or a polynucleotide.

In some embodiments, the selection agent confers a survival advantage to the host cell.

In some embodiments, the selection agent is encoded by a gene that is essential for survival of the host cell. Examples of such essential survival genes include, but are not limited to, genes involved in fatty acid biosynthesis; genes involved in amino acid biosynthesis; genes involved in cell division; genes involved in global regulatory functions; genes involved in protein translation and/or modification; genes involved in transcription; genes involved in protein degradation; genes encoding heat shock proteins; genes involved in ATP transport; genes involved in peptidoglycan synthesis; genes involved in DNA replication, repair, and/or modification; genes involved in tRNA modification and/or synthesis; and genes encoding ribosome components and/or involved in ribosome synthesis). For example, in *Escherichia coli*, a number of essential survival genes are known in the art, including, but not limited to, accD (acetylCoA carboxylase, carboxytransferase component, beta subunit), acpS (CoA:apo-[acyl-carrier-protein] pantetheinephosphotransferase), asd (aspartate-semialdehyde dehydrogenase), dapE (N-succinyl-diaminopimelate deacylase), dnaJ (chaperone with DnaK; heat shock protein), dnaK (chaperone Hsp70), era (GTP-binding protein), frr (ribosome releasing factor), ftsI (septum formation; penicillin-binding protein 3; peptidoglycan synthetase), ftsL cell division protein; ingrowth of wall at septum); ftsN (essential cell division protein); ftsZ (cell division; forms circumferential ring; tubulin-like GTP-binding protein and GTPase), gcpE, grpE (phage lambda replication; host DNA synthesis; heat shock protein; protein repair), hflB (degrades sigma32, integral membrane peptidase, cell division protein), infA (protein chain initiation factor IF-1), lgt (phosphatidylglycerol prolipoprotein diacylglyceryl transferase; a major membrane phospholipid), 1pxC (UDP-3-O-acyl N-acetylglucosamine deacetylase; lipid A biosynthesis), map (methionine aminopeptidase), mopA (GroEL, chaperone Hsp60, peptide-dependent ATPase, heat shock protein), mopB (GroES, 10 Kd chaperone binds to Hsp60 in pres. Mg-ATP, suppressing its ATPase activity), msbA ATP-binding transport protein; multicopy suppressor of htrB), murA (first step in murein biosynthesis; UDP-N-glucosamine 1-carboxyvinyltransferase), murI (glutamate racemase, required for biosynthesis of D-glutamate and peptidoglycan), nadE (NAD synthetase, prefers NH3 over glutamine), nusG (component in transcription antitermination), parC (DNA topoisomerase IV subunit A), ppa (inorganic pyrophosphatase), proS (proline tRNA synthetase), pyrB (aspartate carbamoyltransferase, catalytic subunit), rpsB (30S ribosomal subunit protein S2), trmA (tRNA (uracil-5-)-methyltransferase), ycaH, ycfB, yfiL, ygjD (putative O-sialoglycoprotein endopeptidase), yhbZ (putative GTP-binding factor), yihA, and yjeQ. Additional essential genes in E. coli include those listed in "Experimental Determination and System-Level Analysis of Essential Genes in E. coli MG1655" by Gerdes 2003, e.g., in Supplementary Tables 1, 2, and 6.

In some embodiments, the selection agent is encoded by an antibiotic resistance gene, as discussed further below. For example, culture conditions can include exposure to the antibiotic to which the antibiotic resistance gene provides resistance.

In some embodiments, the selection agent inhibits a gene product that confers a survival disadvantage.

In certain embodiments, the selection agent confers a survival disadvantage to the host cell. The selection agent can be toxic to the host cell. For example, the selection agent can be a toxin, many of which are known in the art and many of which have been identified in various bacterial species. Examples of such toxins include, but are not limited to, ccdB, FlmA, fst, HicA, Hok, Ibs, Kid, LdrD, MazF, ParE, SymE, Tisb, TxpABrnT, XCV2162, yafO, Zeta and tse2. For example, the selection agent can be ccdB, which is found in E. coli. In other examples, the selection agent is tse2.

The selection agent can be toxic because it produces a toxic substance. For example, the production of the toxic substance can occur only in the presence of another agent, the presence of which may or may not be controlled externally.

Additionally or alternatively, the selection agent can inhibit a gene product that confers a survival advantage. By way of non-limiting example, the selection agent could be beta-lactamase inhibitory protein (BLIP), which inhibits beta-lactamases such as ampicillin and penicillin, among others.

Induction Agents

Methods described herein can comprise a step of providing a library of polynucleotides, in which different polynucleotides in the library encode different versions of polypeptide of interest (or, in the case of a polynucleotide of interest, serve as a template for different version of the polynucleotide of interest). A polynucleotide can include, e.g., a regulatory element, e.g., promoter, which can control expression of the polypeptide. A regulatory element can be an inducible promoter, and expression can be induced by an induction agent. Such induction agent and/or induced expression can increase or improve the efficiency of selection.

The induction agent can be a polypeptide and/or a polynucleotide. The induction agent can also be a small molecule, light, temperature or an intracellular metabolite.

In some embodiments, the induction agents is arabinose, anhydrotetracycline, lactose, IPTG, propionate, blue light (470 nm) red light (650 nm), green light (532 nm) or L-rhamnose. For example, the induction agent can be arabinose.

Libraries of Polynucleotides Encoding Different Versions of a Cas9 Molecule

In some embodiments, methods and compositions of the present invention can be used with a library of polynucleotides that encode different versions of a Cas9 molecule or Cas9 polypeptide (e.g., a comprehensive and unbiased library of Cas9 mutants that span all or a portion of a Cas9 molecule or Cas9 polypeptide). In certain embodiments, methods and compositions of the present invention can be used to select one or more members of the library based on a particular property. In a typical embodiment, a Cas9 molecule or Cas9 polypeptide has the ability to interact with a gRNA molecule and, in concert with the gRNA molecule, localize to a site in a nucleic acid. Other activities, e.g., PAM specificity, cleavage activity, or helicase activity can vary more widely in Cas9 molecules and Cas9 polypeptides.

In some embodiments, methods and compositions of the present invention can be used to select one or more versions of a Cas9 molecule or Cas9 polypeptide which comprise altered enzymatic properties, e.g., altered nuclease activity or altered helicase activity (as compared with a naturally occurring or other reference Cas9 molecule including a Cas9 molecule that has already been engineered or altered). As discussed herein, a mutated version of a reference Cas9 molecule or Cas9 polypeptide can have nickase activity or no cleavage activity (as opposed to double strand nuclease activity). In an embodiment, methods and compositions of the present invention can be used to select one or more versions of a Cas9 molecule or Cas9 polypeptide which have an alteration that alters its size, e.g., a deletion of amino acid sequence that reduces its size, e.g., with or without significant effect on one or more, or any Cas9 activity. In an embodiment, methods and compositions of the present invention can be used to select one or more versions of a Cas9 molecule or Cas9 polypeptide which recognizes a different PAM sequence (e.g., a version of a Cas9 molecule can be selected to recognize a PAM sequence other than that recognized by the endogenous wild-type PI domain of the reference Cas9 molecule).

Libraries with different versions of a Cas9 molecule or Cas9 polypeptide can be prepared using any method, e.g., by alteration of a parental, e.g., naturally occurring, Cas9 molecules or Cas9 polypeptides, to provide a library of altered Cas9 molecules or Cas9 polypeptides. For example, one or more mutations or differences relative to a parental Cas9 molecule, e.g., a naturally occurring or engineered Cas9 molecule, can be introduced. Such mutations and differences comprise: substitutions (e.g., conservative substitutions or substitutions of non-essential amino acids); insertions; or deletions. In an embodiment, a Cas9 molecule or Cas9 polypeptide in a library of the present invention can comprise one or more mutations or differences, e.g., at least 1, 2, 3, 4, 5, 10, 15, 20, 30, 40 or 50 mutations but less than 200, 100, or 80 mutations relative to a reference, e.g., a parental, Cas9 molecule.

Libraries of Guide RNA Molecules

In some embodiments, methods and compositions of the present disclosure can be used with a library of guide RNA molecules and/or polynucleotides encoding guide RNA molecules. For example, a library can be provided and/or generated that includes DNA molecules that each encodes a guide RNA having (i) a different targeting domain described herein; (ii) different first and/or secondary complementarity domains described herein; and/or (iii) a different stem loop described herein. As described herein, a library can be introduced into a host cell. In some embodiments, a nucleic acid encoding an RNA-guided nuclease, e.g., a Cas9 molecule or Cas9 polypeptide, is also introduced into the host cell.

In certain embodiments, methods and compositions of the present disclosure can be used to select one or more members of the guide RNA library based on a particular property, such as ability to localize to a site in a nucleic acid and/or to interact with a Cas9 molecule or Cas9 polypeptide and/or to localize a Cas9 molecule or Cas9 polypeptide to a site in a nucleic acid.

Libraries with different versions of a guide RNA can be prepared using any method, e.g., by alteration of a parental, e.g., naturally occurring, guide RNA, to provide a library of altered guide RNAs. For example, one or more mutations or differences relative to a parental guide RNA, e.g., a naturally occurring or engineered guide RNA, can be introduced. Such mutations and differences comprise: substitutions; insertions; or deletions. In some embodiments, a guide RNA in a library of the present disclosure can comprise one or more mutations or differences, e.g., at least 1, 2, 3, 4, 5, 10, 15, 20, 30, 40 or 50 mutations but less than 200, 100, or 80 mutations relative to a reference, e.g., a parental, guide RNA.

DNA Target Sites

In general, the DNA target site for a particular inventive method may depend on the physical location of the DNA target site (e.g., in some aspects the DNA target site may be located on a phagemid while in other aspects the DNA target site may be located within the host cell genome), the nature of the polypeptide or polynucleotide of interest, the nature of the selection process and/or the desired outcome of the selection process. DNA target sites can be located within a variety of types of nucleotide sequences. For example, in some embodiments, the DNA target site may be located within an element that is not transcribed, within an element that encodes a polypeptide or serves as a template for a polynucleotide (e.g., a non-coding RNA), within a regulatory element that controls expression of a polypeptide, etc.

As described herein, in some embodiments, the DNA target site may be located on a phagemid. In some embodiments, the DNA target site may be located on a plasmid. In situations where the selection process relies on cleavage (or non-cleavage) of the phagemid, or plasmid, the DNA target site can be located anywhere on the phagemid, or plasmid, since selection relies on linearization (and subsequent destruction) of the phagemid, or plasmid, which may result from cleavage at any position on the phagemid, or plasmid. In situations where the selection process relies on repression (or activation) of expression of a selection agent, the DNA target site may be located within a regulatory element that drives expression of the selection agent. In some embodiments, the regulatory element may be an inducible regulatory element.

As described herein, in some embodiments, the DNA target site may be located within a host cell genome. In situations where the selection process relies on cleavage of an endogenous gene that is essential for survival of the host cell (an "essential gene"), the DNA target site can, for example, be located within the coding or regulatory elements of the essential gene. In situations where the selection process relies on repression of an essential gene, the DNA target site may be at any location in the host cell genome that leads to repression of the essential gene when bound by the polypeptide of interest (e.g., within a regulatory element of the essential gene, between the promoter and coding region of the essential gene, etc.).

The specific nucleotide sequence of the DNA target site (i.e., separate and apart from whether it is located on a phagemid or within a host cell genome) will generally depend on the nature of the polypeptide of interest, the nature of the selection process and the desired outcome of the selection process. By way of example, when the polypeptide of interest is a reference nuclease (e.g., a meganuclease, TALEN or zinc finger nuclease) that recognizes a first nucleotide sequence and the inventive methods are being used to select for one or more modified versions of the reference nuclease that selectively bind a second nucleotide sequence which differs from the first nucleotide sequence (e.g., at 1, 2, 3, etc. bases) then the inventive methods may involve using a DNA target site which corresponds to the second nucleotide sequence in a positive selection step and a DNA target site which corresponds to the first nucleotide sequence in a negative selection step (i.e., to select for versions of the reference nuclease that bind the second nucleotide sequence but do not bind the first nucleotide sequence).

In the case of Cas molecules (e.g., Cas9 molecules) the DNA target site will be determined in part based on the PAM of the Cas molecule and the sequence of the targeting domain of the gRNA which is used to localize the Cas molecule at the DNA target site. By way of example, when the polypeptide of interest is a reference Cas9 molecule that recognizes a first PAM sequence and the inventive methods are being used to select for one or more modified versions of the reference Cas9 molecule that selectively recognize a second PAM sequence which differs from the first PAM sequence (e.g., at 1, 2, 3, etc. bases) then the inventive methods may involve using a DNA target site which includes the second PAM sequence in a positive selection step and a DNA target site which includes the first PAM sequence in a negative selection step (i.e., to select for versions of the reference Cas9 molecule that recognize the second PAM sequence but do not recognize the first PAM sequence). In both cases the DNA target site will also include a sequence that is complementary to the sequence of the targeting domain of the gRNA which is used to localize the Cas9 molecule at the DNA target site.

In some embodiments, methods provided herein can be used for evaluation of the ability of PAM variants to direct cutting of a target site by an RNA-guided nuclease, e.g., a variant *S. pyogenes* Cas9.

In some embodiments, the library comprises a plurality of nucleic acid templates which further include nucleotide sequences comprising PAM variants adjacent to the target site. In some embodiments, a PAM sequence comprises the sequence NGA, NGAG, NGCG, NNGRRT, NNGRRA or NCCRRC.

Some of the methods provided herein allow for the simultaneous assessment of a plurality of PAM variants for any given target site, and in some embodiments, in combination with a variant *S. pyogenes* Cas9. Accordingly, data obtained from such methods can be used to compile a list of PAM variants that mediate cleaving of a particular target site in combination with wild-type *S. pyogenes* Cas9 or a variant *S. pyogenes* Cas9. In some embodiments, a sequencing method is used to generate quantitative sequencing data, and relative abundance of cleavage of a particular target site mediated by a particular PAM variant can be determined.

Antibiotic Resistance Genes

In certain embodiments, plasmids in the library and/or phagemids comprise an antibiotic resistance gene. In some embodiments, the antibiotic resistance gene confers resistance to an antibiotic that kills or inhibits the growth of bacteria such as *E. coli*. Non-limiting examples of such antibiotics include ampicillin, bleomycin, carbenicillin, chloramphenicol, erythromycin, kanamycin, penicillin, polymyxin B, spectinomycin, streptomycin, and tetracycline. A variety of antibiotic resistance gene cassettes are known and available in the art and/or are commercially available, e.g., as elements in plasmids. For example, there are a number of commercially available plasmids with ampR (ampicillin resistance), bleR (bleomycin resistance), carR (carbenicillin resistance), cmR (chloramphenicol resistance), kanR (kanamycin resistance), and/or tetR (tetracycline resistance) or gene elements. An additional example of an antibiotics resistance gene is beta-lactamase.

In some embodiments, phagemids comprise a first antibiotic resistance gene and plasmids in the library comprise a second antibiotic resistance gene. In some embodiments, the first antibiotic resistance gene is distinct from the second antibiotic resistance gene. For example, in some embodiments, the first antibiotic resistance gene is a cmR (chloramphenicol resistance) gene, and the second antibiotic resistance gene is an ampR (ampicillin resistance) gene.

Regulatory Elements

In certain embodiments, gene elements (such as, for example, those encoding selection agents, antibiotic resistance genes, polypeptide, polynucleotides etc.) are operably linked to regulatory elements to allow expression of one or more other elements, e.g., selection agents, antibiotic resistance genes, polypeptides, polynucleotides etc.

In some embodiments, the phagemid includes a regulatory element that drives expression of one or more gene elements on the phagemid, for example, the selection agent.

In some embodiments, polynucleotides in the library include a regulatory element that drives expression of one or more gene elements on the polynucleotide, for example, the polypeptide or polynucleotide of interest, and, if present, a gene element encoding a selection agent such as an antibiotic resistance gene.

A wide variety of gene regulatory elements exist. The type of regulatory element used can depend, for example, on the host cell, the type of gene intended to be expressed, other factors such as transcription factors that are used, etc.

Gene regulatory elements include, but are not limited to, enhancers, promoters, operators, terminators, etc., as well as combinations thereof. As a non-limiting example, a regulatory element can comprise both a promoter and an operator.

In some embodiments, the regulatory element is constitutive in that it is active in all circumstances in the cell. For example, a constitutive element such as a constitutive promoter can be used to express a gene product without requiring additional regulation.

In some embodiments, the regulatory element is inducible, i.e., it is only active in response to a specific stimulus.

For example, the lac operator is inducible in that it can be made active in the presence of IPTG (Isopropyl β-D-1-thiogalactopyranoside). Another example, is the arabinose promoter that is made active in the presence of arabinose.

In some embodiments, the regulatory element is bidirectional, in that it can drive expression of a gene placed on other side of it in a sequence. Thus, in some embodiments, expression of at least two gene elements can be driven by the same gene element.

Gene segments that serve as regulatory elements are readily available in the art, and many are commercially available from vendors. For example, expression plasmids or other vectors that already contain one or more regulatory elements to express a gene segment of interest are readily available.

Analysis of Selected Versions of Polypeptides and/or Polynucleotides

After one or more rounds of selection, selected versions of polypeptides and/or polynucleotides can be recovered from host cells that survived the selection and analyzed. In schematics using more than one cycle of evolution (mutagenesis followed by one or more selection rounds), this analysis can happen at the end of every cycle or only in some cycles.

Examples of types of analysis include, but are not limited to, sequencing, binding and/or cleavage assays (including in vitro assays), verification of activity of selected versions in cell types other than the host cell type.

As a non-limiting example, next generation (also known as high throughput sequencing) can be performed to sequence all or most of the selected variants.

In some embodiments, deep sequencing is performed, meaning that each nucleotide is read several times during the sequencing process, for example at a depth of greater than at least 7, at least 10, at least 15, at least 20, or ever greater, wherein depth (D) is calculated as $$D = N \times L/G \qquad \text{(Equation 1)},$$

wherein N is the number of reads, L is the length of the original genome, and G is length of the polynucleotide being sequenced.

In some embodiments, Sanger sequencing is used to analyze at least some of the selected versions.

Analysis of the sequences may be used, for example, to check for enriched amino acid residues or nucleotide, which are indicative of selected versions.

Alternatively or additionally, a sample of selected versions may be sequenced, e.g., from individual host cell colonies (e.g., bacterial colonies).

Binding and/or cleavage assays are known in the art. Some of these assays are performed in vitro, e.g., using cell components or isolated molecules (such as polypeptides, polynucleotides, or ribonuclear proteins) rather than whole cells.

In some embodiments, an in vitro assay for binding and/or cleavage of a DNA substrate is performed. In some embodiments, the assay tests the activity of lysates extracted from host cells that survived one or more rounds of selection. In some embodiments, the assay tests the activity of polypeptides, polynucleotides, and/or ribonuclear proteins, or complexes thereof, extracted from host cells that survived one or more rounds of selection.

In some embodiments, analysis comprises performing one or more assays to test one or more function(s) of the products of the selected versions of polynucleotides in the library (e.g., polypeptides encoded by the selected version or polynucleotides whose template is the selected version).

Uses

In some embodiments, selection methods of the present invention are used together with a mutagenesis method that generates the library of plasmids. Any mutagenesis method can be used with selection methods of the present invention.

In some embodiments, one round of mutagenesis followed by one or more rounds of selection is used. This cycle may be performed once, or it may be repeated one or more times, e.g., as part of a directed evolution strategy, in which the versions of polypeptides and/or polynucleotides of interest that are selected in one cycle are mutagenized in the mutagenesis round of the next cycle. Cycles can be repeated as many times as desired, for example, until the selected versions of the polypeptide and/or polynucleotide of interest obtained meet certain criteria and/or a desired number of selected polypeptides and/or polynucleotides meeting certain criteria are obtained.

In some embodiments, in one cycle, one round of mutagenesis is followed by a round of positive selection (e.g., for versions of a polypeptide and/or polynucleotide of interest that cleave and/or bind a DNA target site).

In some embodiments, in one cycle, one round of mutagenesis is followed by a round of positive selection, which is followed by a round of negative selection (e.g., for versions of a polypeptide and/or polynucleotide of interest that do not cleave and/or do not bind a DNA target site).

In some embodiments, in one cycle, one round of mutagenesis is followed by a round of negative selection, which is followed by a round of positive selection.

In embodiments in which more than one cycle is performed, the cycles need not have the same schematic in terms of mutagenesis and selection rounds. Additionally, other details need not be the same between cycles, for example, the method of mutagenesis need not be the same from one cycle to the next, nor do the exact conditions or schematics of the selection rounds need to be the same.

Accordingly, selection methods of the present disclosure can be used to select for polypeptides and/or polynucleotides of interest with desired binding and/or cleaving site specificities.

For example, selection methods can be used to select for polypeptides and/or polynucleotides of interest that bind to one allele but not another allele. For example, the ability to discriminate between a disease allele and a wild-type allele can be used to develop therapies, for example, based on gene editing, gene repression, and/or gene activation techniques. In some embodiments, for example, a positive selection is carried out to select for polypeptides or polynucleotides of interest that recognize one allele (e.g., a disease allele), and then a negative selection is a carried out to select against polypeptides or polynucleotides of interest that recognize another allele (e.g., a wild-type allele). In some embodiments, a negative selection is carried out to select against polypeptides or polynucleotides of interest that recognize one allele (e.g., a wild type allele), then a positive selection is carried out to select for polypeptides and/or polynucleotides of interest that recognize the other allele (e.g., a disease allele).

As illustrated in the Examples, selection methods of the present invention have been used in evolution schemes to evolve a polypeptide with the ability to discriminate between alleles differing by only one base change.

As another example, selection methods can be used to select for polypeptides and/or polynucleotides of interest that have altered binding preferences, e.g., as compared to naturally occurring polypeptides and/or polynucleotides of interest. For example, certain DNA-binding proteins (including enzymes) have very limited binding specificities, therefore limiting their uses. Selecting for and/or evolving site-specific DNA-binding domains or proteins with altered binding specificities (e.g., as compared to that of naturally occurring polypeptides and/or polynucleotides of interest) may increase the range of their use.

In some embodiments, a positive selection is carried out to select for polypeptides and/or polynucleotides of interest that recognize one DNA target site (e.g., a desired new target site), and then a negative selection is a carried out to select against polypeptides and/or polynucleotides of interest that recognize another DNA target site (e.g., the native target site).

In some embodiments, a positive selection is carried out to select for polypeptides and/or polynucleotides of interest that recognize one DNA target site (e.g., a desired new target site), and no negative selection is a carried out.

In some embodiments, a negative selection is carried out to select against polypeptides and/or polynucleotides of interest that recognize one DNA target site (e.g., the native target site), then a positive selection is carried out to select for polypeptides and/or polynucleotides of interest that recognize another DNA target site (e.g., a desired new target site).

As another example, selection methods can be used to select for polypeptides or polynucleotides of interest with reduced off-target activity. Although certain DNA-binding proteins are classified as specific for a particular recognition sequence, some may exhibit promiscuity in that they bind to some degree to one or more off-target sites.

In some embodiments, for example, a negative selection is carried out to select for polypeptides or polynucleotides of interest that do not recognize one or more off-target sites. When it is desired to select against more than one off-target site, in some embodiments, a pool of bacteriophage containing different phagemids is used, wherein each of the different phagemids contains a DNA target site corresponding to one of the off-target sites. Because host cells can be infected again and again by various bacteriophage during the incubating step, it is possible to select against binding to or cleaving at multiple off-targets in a single round of negative selection.

In some embodiments, for example, a positive selection is carried out to select for polypeptides or polynucleotides of interest that recognize a particular recognition sequence, and then a negative selection is a carried out to select against polypeptides or polynucleotides of interest that recognize one or more off-target sites. In some embodiments, a negative selection is carried out to select against polypeptides or polynucleotides of interest that recognize one or more off-target sites, then a positive selection is carried out to select for polypeptides or polynucleotides of interest that recognize a particular recognition sequence.

In some embodiments in which more than one round of selection is used (e.g., a positive selection round and then a negative selection round) in one cycle, methods comprise a step of pelleting (e.g., by centrifugation) the host cells in between rounds of selection. Such a pelleting step may, for example, remove agents used during a previous selection round (e.g., antibiotics, inducers of gene expression such as IPTG, etc.).

Variant nucleases identified using methods described herein may be used to genetically engineer a population of cells. To alter, or engineer a population of cells, cells may be contacted with a variant nuclease described herein, or a vector capable of expressing a variant nuclease, and a guide nucleic acid. As is known in the art, a guide nucleic acid will have a region complementary to a target sequence on a target nucleic acid of the genome of the cells. In some embodiments, a variant nuclease and guide nucleic acid are administered as a ribonucleic protein (RNP). In some embodiments, an RNP is administered at a dose of $1 \times 10^{-4}$ µM to 1 µM RNP. In some embodiments, less than 1%, less than 5%, less than 10%, less than 15% or less than 20% of alterations comprise alterations of off-target sequences in a population of cells. In some embodiments, greater than 70%, greater than 75%, greater than 80%, greater than 85%, greater than 90%, greater than 95%, greater than 98%, greater than 99% of alternations comprise alterations of on-target sequences in a population of cells.

Variant nucleases identified using methods described herein may be used to edit a population of double stranded DNA (dsDNA) molecules. To edit a population of dsDNA molecules, the molecules may be contacted with a variant nuclease described herein and a guide nucleic acid. As is known in the art, a guide nucleic acid will have a region complementary to a target sequence of the dsDNA. In some embodiments, a variant nuclease and guide nucleic acid are administered as a ribonucleic protein (RNP). In some embodiments, an RNP is administered at a dose of 1×10 µM to 1 µM RNP. In some embodiments, less than 1%, less than 5%, less than 10%, less than 15% or less than 20% of edits comprise edits of off-target sequences in a population dsDNA molecules. In some embodiments, greater than 70%, greater than 75%, greater than 80%, greater than 85%, greater than 90%, greater than 95%, greater than 98%, greater than 99% of edits comprise edits of on-target sequences in a population of dsDNA molecules.

Implementation of Genome Editing Systems: Delivery, Formulations, and Routes of Administration As discussed above, the genome editing systems of this disclosure can be implemented in any suitable manner, meaning that the components of such systems, including without limitation an RNA-guided nuclease (e.g., an RNA-guided nuclease variant described herein), gRNA, and optional donor template nucleic acid, can be delivered, formulated, or administered in any suitable form or combination of forms that results in the transduction, expression or introduction of a genome editing system and/or causes a desired repair outcome in a cell, tissue or subject (e.g., ex vivo and/or in vivo). FIG. 19 and Table 3 set forth several, non-limiting examples of genome editing system implementations. Those of skill in the art will appreciate, however, that these listings are not comprehensive, and that other implementations may be possible. In some embodiments, one or more components described herein are delivered/administered in vivo. In some embodiments, one or more components described herein are delivered/administered ex vivo. For example, in some embodiments, an RNA (e.g., mRNA) encoding an RNA-guided nuclease variant described herein is delivered/administered to a cell in vivo or ex vivo. In some embodiments, an RNA-guided nuclease variant described herein is delivered/administered to a cell in vivo or ex vivo as a ribonucleoprotein (RNP) complex with or without a gRNA. With reference to FIG. 19 in particular, the table lists several exemplary implementations of a genome editing system comprising a single gRNA and an optional donor template. However, genome editing systems according to this disclosure may incorporate multiple gRNAs, multiple RNA-guided nucleases (e.g., multiple RNA-guided nuclease variants described herein), and other components such as proteins, and a variety of implementations will be evident to the skilled artisan based on the principles illustrated in FIG. 19. In FIG. 19, "[N/A]" indicates that the genome editing system does not include the indicated component.

Table 3 summarizes various delivery methods for the components of genome editing systems, as described herein. Again, the listing is intended to be exemplary rather than limiting.

TABLE 3

| Delivery Vector/Mode | | Delivery into Non-Dividing Cells | Duration of Expression | Genome Integration | Type of Molecule Delivered |
|---|---|---|---|---|---|
| Physical (e.g., electroporation, particle gun, Calcium Phosphate transfection, cell compression or squeezing) | | YES | Transient | NO | Nucleic Acids and Proteins |
| Viral | Retrovirus | NO | Stable | YES | RNA |
| | Lentivirus | YES | Stable | YES/NO modifications | with RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

Nucleic Acid-Based Delivery of Genome Editing Systems

Nucleic acids encoding the various elements of a genome editing system according to the present disclosure can be administered to subjects or delivered into cells by art-known methods or as described herein. For example, DNA encoding an RNA-guided nuclease (e.g., an RNA-guided nuclease variant described herein) and/or encoding a gRNA, as well as donor template nucleic acids can be delivered by, e.g., vectors (e.g., viral or non-viral vectors), non-vector based methods (e.g., using naked DNA or DNA complexes), or a combination thereof.

Nucleic acids encoding genome editing systems or components thereof can be delivered directly to cells as naked DNA or RNA (e.g., mRNA), for instance by means of transfection or electroporation, or may be conjugated to molecules (e.g., N-acetylgalactosamine) promoting uptake by the target cells (e.g., erythrocytes, HSCs). Nucleic acid vectors, such as the vectors summarized in Table 3, may also be used.

Nucleic acid vectors can comprise one or more sequences encoding genome editing system components, such as an RNA-guided nuclease (e.g., an RNA-guided nuclease variant described herein), a gRNA and/or a donor template. A vector can also comprise a sequence encoding a signal peptide (e.g., for nuclear localization, nucleolar localization, or mitochondrial localization), associated with (e.g. inserted into, fused to) a sequence coding for a protein. As one example, a nucleic acid vectors can include a Cas9 coding sequence that includes one or more nuclear localization sequences (e.g., from SV40).

The nucleic acid vector can also include any suitable number of regulatory/control elements, e.g., promoters, enhancers, introns, polyadenylation signals, Kozak consensus sequences, or internal ribosome entry sites (IRES). These elements are well known in the art, and are described in Cotta-Ramusino.

Nucleic acid vectors according to this disclosure include recombinant viral vectors. Exemplary viral vectors are set forth in Table 3, and additional suitable viral vectors and their use and production are described in Cotta-Ramusino. Other viral vectors known in the art may also be used. In addition, viral particles can be used to deliver genome editing system components in nucleic acid and/or peptide form. For example, "empty" viral particles can be assembled to contain any suitable cargo. Viral vectors and viral particles can also be engineered to incorporate targeting ligands to alter target tissue specificity.

In addition to viral vectors, non-viral vectors can be used to deliver nucleic acids encoding genome editing systems according to the present disclosure. One important category of non-viral nucleic acid vectors are nanoparticles, which may be organic or inorganic. Nanoparticles are well known in the art, and are summarized in Cotta-Ramusino. Any suitable nanoparticle design may be used to deliver genome editing system components or nucleic acids encoding such components. For instance, organic (e.g. lipid and/or polymer) nonparticles may be suitable for use as delivery vehicles in certain embodiments of this disclosure. Exemplary lipids for use in nanoparticle formulations, and/or gene transfer are shown in Table 4, and Table 5 lists exemplary polymers for use in gene transfer and/or nanoparticle formulations.

TABLE 4

Lipids Used for Gene Transfer

| Lipid | Abbreviation | Feature |
| --- | --- | --- |
| 1,2-Dioleoyl-sn-glycero-3-phosphatidyl-choline | DOPC | Helper |
| 1,2-Dioleoyl-sn-glycero-3-phosphatidyl-ethanolamine | DOPE | Helper |
| Cholesterol | | Helper |
| N-[1-(2,3-Dioeyloxy)propyl] N,N,N-trimethylammonium chloride | DOTMA | Cationic |

TABLE 4-continued

Lipids Used for Gene Transfer

| Lipid | Abbreviation | Feature |
| --- | --- | --- |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethyl-pyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propyl-amide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxy-ethyl)]-dimethylammonium chloride | CLIP-1 | Cationic |
| rac-[2(2,3-Dihexadecyloxypropyl-oxymethyloxy)ethyl]trimethylammonium bromide | CLIP-6 | Cationic |
| Ethyldimyristoylphosphatidylcholine | EDMPC | Cationic |
| 1,2-Distearyloxy-N,N-dimethyl-3-amino-propane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphospho-choline | DSEPC | Cationic |
| N-Palmitoyl D-erythro-sphingosyl carbamoyl-spermine | CCS | Cationic |
| N-t-Butyl-N0-tetradecyl-3-tetradecylamino-propionamidine | diC14-amidine | Cationic |
| Octadecenolyoxy[ethyl-2-heptadecenyl-3 hydroxyethyl]imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propyl-amino)-N-ditetradecylcarbamoylme-ethyl-acetamide | RPR209120 | Cationic |
| 1,2-dilinoleyloxy-3-dimethylaminopropane | DLinDMA | Cationic |
| 2,2-dilinoleyl-4-dimethylaminoethyl-[1,3]-dioxolane | DLin-KC2-DMA | Cationic |
| dilinoleyl-methyl-4-dimethylaminobutyrate | DLin-MC3-DMA | Cationic |

TABLE 5

Polymers Used for Gene Transfer

| Polymer | Abbreviation |
| --- | --- |
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine)biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |

TABLE 5-continued

Polymers Used for Gene Transfer

| Polymer | Abbreviation |
| --- | --- |
| Poly(4-hydroxy-L-proline ester) | PHP |
| Poly(allylamine) | |
| Poly(α[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly(2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

Non-viral vectors optionally include targeting modifications to improve uptake and/or selectively target certain cell types. These targeting modifications can include e.g., cell specific antigens, monoclonal antibodies, single chain antibodies, aptamers, polymers, sugars (e.g., N-acetylgalactosamine (GalNAc)), and cell penetrating peptides. Such vectors also optionally use fusogenic and endosome-destabilizing peptides/polymers, undergo acid-triggered conformational changes (e.g., to accelerate endosomal escape of the cargo), and/or incorporate a stimuli-cleavable polymer, e.g., for release in a cellular compartment. For example, disulfide-based cationic polymers that are cleaved in the reducing cellular environment can be used.

In certain embodiments, one or more nucleic acid molecules (e.g., DNA molecules) other than the components of a genome editing system, e.g., the RNA-guided nuclease component and/or the gRNA component described herein, are delivered. In an embodiment, the nucleic acid molecule is delivered at the same time as one or more of the components of the Genome editing system are delivered. In an embodiment, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Genome editing system are delivered. In an embodiment, the nucleic acid molecule is delivered by a different means than one or more of the components of the genome editing system, e.g., the RNA-guided nuclease component and/or the gRNA component, are delivered. The nucleic acid molecule can be delivered by any of the delivery methods described herein. For example, the nucleic acid molecule can be delivered by a viral vector, e.g., an integration-deficient lentivirus, and the RNA-guided nuclease molecule component and/or the gRNA component can be delivered by electroporation, e.g., such that the toxicity caused by nucleic acids (e.g., DNAs) can be reduced. In an embodiment, the nucleic acid molecule encodes a therapeutic protein, e.g., a protein described herein. In an embodiment, the nucleic acid molecule encodes an RNA molecule, e.g., an RNA molecule described herein.

Delivery of RNPs and/or RNA Encoding Genome Editing System Components

RNPs (complexes of gRNAs and RNA-guided nucleases (e.g., RNA-guided nuclease variants described herein)) and/or RNAs (e.g., mRNAs) encoding RNA-guided nucleases (e.g., RNA-guided nuclease variants described herein) and/or gRNAs, can be delivered into cells or administered to subjects by art-known methods, some of which are described in Cotta-Ramusino. In vitro, RNA (e.g., mRNA) encoding an RNA-guided nuclease (e.g., an RNA-guided nuclease variant described herein) and/or a gRNA can be delivered, e.g., by microinjection, electroporation, transient cell compression or squeezing (see, e.g., Lee 2012). Lipid-mediated transfection, peptide-mediated delivery, GalNAc- or other conjugate-mediated delivery, and combinations thereof, may also be used for delivery in vitro and in vivo.

In vitro, delivery via electroporation comprises mixing the cells with the RNA (e.g., mRNA) encoding RNA-guided nucleases and/or gRNAs, with or without donor template nucleic acid molecules, in a cartridge, chamber or cuvette and applying one or more electrical impulses of defined duration and amplitude. Systems and protocols for electroporation are known in the art, and any suitable electroporation tool and/or protocol may be used in connection with the various embodiments of this disclosure.

Route of Administration

Genome editing systems, or cells altered or manipulated using such systems, can be administered to subjects by any suitable mode or route, whether local or systemic. Systemic modes of administration include oral and parenteral routes. Parenteral routes include, by way of example, intravenous, intramarrow, intrarterial, intramuscular, intradermal, subcutaneous, intranasal, and intraperitoneal routes. Components administered systemically may be modified or formulated to target, e.g., HSCs, hematopoietic stem/progenitor cells, or erythroid progenitors or precursor cells.

Local modes of administration include, by way of example, intramarrow injection into the trabecular bone or intrafemoral injection into the marrow space, and infusion into the portal vein. In an embodiment, significantly smaller amounts of the components (compared with systemic approaches) may exert an effect when administered locally (for example, directly into the bone marrow) compared to when administered systemically (for example, intravenously). Local modes of administration can reduce or eliminate the incidence of potentially toxic side effects that may occur when therapeutically effective amounts of a component are administered systemically.

Administration may be provided as a periodic bolus (for example, intravenously) or as continuous infusion from an internal reservoir or from an external reservoir (for example, from an intravenous bag or implantable pump). Components may be administered locally, for example, by continuous release from a sustained release drug delivery device.

In addition, components may be formulated to permit release over a prolonged period of time. A release system can include a matrix of a biodegradable material or a material which releases the incorporated components by diffusion. The components can be homogeneously or heterogeneously distributed within the release system. A variety of release systems may be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly(ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used. Typically the microspheres are composed of a polymer of lactic acid and glycolic acid, which are structured to form hollow spheres. The spheres can be approximately 15-30 microns in diameter and can be loaded with components described herein.

Multi-Modal or Differential Delivery of Components

Skilled artisans will appreciate that different components of genome editing systems can be delivered together or separately and simultaneously or nonsimultaneously. Separate and/or asynchronous delivery of genome editing system components may be particularly desirable to provide temporal or spatial control over the function of genome editing systems and to limit certain effects caused by their activity.

Different or differential modes as used herein refer to modes of delivery that confer different pharmacodynamic or pharmacokinetic properties on the subject component molecule, e.g., a RNA-guided nuclease molecule, gRNA, template nucleic acid, or payload. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., AAV or lentivirus, delivery.

By way of example, the components of a genome editing system, e.g., a RNA-guided nuclease and a gRNA, can be delivered by modes that differ in terms of resulting half-life or persistent of the delivered component the body, or in a particular compartment, tissue or organ. In an embodiment, a gRNA can be delivered by such modes. The RNA-guided nuclease molecule component can be delivered by a mode which results in less persistence or less exposure to the body or a particular compartment or tissue or organ.

More generally, in an embodiment, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In certain embodiments, the first pharmacodynamic or pharmacokinetic property, e.g., distribution, persistence or exposure, is more limited than the second pharmacodynamic or pharmacokinetic property.

In certain embodiments, the first mode of delivery is selected to optimize, e.g., minimize, a pharmacodynamic or pharmacokinetic property, e.g., distribution, persistence or exposure.

In certain embodiments, the second mode of delivery is selected to optimize, e.g., maximize, a pharmacodynamic or pharmacokinetic property, e.g., distribution, persistence or exposure.

In certain embodiments, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In certain embodiments, the second mode of delivery comprises a relatively transient element, e.g., an RNA or protein.

In certain embodiments, the first component comprises gRNA, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gRNAs are incapable of acting in isolation. The second component, a RNA-guided nuclease molecule, is delivered in a transient manner, for example as mRNA encoding the protein or as protein, ensuring that the full RNA-guided nuclease molecule/gRNA complex is only present and active for a short period of time.

Furthermore, the components can be delivered in different molecular form or with different delivery vectors that complement one another to enhance safety and tissue specificity.

Use of differential delivery modes can enhance performance, safety, and/or efficacy, e.g., the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in an embodiment, a first component, e.g., a gRNA is delivered by a first delivery mode that results in a first spatial, e.g., tissue, distribution. A second component, e.g., a RNA-guided nuclease molecule is delivered by a second delivery mode that results in a second spatial, e.g., tissue, distribution. In an embodiment the first mode comprises a first element selected from a liposome, nanoparticle, e.g., polymeric nanoparticle, and a nucleic acid, e.g., viral vector. The second mode comprises a second element selected from the group. In an embodiment, the first mode of delivery comprises a first targeting element, e.g., a cell specific receptor or an antibody, and the second mode of delivery does not include that element. In certain embodiments, the second mode of delivery comprises a second targeting element, e.g., a second cell specific receptor or second antibody.

When the RNA-guided nuclease molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA and the RNA-guided nuclease molecule are packaged in separated delivery vehicles with distinct but overlapping tissue tropism, the fully functional complex is only be formed in the tissue that is targeted by both vectors.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following examples. The examples are provided for illustrative purposes only. They are not to be construed as limiting the scope or content of the disclosure in any way.

EXAMPLES

Example 1: Evolution of an Allele-Specific Cas9 to a Single Base-Pair Mutation Conferring Cone Rod Dystrophy 6 (CORD6)

The present Example demonstrates that selection methods of the present invention can be used in an evolution strategy to evolve a site-specific nuclease with specificity for a disease allele differing only by a point mutation (a single base change) as compared to the wild type, non-disease allele.

The use of Cas9 or other targeted nucleases in allele-specific cutting of heterozygous sequences is hindered by promiscuous activity, especially with alleles differing by a single base. We aimed to engineer Cas9 mutants which could selectively cut only one allele, here selectively cutting alleles with the R838S mutation in the retinal guanylate cyclase (GUCY2D) protein, which confers the CORD6 disease phenotype. We constructed plasmid pEvolCORD6, which encodes a Cas9 protein and a gRNA targeting the CORD6 sequence TAACCTGGAGGATCTGATCC (SEQ ID NO: 1). pEvol_CORD6 also constitutively expresses beta-lactamase, which confer resistance to ampicillin. Two phagemids (plasmids containing phage origin fl elements), pSelect_CORD6 and pSelect_GUCY2DWT, were also constructed, containing potential target sites TAACCTGGAGGATCTGATCCGGGAGA (SEQ ID NO: 2) and TAACCTGGAGGATCTGATCCGGGAGC (SEQ ID NO: 3), respectively. Bold bases indicate the site of the R838S mutation. The site of the mutation was chosen to be targeted to the sixth position of the wild-type Cas9 PAM (NNGRRT). In this example, we selected for Cas9 mutants that cut adjacent to a modified PAM with an A in the sixth position (i.e., NNGRRA) ("positive selection") while also selecting against Cas9 mutants that cut adjacent to a modified PAM with a C in the sixth position (i.e., NNGRRC) ("negative selection").

pSelect_CORD6 and pSelect_GUCY2DWT also each contain a constitutively expressed chloramphenicol resistance gene and ccdB (a bacterial toxin) under the control of lac promoter, which allows induction of ccdB expression by IPTG (Isopropyl β-D-1-thiogalactopyranoside).

pSelect_CORD6 and pSelect_GUCY2DWT were separately packaged into helper bacteriophage.

To engineer allele specificity, two E. coli bacterial libraries of Cas9 mutants were generated using the pEvol_CORD6 plasmid as the initial template for mutagenesis, using a comprehensive and unbiased mutagenesis method that targeted every codon and allowed tuning of the mutation rate. One library was tuned such that it had a median of 3 amino acid mutations per Cas9 polypeptide ("low" mutation rate), the other had a median of 5 amino acid mutations per Cas9 polypeptide ("high" mutation rate).

In each round of evolution, we subjected each bacterial library of pEvol_CORD6 mutants first to a positive selection for cutting against phage containing pSelect_CORD6, and then to a negative selection against cutting pSelect_GUCY2DWT, in a competitive culture with continuous challenge by phage as follows:

To infect bacteria, phage packaging the appropriate pSelect plasmid was added to saturated bacteria containing a library of pEvol_CORD6 mutants, and the bacterial library was cultured in ampicillin in a liquid culture. For each library, the entire library was cultured in the same liquid culture.

After this initial incubation and infection, positive selection was carried out by adding 1 mM IPTG, which induces ccdB. Cultures were then grown overnight, e.g., for at least 12 hours. Cells were then pelleted, which removes some IPTG. Negative selection was then carried out by growing the bacteria in the presence of 50 μg/ml chloramphenicol (which is constitutively expressed by both pSelect plasmids) and absence of IPTG during a second overnight culture. During both positive and negative selection, bacteria were continuously infected by phage present in the liquid culture, thus presenting a continuous challenge to either cut (in the case of positive selection) or not cut (in the case of negative selection).

Pooled plasmid DNA from all selected library members following negative selection was used as templates for the next mutagenesis reaction. We repeated three rounds of mutagenesis (which generates libraries), positive selection, and negative selection in this manner. By applying dual selection pressures on each library, stringent selection was performed for a Cas9 mutant that contained a PAM specific to the CORD6 allele.

PacBio next-generation sequencing on plasmid DNA isolated from the pooled selected library members was performed in every evolution cycle, after the negative selection round. After only the first evolution cycle, we found that a particular mutant accounted for about 20% of the population, indicating high selective strength. We proceeded to test the cleavage activity of this mutant using E. coli cell lysate containing the mutant protein on amplicons either containing the wildtype or mutated GUCY2D sequence. We observed cleavage only on the CORD6 amplicons (FIG. 1). Further analysis of the PAM preference of this mutant also indicated two-fold higher specificity for the sixth-position A rather than C. The activity of this highly selected mutant confirms the designed selective pressures and demonstrates successful engineering of an allele-specific Cas9 mutant through an unbiased mutagenesis method and a competitive selection strategy.

Example 2: Evolution of Cas9 with Reduced Off-Target Activities Using Known Off-Targets The present Example describes how selection methods of the present invention can be used in an evolution strategy to reduce off-target activity of a site-specific DNA-binding enzyme.

Off-target cleavage is a common byproduct of Cas9 targeted DNA cleavage. In order to mitigate this effect, selection for on-target cleavage ("positive selection") can be coupled with selection against known or potential off-target sequences ("negative selection") in our system. Off-targets, such as those discovered by GUIDE-SEQ or other methods, can be counter-selected in an informed manner. Alternatively, libraries of potential off-targets, such as single-base-pair mismatches, can be selected against. In this way, specific guides can be tailored to preferentially cleave at the appropriate site by combining them with a Cas9 that has been evolved to reduce off-target cleavage.

Figure 2:
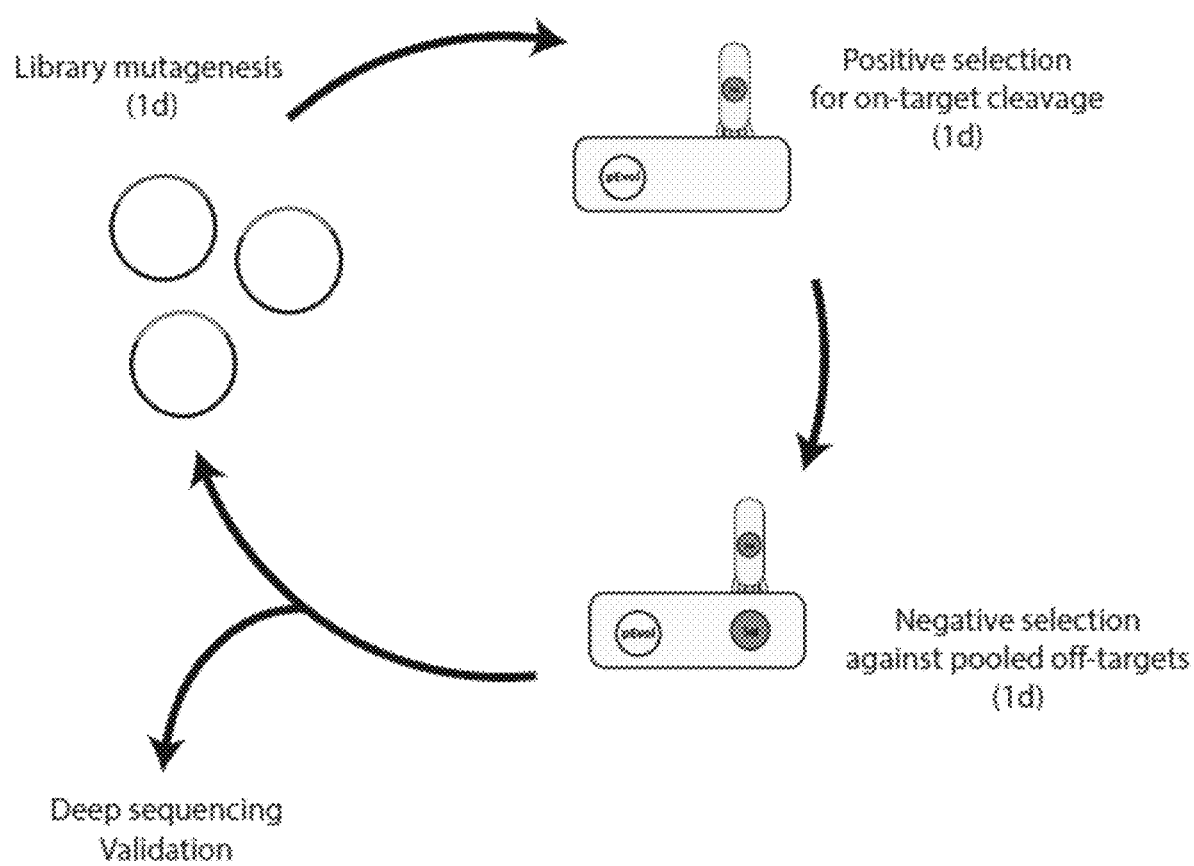
FIG. 2 shows a schematic outlining an evolutionary strategy for selecting against nucleases that show activity at known off-target sites. In each cycle, library generation by a mutagenesis method is followed by a round of positive selection for on-target cleavage, which is followed by a round of negative selection against pooled bacteriophage containing various off-target sites.

Evolution in this case proceeds by first selecting for cleavage of the on-target in positive selection and then for a negative selection against mixed phage populations of the designated off-targets followed by optional deep sequencing validation (FIG. 2). This evolutionary algorithm may be repeated over several rounds.

Example 3: Evolution of an Allele-Specific Cas9

The present Example demonstrates that selection methods of the present invention can be used in an evolution strategy to evolve a site-specific nuclease with specificity for a disease allele differing only by a point mutation (a single base change) as compared to the wild type, non-disease allele. However, the selection methods of the present invention may also be used to evolve a site-specific nuclease with specificity for an allele (e.g., a mutant or disease allele) differing by greater than a single base change as compared to another allele (e.g., wild-type or non-disease allele).

Figure 3:
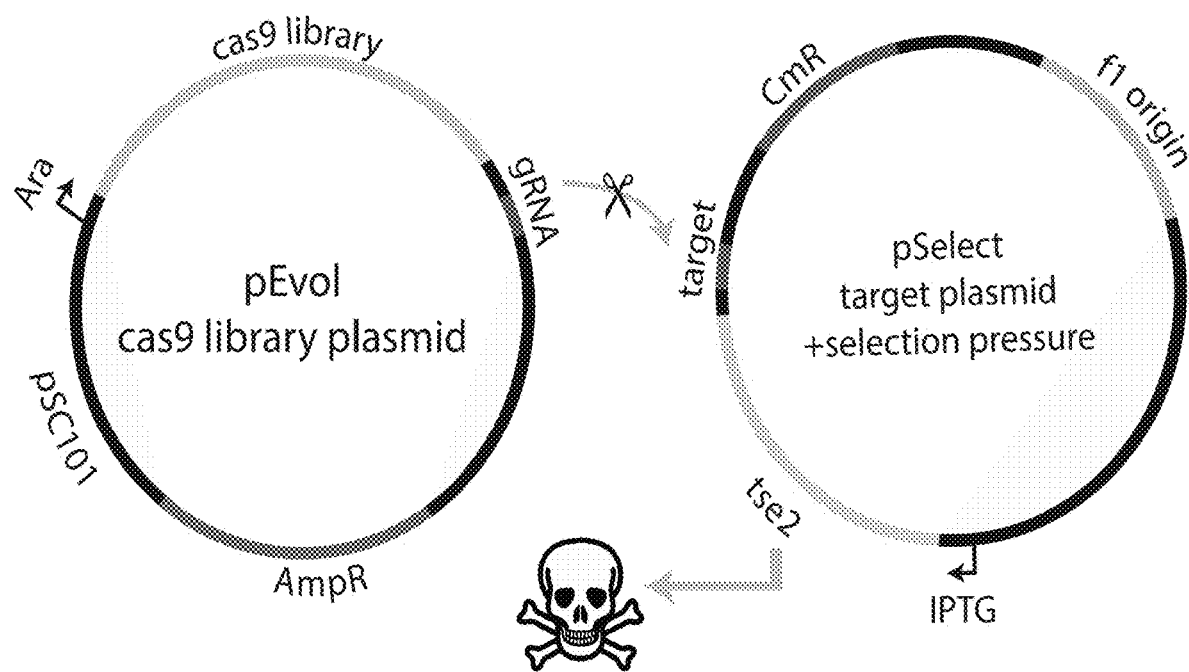
FIG. 3 depicts an exemplary Cas9 library plasmid and a pSelect target phagemid.

The use of Cas9 or other targeted nucleases in allele-specific cutting of heterozygous sequences is hindered by promiscuous activity, especially with alleles differing by a single base. We aimed to engineer Cas9 mutants which would selectively cut only one allele (e.g., allele 1, mutant allele), and not cut an allele differing by a single base (e.g., allele 2, wild-type allele). We also aimed to improve the efficiency of methods that select for Cas9 mutants to achieve the greatest discrimination for the cutting of one allele. Selection of the most discriminating Cas9 mutants may be achieved by control of, for example, the amount of Cas9 present in the selection process and/or, improvement in the efficiency of the positive and negative selection. The amount of Cas9 in a selection system may be controlled by, for example, use of lower copy numbers of a plasmid which expresses Cas9. In some embodiments, amount of Cas9 is controlled by placing expression of Cas9 under the control of an inducible promoter. In some embodiments, an inducible promoter is an arabinose promoter (FIG. 3).

Positive and negative selection processes may rely on inducible expression of toxin molecules and/or expression of resistance to a drug such as an antibiotic. For example, when expression of a toxin is induced from a plasmid, only cells which comprise a Cas9 mutant that recognizes and cuts an appropriate target (e.g., allele 1, mutant allele) in the plasmid will survive. Cells which comprise a Cas9 that does not recognize and cut the appropriate target, are killed by the toxin. This positive selection step selects for all Cas9 molecules that are capable of recognizing and cutting the appropriate target (e.g., allele 1, mutant allele).

In another embodiment, when cells are treated with an antibiotic, only cells which comprise a Cas9 that cuts an inappropriate target in a plasmid conferring resistance to the antibiotic are killed. Cells which comprise a Cas9 that does not recognize an inappropriate target (e.g., allele 2, wild type allele) maintain resistance to the antibiotic and survive. This negative selection step selects against Cas9 molecules that are capable of recognizing and cutting the inappropriate target (e.g., allele 2, wild type allele).

Utility of positive and negative selection steps for the identification of highly selective Cas9 molecules relies, at least in part, on a high degree of discrimination in cell killing. Comparison of cell growth kinetics during selection can characterize the efficiency of the selection for optimal Cas9 molecules.

Efficiency of Selection Using Tse2

A plasmid, pEvol_CAS, which encodes a Cas9 protein and a gRNA targeting a target sequence was constructed. A plasmid, pEvol_NONTARGETING, which encodes a Cas9 protein and a non-targeting gRNA was also constructed. Both plasmids constitutively expresses beta-lactamase, which confer resistance to ampicillin (AmpR) and an inducible arabinose promoter (Ara) to control expression of Cas9. Phagemids (plasmid containing phage origin fl elements), pSelect_MUT and pSelect_WT were also constructed, each containing a potential target site. The phagemids also contained a constitutively expressed chloramphenicol resistance gene (CmR) and tse2 (a bacterial toxin) under the control of lac promoter, which allows induction of tse2 expression by IPTG (Isopropyl 3-D-1-thiogalactopyranoside). pSelect_MUT and pSelect_WT were each separately packaged into helper bacteriophage.

To engineer allele specificity, two E. coli bacterial libraries of Cas9 mutants were generated using the pEvol_CAS plasmid as the initial template for mutagenesis, using a comprehensive and unbiased mutagenesis method that targeted every codon and allowed tuning of the mutation rate. One library was tuned such that it had a median of 3 amino acid mutations per Cas9 polypeptide ("low" mutation rate), the other had a median of 5 amino acid mutations per Cas9 polypeptide ("high" mutation rate).

In each round of evolution, we subjected each bacterial library of pEvol_CAS mutants to positive selection for cutting against phage containing pSelect_MUT in a competitive culture with continuous challenge by phage as follows:

To infect bacteria, phage packaging the pSelect_MUT plasmid was added to bacteria containing a library of pEvol_CAS mutants or pEvol_NONTARGETING, and the bacterial library was cultured in ampicillin in a liquid culture. For each library, the entire library was cultured in the same liquid culture.

After this initial incubation and infection, the stringency of positive selection using tse2 was assessed by adding 1 mM IPTG, to induce tse2 expression, to a subset of the pEvol_CAS cultures and to a subset of the pEvol_NONTARGETING cultures. Expression of Cas9 and guide RNA was induced by addition of arabinose. Cas9 and guide RNA expression was not induced in a subset of the pEvol_CAS cultures that were treated with IPTG. Cultures were then grown overnight, e.g., for at least 12 hours. During positive selection, bacteria were continuously infected by phage present in the liquid culture, thus presenting a continuous challenge to cut the target.

Figure 4:
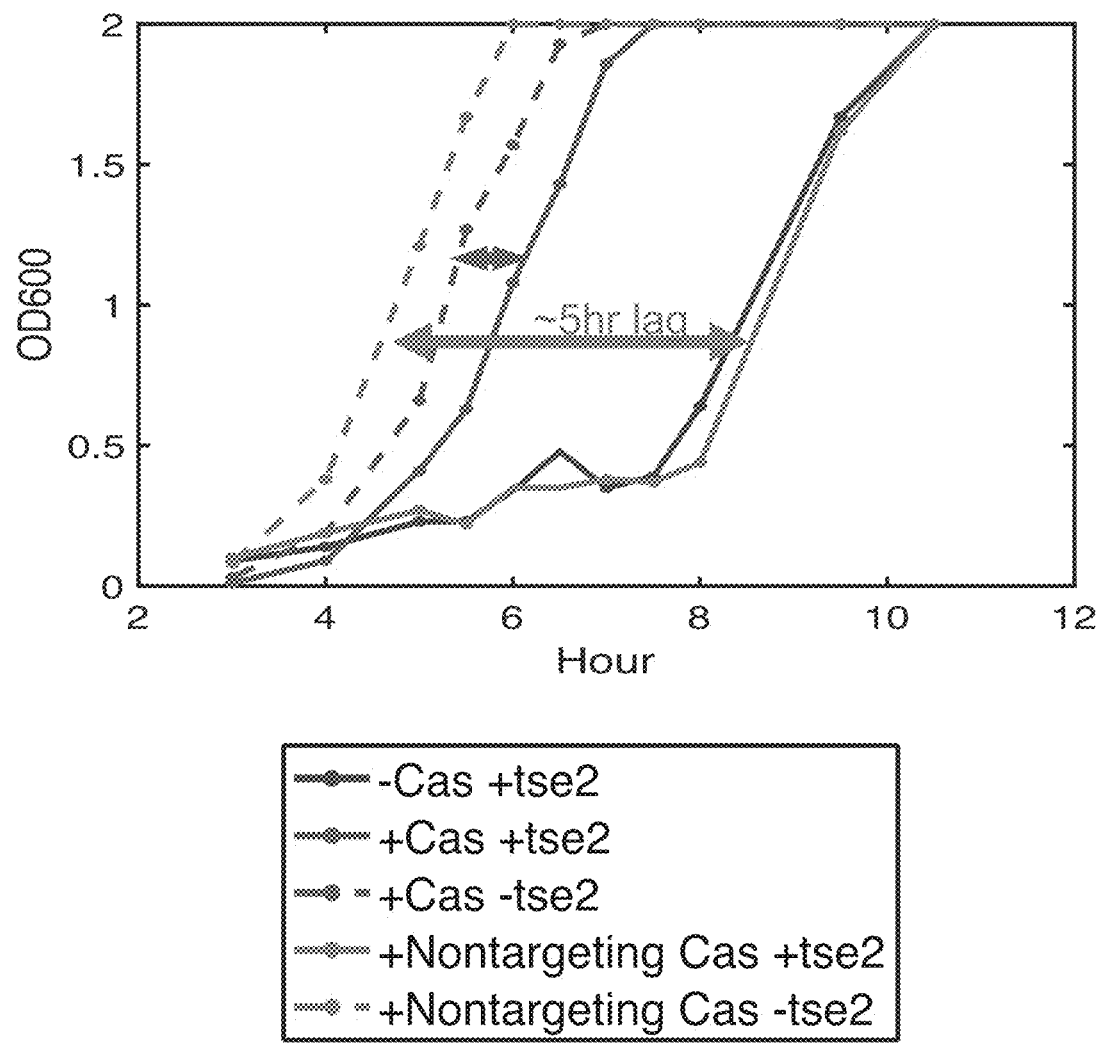
FIG. 4 depicts exemplary results of positive selection using targeting and nontargeting Cas9 with tse2 as a positive selection agent.

As shown in FIG. 4, cultures expressing tse2 but not Cas9 (−Cas+tse2) or expressing a nontargeting guide RNA (+Nontargeting Cas+tse2) exhibited a significant growth lag due to induction of tse2. In comparison, cultures induced to express tse2, but also expressing a Cas9 and targeting guide RNA (+Cas+tse2), which would be expected to cut the target and suppress expression of tse2, demonstrated a rapid growth over approximately 7 hours. Cultures which expressed Cas9 and either a targeting or non-targeting guide RNA, but were not induced to express tse2, demonstrated rapid cell growth over the first 6 hours. These data demonstrate that tse2 has significant cell killing effect when no Cas9 is present, or when the guide RNA does not recognize the target. These data also demonstrate that appropriately targeted Cas9 and guide RNA off-set the effects of induction of tse2 expression.

Efficiency of Selection by Modulating Cas9 Expression

A plasmid library, pEvol_CASLIBRARY, was generated using the pEvol_WTCAS plasmid as the initial template for mutagenesis and a comprehensive and unbiased mutagenesis method that targeted every codon and allowed tuning of the mutation rate. The plasmids encode a Cas9 protein and a gRNA targeting a target sequence. A plasmid pEvol_WT-CAS, which encodes a wild-type Cas9 protein and a targeting gRNA, was also constructed. Both plasmids constitutively expresses beta-lactamase, which confer resistance to ampicillin (AmpR) and an inducible arabinose promoter (Ara) to control expression of Cas9. Phagemids (plasmid containing phage origin fl elements), pSelect_MUT and pSelect_WT were also constructed, containing potential target sites, as described above.

To infect bacteria, phage packaging the pSelect_MUT plasmid was added to saturated bacteria containing a library of pEvol_CASLIBRARY mutants or pEvol_WTCAS, and the bacterial library was cultured in ampicillin in a liquid culture. For each library, the entire library was cultured in the same liquid culture.

After this initial incubation and infection, the stringency of positive selection using tse2 and wild-type Cas or the Cas library was assessed by adding 1 mM IPTG, to induce tse2 expression, to a subset of the pEvol_CASLIBRARY cultures and to a subset of the pEvol_WTCAS cultures. Expression of Cas9 and gRNA was induced by addition of arabinose. Cas9 and gRNA expression was not induced in a subset of the pEvol_CASLIBRARY and pEvolWT CAS cultures that were treated with IPTG. Cultures were then grown overnight, e.g., for at least 12 hours. During positive selection, bacteria were continuously infected by phage present in the liquid culture, thus presenting a continuous challenge to cut the target.

Figure 5:
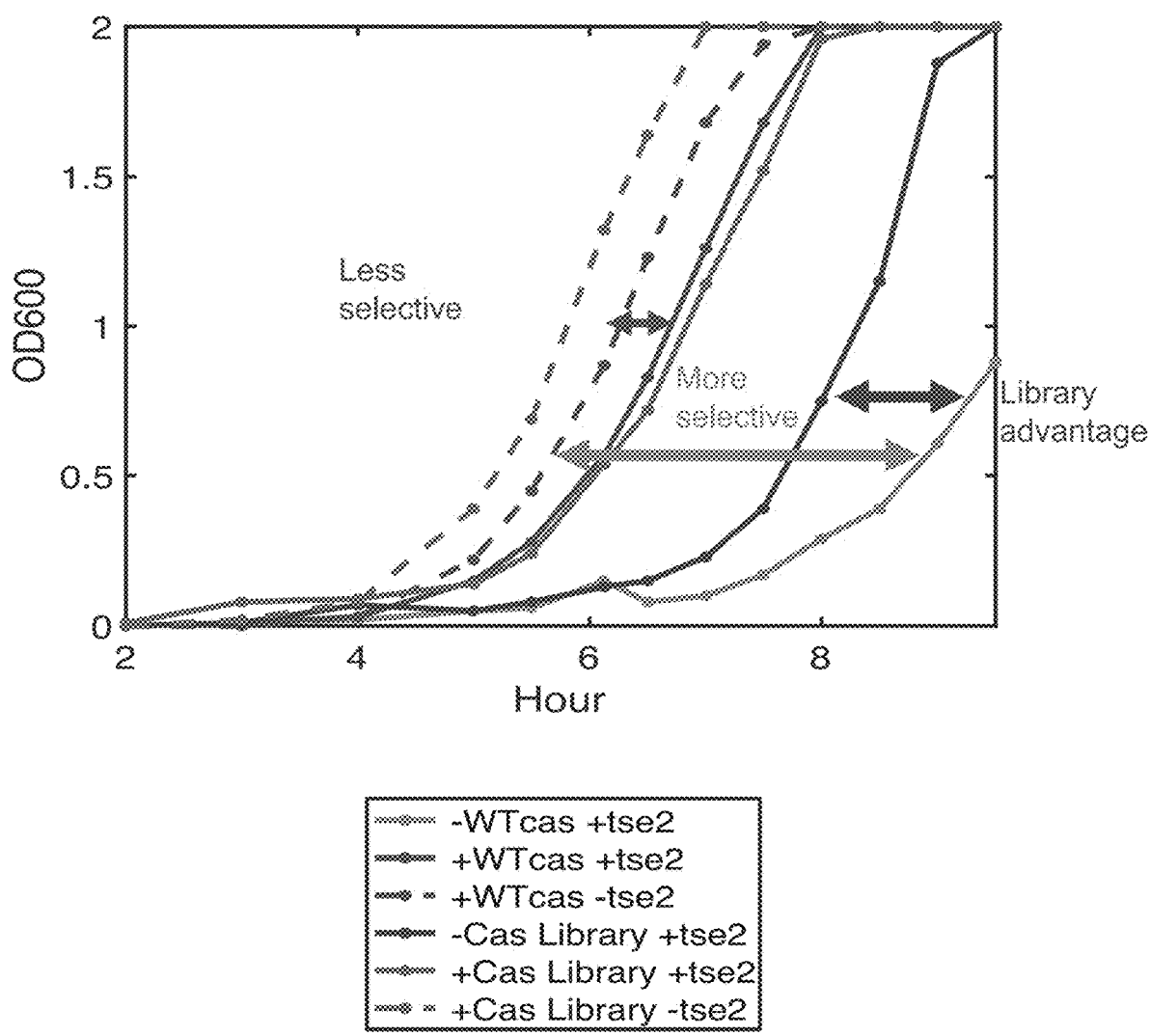
FIG. 5 depicts exemplary results of positive selection using wild-type Cas9 and a library of mutant Cas9 with tse2 as a positive selection agent.

As shown in FIG. 5, cultures expressing tse2 but neither wild-type Cas9 (−WTCas+tse2) or a mutant Cas9 library (−Cas Library+tse2) exhibited a significant growth lag due to induction of tse2. However, wild-type Cas9 cultures exhibited a greater growth lag than mutant Cas9 library cultures indicating leaky expression of Cas9 mutants, even in the absence of arabinose. In comparison, cultures induced to express tse2, but also expressing a Cas9 and targeting guide RNA (+WTcas+tse2 or +Cas Library+tse2), which would be expected to cut the target and suppress expression of tse2, demonstrated rapid growth over approximately 7 hours. Cultures which expressed either wild-type Cas9 or Cas9 library mutants, but were not induced to express tse2, demonstrated rapid cell growth over the first 6 hours. The difference in cell growth between cultures expressing wild-type Cas9, with or without tse2, was less than the difference in cell growth between cultures expressing Cas9 library mutants, with or without tse2. These data suggest that Cas9 library mutants exhibit greater cutting activity than wild-type Cas9. These data also confirmed that tse2 has significant cell killing effect when no Cas9 is present.

Figure 6:
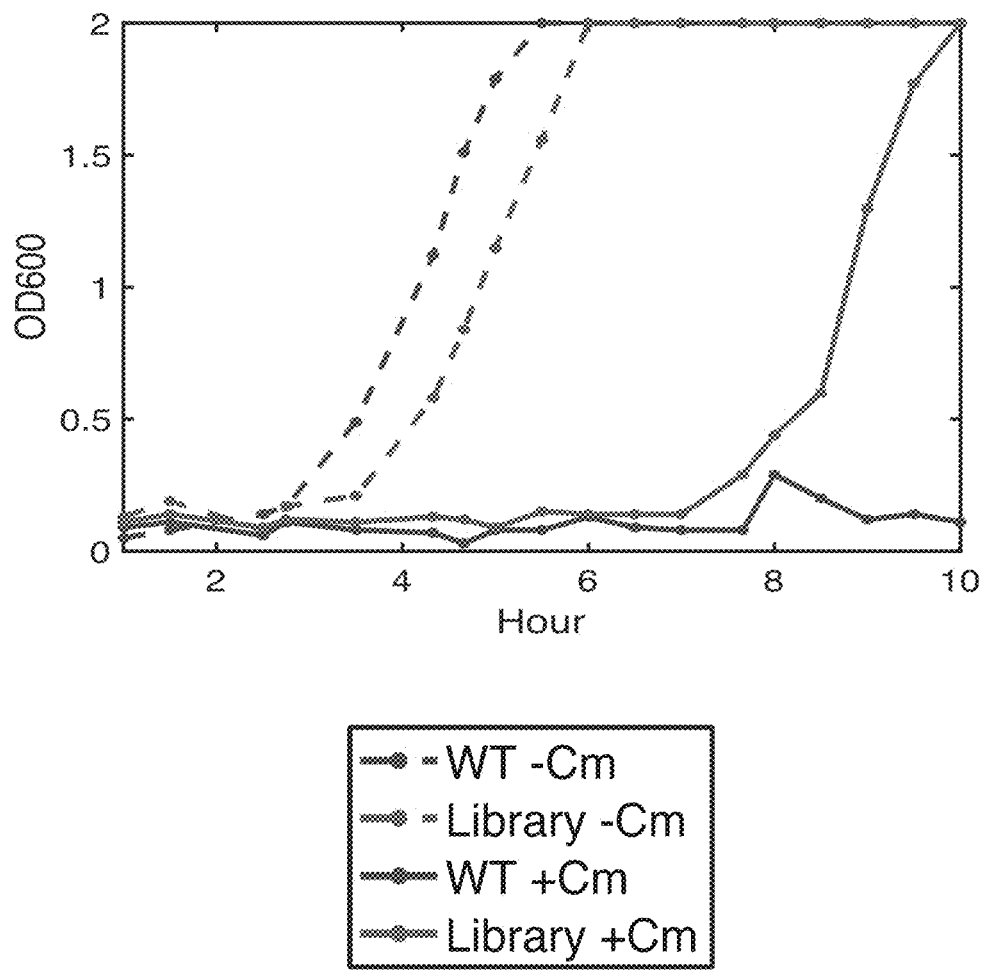
FIG. 6 depicts exemplary results of negative selection using wild-type Cas9 and a library of mutant Cas9 with chloramphenicol ("Cm") as a negative selection agent.

Negative selection was also carried out by growing the bacteria in the presence of 50 µg/ml chloramphenicol (resistance to chloramphenicol is constitutively expressed by the pSelect_MUT and pSelect_WT phagemids) during an overnight culture. Control cultures were not treated with chloramphenicol. During negative selection, bacteria were continuously infected by phage present in the liquid culture, thus presenting a continuous challenge to cut the appropriate target (allele 1, mutant allele) and to not cut the inappropriate target (allele 2, wild-type allele). Both wild-type Cas9 (WTCas+Cm) and mutant Cas9 library (Library+Cm) exhibited a significant growth lag due to elimination of resistant to chloramphenicol by off-target cutting (FIG. 6). However, mutant Cas9 library mutants demonstrated recovery in growth due to selection of Cas9 mutants that did not exhibit off-target cutting and maintained chloramphenicol resistance.

Library Evolution

Figure 7:
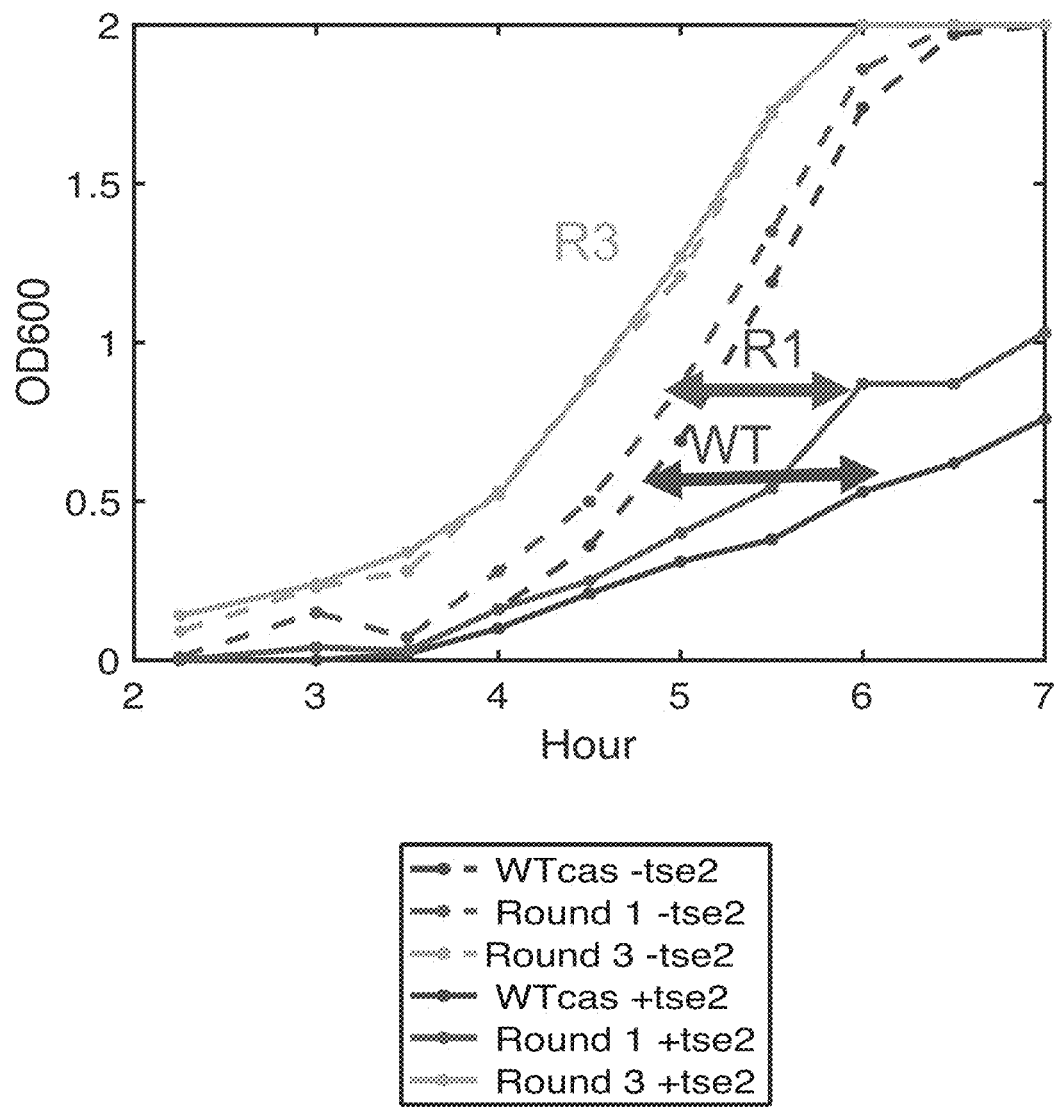
FIG. 7 depicts exemplary results of successive rounds of positive and negative selection of a wild-type Cas to evolve a selective Cas9 mutant.

Successive rounds of library evolution generated Cas9 mutants with high levels of selectivity for cutting a target. This is demonstrated by successive reduction in the growth lag when cultures are induced to express tse2. FIG. 7 shows a significant growth lag for wild-type Cas9 cultures when tse2 is induced (WTcas+tse2) and a significant negative delta when compared to growth of cultures expressing wild-type Cas9 without induction of tse2 (WTcas−tse2). The delta in cell growth is reduced following one round of mutagenesis (for example, Round 1 +tse2 versus Round 1 −tse2). Following three rounds of mutagenesis cell growth curves are nearly identical for cultures induced to express tse2 and those that have not been induced to express tse2. These data indicate that use of tse2 and selective rounds of mutagenesis can generate a mutant Cas9 that this highly selective for on-target cutting.

Example 4: Evolution of *S. pyogenes* Cas9 to Reduce Off Target Cutting

The systems and methods of this disclosure can be employed to select for a variety of nuclease characteristics, as will be further illustrated by the following example. Using the selection method disclosed herein, *S. pyogenes* cas9 variants have been identified from a mutagenized library which have maintained on-target cleavage efficiency but have reduced cutting at off-target loci, providing a means to potentially rescue promiscuous guides for therapeutic use. Mutant *S. pyogenes* Cas9 libraries were generated using scanning mutagenesis at random targets (SMART). Libraries were then transformed into *E. coli* and challenged with phage for three rounds of both positive and negative selection. The positive selection step utilized a positive selection plasmid comprising a cleavage cassette that included an on-target sequence (SEQ ID NO: 4) for a guide RNA directed to a human genomic locus having multiple known off-targets, as determined by GUIDE-Seq, as shown in Table 6:

TABLE 6

Target sites used for positive and negative selection

| POSITIVE/NEGATIVE SELECTABLE TARGET | SEQUENCE |
|---|---|
| Positive (on target) | GTCTGGGCGG TGCTACAACT NGG (SEQ ID NO 4) |
| Negative (off target 1) | AACTGGGTGG TGCTCCAACT CGG (SEQ ID NO 5) |
| Negative (off target 2) | AACGGGGCGG TACTACAACT TGG (SEQ ID NO 6) |
| Negative (off target 3) | GTCTGGTGGT GCTACAACTT GG (SEQ ID NO 7) |
| Negative (off target 4) | ACCTGGACGG TGATACAACC CGG (SEQ ID NO 8) |

Figure 8A:
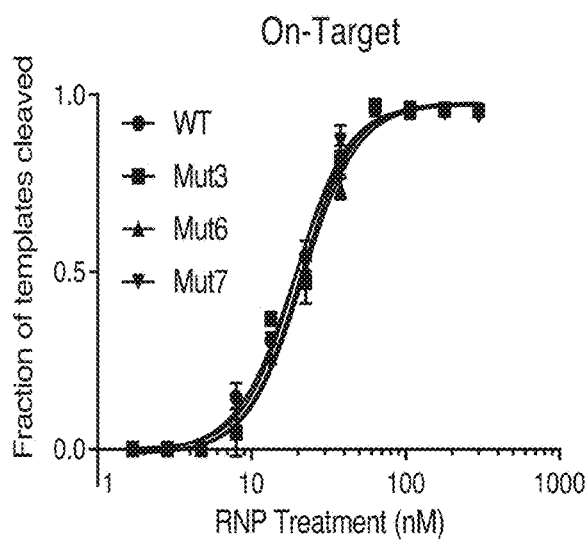
FIGS. 8A and 8B depict the results of biochemical cutting assays using an on-target sequence substrate (FIG. 8A) and an off-target substrate differing from the on-target substrate at four positions (FIG. 8B).
Figure 8B:
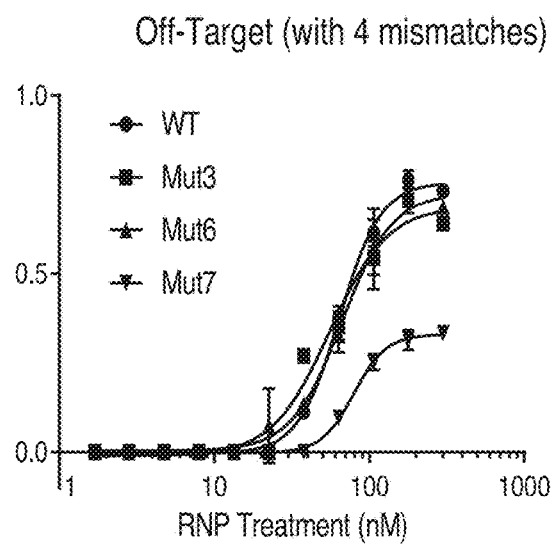
Figure 9A:
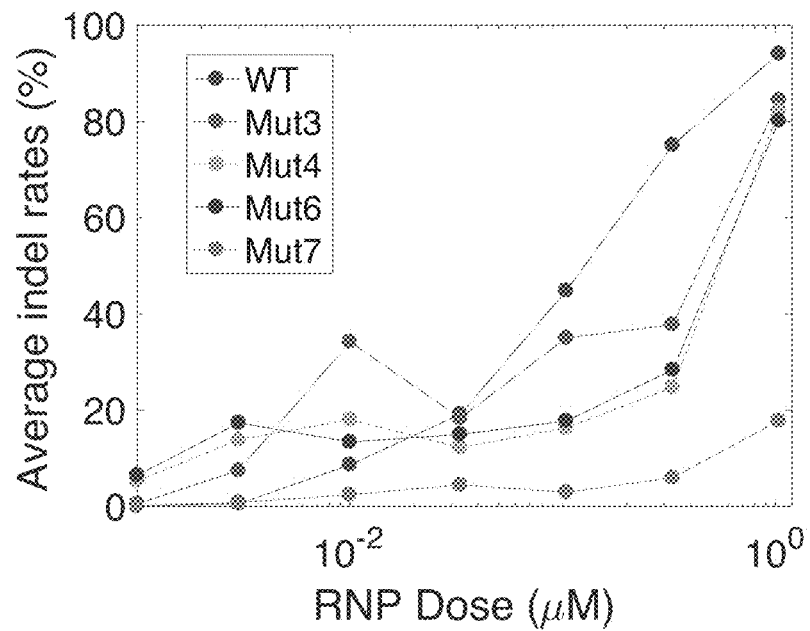
FIGS. 9A and 9B depict the results of an in vivo cutting assay in which cleavage of an on-target genomic sequence (FIG. 9A) and a known off-target genomic sequence (FIG. 9B) are assessed in T cells treated with increasing doses of a Cas9/guide RNA ribonucleoprotein complex (RNP) concentrations.
Figure 9B:
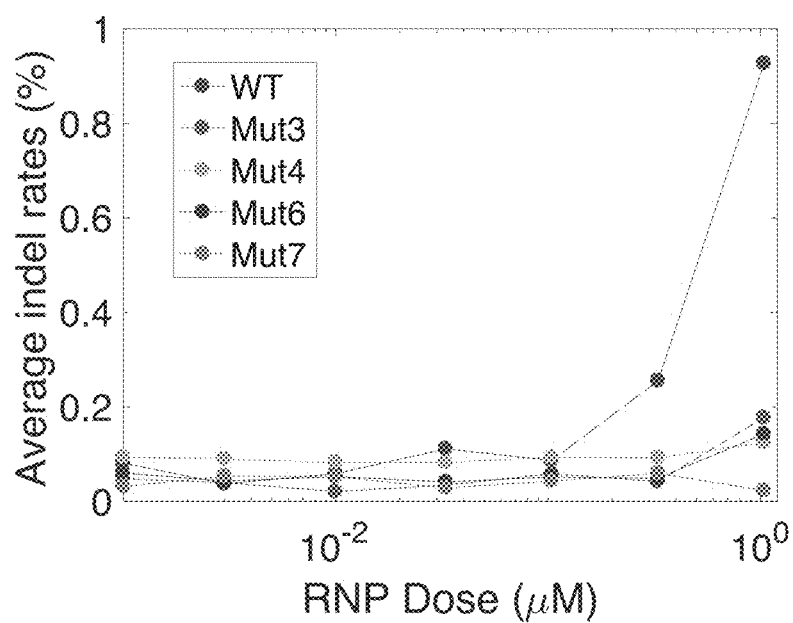
Figure 10:
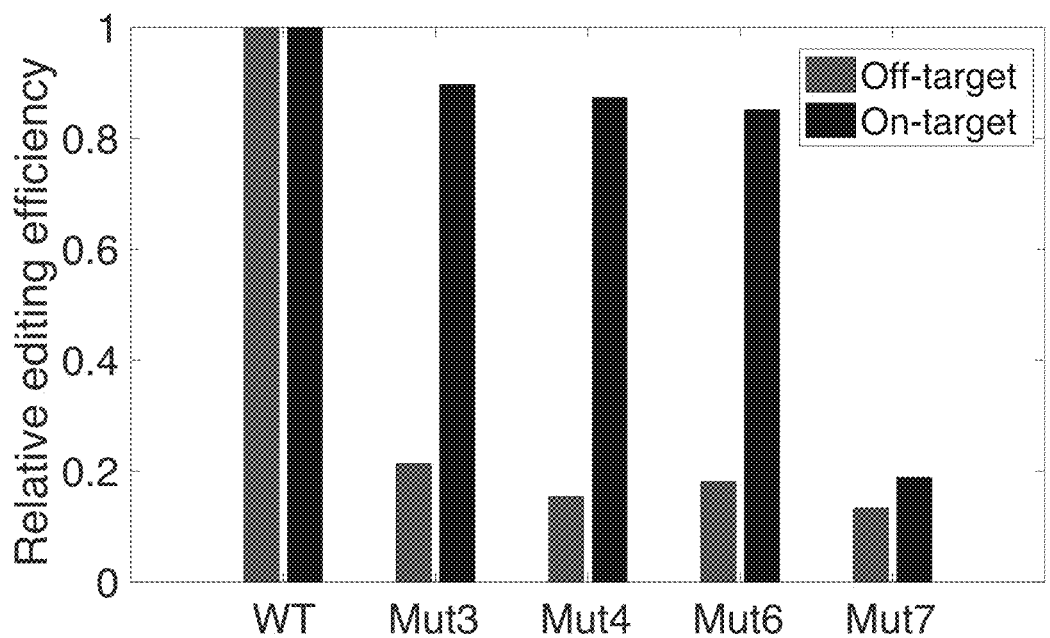
FIG. 10 depicts the ratio of on-target to off-target cleavage in the T cell experiment depicted in FIGS. 9A and 9B at a single RNP concentration.

A single negative selection step utilized four pooled constructs, each comprising a unique off-target differing from the on-target sequence by four residues (SEQ ID NOS: 5-7). Following positive and negative selection steps, clones were selected and sequenced by next generation sequencing (NGS), and reads were aligned to identify the most commonly mutated amino acid residues relative to the unmutated S. pyogenes Cas9 (SEQ ID NO: 13). An in vitro cutting assay utilizing on-target and off-target substrates demonstrated that the clones exhibited on-target cleavage efficiencies comparable to WT Cas9 (FIG. 8A), but while a small number of clones exhibited reduced off-target cutting relative to WT, other clones exhibited substantially the same off-target cleavage efficiency in vitro (FIG. 8B). On target and off-target analyses were also performed for genomic on- and off-target loci in human T cells, as shown in FIGS. 9A and 9B. WT and mutant Cas9/guide RNA ribonucleoprotein complexes (RNPs) were delivered at different concentrations across a >2 log range, genomic DNA was harvested and on—and off-target sites were amplified and sequenced by next-gen sequencing. As illustrated in FIG. 10, several mutant clones exhibited slightly decreased on-target cutting activity relative to WT Cas9, while also exhibiting substantially lower off-target cleavage than WT. Together, these data establish that the phage-selection methods described herein can be successfully applied to reduce off-target cleavage observed with a specific gRNA by selecting compensating Cas9 mutant proteins.

FIG. 19 sets forth selected amino acid residues that are mutated in the clones identified in this screen, as well as residues that may be substituted at each position to generate a mutant having the decreased off-target activity:

TABLE 7

Mutated positions in S. pyogenes Cas9 mutants exhibiting lower off-target cutting activity

| Position | Substitutions |
|---|---|
| D23 | A |
| D1251 | G |
| Y128 | V |
| T67 | L |
| N497 | A |
| R661 | A |
| Q695 | A |
| Q926 | A |

Table 8 sets out exemplary single, double and triple S. pyogenes Cas9 mutants according to certain embodiments of this disclosure. For clarity, this disclosure encompasses Cas9 variant proteins having mutations at 1, 2, 3, 4, 5 or more of the sites set forth in Table 8, though only single, double and triple mutants are listed in the table for economy of presentation.

TABLE 8

Selected S. pyogenes Cas9 amino acid mutant positions

Single Mutants:

| D23 | D1251 | Y128 | T67 | N497 | R661 | Q695 | Q926 |
|---|---|---|---|---|---|---|---|

Double Mutants

| | | | | | | | |
|---|---|---|---|---|---|---|---|
| D23, D1251 | D23, Y128 | D23, T67 | D23, N497 | D23, R661 | D23, Q695 | D23, Q926 | |
| | D1251, Y128 | D1251, T67 | D1251, N497 | D1251, R661 | D1251, Q695 | D1251, Q926 | |
| D23, Y128 | | Y128, T67 | Y128, N497 | Y128, R661 | Y128, Q695 | Y128, Q926 | |
| D23, T67 | D1251, T67 | | Y128, T67 | T67, N497 | T67, R661 | T67, Q695 | T67, Q926 |
| D23, N497 | D1251, N497 | Y128, N497 | T67, N497 | | N497, R661 | N497, Q695 | N497, Q926 |
| D23, R661 | D1251, R661 | Y128, R661 | T67, R661 | N497, R661 | | R661, Q695 | R661, Q926 |
| D23, Q695 | D1251, Q695 | Y128, Q695 | T67, Q695 | N497, Q695 | R661, Q695 | | Q695, Q926 |
| D23, Q926 | D1251, Q926 | Y128, Q926 | T67, Q926 | N497, Q926 | R661, Q926 | Q695, Q926 | |

Triple Mutants

| | | | | | | |
|---|---|---|---|---|---|---|
| | D1251, D23, Y128 | D1251, D23, T67 | D1251, D23, N497 | D1251, D23, R661 | D1251, D23, Q695 | D1251, D23, Q926 |
| Y128, D23, D1251 | | Y128, D23, T67 | Y128, D23, N497 | Y128, D23, R661 | Y128, D23, Q695 | Y128, D23, Q926 |
| D1251, D23, T67 | Y128, D23, T67 | | T67, D23, N497 | T67, D23, R661 | T67, D23, Q695 | T67, D23, Q926 |
| D1251, D23, N497 | Y128, D23, N497 | T67, D23, N497 | | N497, D23, R661 | N497, D23, Q695 | N497, D23, Q926 |
| D1251, D23, R661 | Y128, D23, R661 | T67, D23, R661 | N497, D23, R661 | | R661, D23, Q695 | R661, D23, Q926 |
| D1251, D23, Q695 | Y128, D23, Q695 | T67, D23, Q695 | N497, D23, Q695 | R661, D23, Q695 | | Q695, D23, Q926 |
| D1251, D23, Q926 | Y128, D23, Q926 | T67, D23, Q926 | N497, D23, Q926 | R661, D23, Q926 | Q695, D23, Q926 | |
| D23, D1251, D1251 | Y128, D1251, Y128 | T67, D1251, T67 | N497, D1251, N497 | R661, D1251, R661 | Q695, D1251, Q695 | Q926, D1251, Q926 |
| D23, D1251, Y128 | | Y128, D1251, T67 | Y128, D1251, N497 | Y128, D1251, R661 | Y128, D1251, Q695 | Y128, D1251, Q926 |
| D23, D1251, T67 | Y128, D1251, T67 | | T67, D1251, N497 | T67, D1251, R661 | T67, D1251, Q695 | T67, D1251, Q926 |

TABLE 8-continued

Selected S. pyogenes Cas9 amino acid mutant positions

| | | | | | |
|---|---|---|---|---|---|
| D23, D1251, N497 | Y128, D1251, N497 | T67, D1251, N497 | N497, D1251, R661 | N497, D1251, Q695 | N497, D1251, Q926 |
| D23, D1251, R661 | Y128, D1251, R661 | T67, D1251, R661 | N497, D1251, Q695 | R661, D1251, Q695 | R661, D1251, Q926 |
| D23, D1251, Q695 | Y128, D1251, Q695 | T67, D1251, Q695 | N497, D1251, Q695 | R661, D1251, Q695 | Q695, D1251, Q926 |
| D23, D1251, Q926 | Y128, D1251, Q926 | T67, D1251, Q926 | N497, D1251, Q926 | R661, D1251, Q926 | Q695, D1251, Q926 |
| | D23, Y128, D1251 | D23, Y128, T67 | D23, Y128, N497 | D23, Y128, R661 | D23, Y128, Q695 | D23, Y128, Q926 |
| D23, Y128, D1251 | D1251, Y128, Y128 | D1251, Y128, T67 | D1251, Y128, N497 | D1251, Y128, R661 | D1251, Y128, Q695 | D1251, Y128, Q926 |
| D23, Y128, T67 | D1251, Y128, T67 | | T67, Y128, N497 | T67, Y128, R661 | T67, Y128, Q695 | T67, Y128, Q926 |
| D23, Y128, N497 | D1251, Y128, N497 | T67, Y128, N497 | | N497, Y128, R661 | N497, Y128, Q695 | N497, Y128, Q926 |
| D23, Y128, R661 | D1251, Y128, R661 | T67, Y128, R661 | N497, Y128, R661 | | R661, Y128, Q695 | R661, Y128, Q926 |
| D23, Y128, Q695 | D1251, Y128, Q695 | T67, Y128, Q695 | N497, Y128, Q695 | R661, Y128, Q695 | | Q695, Y128, Q926 |
| | D23, T67, D1251 | T67, T67, Y128 | D23, T67, N497 | D23, T67, R661 | D23, T67, Q695 | D23, T67, Q926 |
| D23, T67, D1251 | D1251, T67, Y128 | | T67, D1251, N497 | T67, D1251, R661 | T67, D1251, Q695 | T67, D1251, Q926 |
| D23, T67, Y128 | D1251, T67, Y128 | | Y128, T67, N497 | Y128, T67, R661 | Y128, T67, Q695 | Y128, T67, Q926 |
| D23, T67, N497 | D1251, T67, N497 | Y128, T67, N497 | | N497, T67, R661 | N497, T67, Q695 | N497, T67, Q926 |
| D23, T67, R661 | D1251, T67, R661 | Y128, T67, R661 | N497, T67, R661 | | R661, T67, Q695 | R661, T67, Q926 |
| D23, T67, Q695 | D1251, T67, Q695 | Y128, T67, Q695 | N497, T67, Q695 | R661, T67, Q695 | | Q695, T67, Q926 |
| D23, T67, Q926 | D1251, T67, Q926 | Y128, T67, Q926 | N497, T67, Q926 | R661, T67, Q926 | Q695, T67, Q926 | |
| | D23, N497, D1251 | D23, N497, Y128 | D23, N497, T67 | D23, N497, R661 | D23, N497, Q695 | D23, N497, Q926 |
| D23, N497, D1251 | N497, Y128, T67 | N497, Y128, T67 | D1251, N497, T67 | D1251, N497, R661 | D1251, N497, Q695 | D1251, N497, Q926 |
| D23, N497, Y128 | D1251, N497, Y128 | | Y128, N497, T67 | Y128, N497, R661 | Y128, N497, Q695 | Y128, N497, Q926 |
| D23, N497, T67 | D1251, N497, T67 | Y128, N497, T67 | | T67, N497, R661 | T67, N497, Q695 | T67, N497, Q926 |
| D23, N497, R661 | D1251, N497, R661 | Y128, N497, R661 | T67, N497, R661 | | R661, N497, Q695 | R661, N497, Q926 |
| D23, N497, Q695 | D1251, N497, Q695 | Y128, N497, Q695 | T67, N497, Q695 | R661, N497, Q695 | | Q695, N497, Q926 |
| D23, N497, Q926 | D1251, N497, Q926 | Y128, N497, Q926 | T67, N497, Q926 | R661, N497, Q926 | Q695, N497, Q926 | |
| | D23, R661, D1251 | D23, R661, Y128 | D23, R661, T67 | D23, R661, N497 | D23, R661, Q695 | D23, R661, Q926 |
| D23, R661, D1251 | D1251, R661, Y128 | D1251, R661, T67 | D1251, R661, N497 | D1251, R661, Q695 | D1251, R661, Q926 | |
| D23, R661, Y128 | D1251, R661, Y128 | | Y128, R661, T67 | Y128, R661, N497 | Y128, R661, Q695 | Y128, R661, Q926 |
| D23, R661, T67 | D1251, R661, T67 | Y128, R661, T67 | | T67, R661, N497 | T67, R661, Q695 | T67, R661, Q926 |
| D23, R661, N497 | D1251, R661, N497 | Y128, R661, N497 | T67, R661, N497 | | N497, R661, Q695 | N497, R661, Q926 |
| D23, R661, Q695 | D1251, R661, Q695 | Y128, R661, Q695 | T67, R661, Q695 | N497, R661, Q695 | | Q695, R661, Q926 |
| D23, R661, Q926 | D1251, R661, Q926 | Y128, R661, Q926 | T67, R661, Q926 | N497, R661, Q926 | Q695, R661, Q926 | |
| | D23, Q695, D1251 | D23, Q695, Y128 | D23, Q695, T67 | D23, Q695, N497 | D23, Q695, R661 | D23, Q695, Q926 |
| D23, Q695, D1251 | D1251, Q695, Y128 | D1251, Q695, T67 | D1251, Q695, N497 | D1251, Q695, R661 | D1251, Q695, Q926 | |
| D23, Q695, Y128 | D1251, Q695, Y128 | | Y128, Q695, T67 | Y128, Q695, N497 | Y128, Q695, R661 | Y128, Q695, Q926 |
| D23, Q695, T67 | D1251, Q695, T67 | Y128, Q695, T67 | | T67, Q695, N497 | T67, Q695, R661 | T67, Q695, Q926 |
| D23, Q695, N497 | D1251, Q695, N497 | Y128, Q695, N497 | T67, Q695, N497 | | N497, Q695, R661 | N497, Q695, Q926 |
| D23, Q695, R661 | D1251, Q695, R661 | Y128, Q695, R661 | T67, Q695, R661 | N497, Q695, R661 | | R661, Q695, Q926 |
| D23, Q695, Q926 | D1251, Q695, Q926 | Y128, Q695, Q926 | T67, Q695, Q926 | N497, Q695, Q926 | R661, Q695, Q926 | |
| | D23, Q926, D1251 | D23, Q926, Y128 | D23, Q926, T67 | D23, Q926, N497 | D23, Q926, R661 | D23, Q926, Q695 |
| D23, Q926, D1251 | D1251, Q926, Y128 | D1251, Q926, T67 | D1251, Q926, N497 | D1251, Q926, R661 | D1251, Q926, Q695 | |
| D23, Q926, Y128 | D1251, Q926, Y128 | | Y128, Q926, T67 | Y128, Q926, N497 | Y128, Q926, R661 | Y128, Q926, Q695 |
| D23, Q926, T67 | D1251, Q926, T67 | Y128, Q926, T67 | | T67, Q926, N497 | T67, Q926, R661 | T67, Q926, Q695 |
| D23, Q926, N497 | D1251, Q926, N497 | Y128, Q926, N497 | T67, Q926, N497 | | N497, Q926, R661 | N497, Q926, Q695 |
| D23, Q926, R661 | D1251, Q926, R661 | Y128, Q926, R661 | T67, Q926, R661 | N497, Q926, R661 | | R661, Q926, Q695 |
| D23, Q926, Q695 | D1251, Q926, Q695 | Y128, Q926, Q695 | T67, Q926, Q695 | N497, Q926, Q695 | R661, Q926, Q695 | |

Without limiting the foregoing, the present disclosure encompasses the following mutants:

D23A (Mutant 1)
Y128V
D1251G (Mutant 2)
T67L (Mutant 3)
D23A, Y128V (Mutant 4)
D23A, D1251G (Mutant 5)
D23A, Y128V, D1251G, T67L (Mutant 6)
N497A/R661A/Q695A/Q926A (Mutant 7)

This disclosure also encompasses genome editing systems comprising a mutant S. pyogenes Cas9 as described herein.

The isolated SpCas9 variant proteins described herein are, in certain embodiments of this disclosure, fused to a heterologous functional domain, with an optional intervening linker, wherein the linker does not interfere with activity of the fusion protein. In some embodiments, the heterologous functional domain is a transcriptional activation domain. In some embodiments, the transcriptional activation domain is from VP64 or NF-kappa B p65. In some embodiments, the heterologous functional domain is a transcriptional silencer or transcriptional repression domain. In some embodiments, the transcriptional repression domain is a Krueppel-associated box (KRAB) domain, ERF repressor domain (ERD), or mSin3A interaction domain (SID). In some embodiments, the transcriptional silencer is Heterochromatin Protein 1 (HP1), e.g., HP1 alpha. or HP1 beta. In some embodiments, the heterologous functional domain is an enzyme that modifies the methylation state of DNA. In some embodiments, the enzyme that modifies the methylation state of DNA is a DNA methyltransferase (DNMT) or a TET protein. In some embodiments, the TET protein is TET1. In some embodiments, the heterologous functional domain is an enzyme that modifies a histone subunit. In some embodiments, the enzyme that modifies a histone subunit is a histone acetyltransferase (HAT), histone deacetylase (HDAC), histone methyltransferase (HMT), or histone demethylase. In some embodiments, the heterologous functional domain is a biological tether. In some embodiments, the biological tether is MS2, Csy4 or lambda N protein. In some embodiments, the heterologous functional domain is Fok1.

In addition to encompassing isolated nucleic acids encoding the variant SpCas9 proteins described herein, this disclosure encompasses both viral and non-viral vectors comprising such isolated nucleic acids, which are optionally operably linked to one or more regulatory domains for expressing the variant SpCas9 proteins described herein. The disclosure also includes host cells, e.g., mammalian host cells, comprising the nucleic acids described herein, and optionally expressing one or more of the variant SpCas9 proteins described herein.

The variant SpCas9 proteins described herein may be used to alter the genome of a cell, for example by expressing in the cell an isolated variant SaCas9 or SpCas9 protein described herein, and a guide RNA having a region complementary to a selected portion of the genome of the cell. Alternatively or additionally, this disclosure further encompasses methods for altering, e.g., selectively altering, the genome of a cell by contacting the cell with a protein variant described herein, and a guide RNA having a region complementary to a selected portion of the genome of the cell. In some embodiments, the cell is a stem cell, e.g., an embryonic stem cell, mesenchymal stem cell, or induced pluripotent stem cell; is in a living animal; or is in an embryo, e.g., a mammalian, insect, or fish (e.g., zebrafish) embryo or embryonic cell.

In some embodiments, the isolated protein or fusion protein comprises one or more of a nuclear localization sequence, cell penetrating peptide sequence, and/or affinity tag.

Further, this disclosure encompasses methods, e.g., in vitro methods, ex vivo and in vivo methods, for altering a double stranded DNA (dsDNA) molecule in a cell. The methods include contacting the dsDNA molecule with one or more of the variant proteins described herein, and a guide RNA having a region complementary to a selected portion of the dsDNA molecule.

Example 5: Evolution of S. pyogenes Cas9 to Reduce Off Target Cutting

Figure 11:
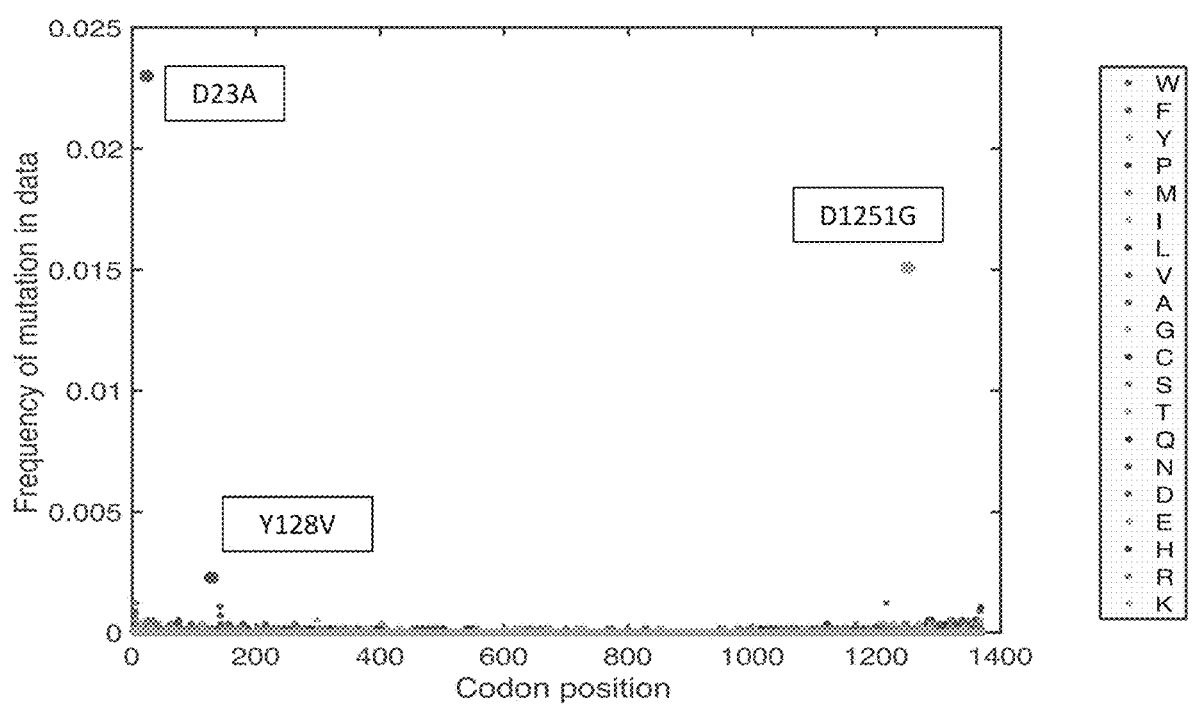
FIG. 11 depicts the frequency of mutations in variant S. pyogenes Cas9 polypeptides by codon position and according to amino acid substitution.

The systems and methods of this disclosure can be employed to select for a variety of nuclease characteristics, as will be further illustrated by the following example. Using the selection method disclosed herein, S. pyogenes cas9 variants have been identified from a mutagenized library which have maintained on-target cleavage efficiency but have reduced cutting at off-target loci, providing a means to potentially rescue promiscuous guides for therapeutic use. Mutant S. pyogenes Cas9 libraries were generated using scanning mutagenesis at random targets (SMART). Libraries were then transformed into E. coli and challenged with phage for three rounds of both positive and negative selection (FIGS. 1 and 2). Following positive and negative selection steps, clones were selected and sequenced by next generation sequencing (NGS), and reads were aligned to identify the most commonly mutated amino acid residues relative to the unmutated S. pyogenes Cas9 (SEQ ID NO: 13). The frequency of the identified mutations, by codon position and according to amino acid substitution was determined (FIG. 11). Mutations were identified in the RuvC domain (e.g., D23A), the REC domain (e.g., T67L, Y128V) and the PAM interacting domain (PI) (e.g., D1251G). Expression constructs comprising combinations of 4 different mutations (D23A, T67L, Y128V and D1251 G) were prepared and tested in vitro for on-target and off-target editing efficiency in human T cells. In this example, the construct comprising mutations D23A, Y128V, D1251 G and T67L was designated "Mut6" or "SpartaCas".

Figure 12:
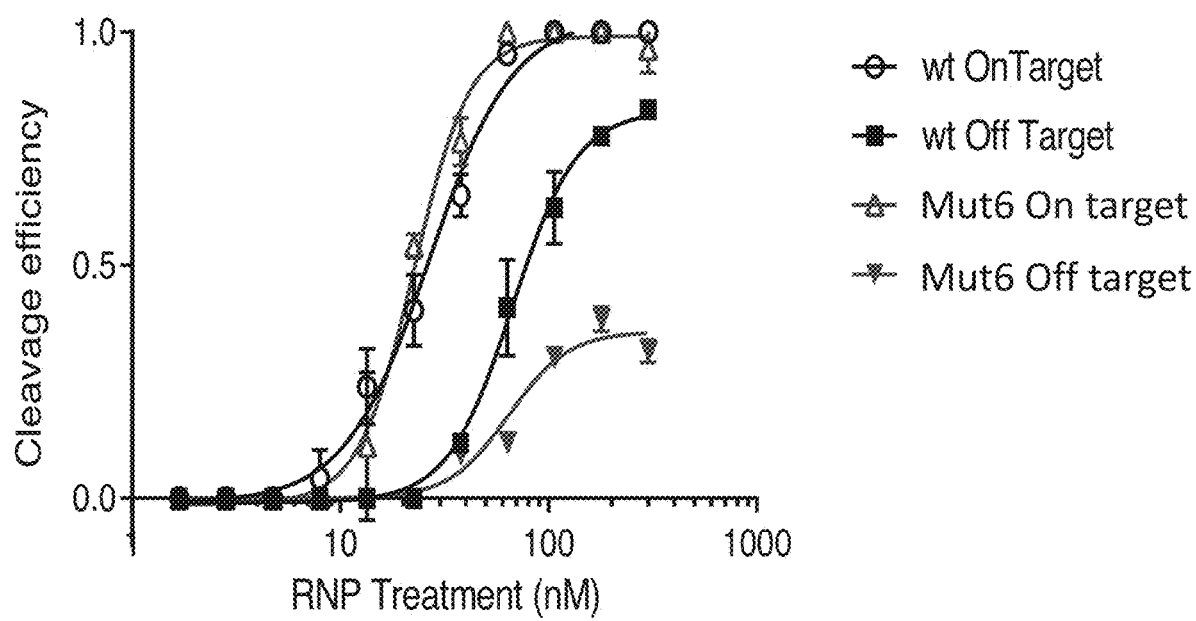
FIG. 12 depicts results of an in vitro editing assay in which cleavage of an on-target genomic sequence and a known off-target genomic sequence are assessed in human T cells treated with increasing doses of wild-type S. pyogenes Cas9 or a variant Cas9/guide RNA ribonucleoprotein complex (RNP).

An in vitro dose response study was performed using Mut6 and wild-type S. pyogenes Cas9 for genomic on- and off-target loci in T cells, as shown in FIG. 12. Wild-type or mutant Cas9/guide RNA ribonucleoprotein complexes (RNPs) were delivered at different concentrations across a >2 log range. As illustrated in FIG. 12, the Mut6 construct exhibited on-target cutting activity comparable to wild-type S. pyogenes Cas9, while also exhibiting substantially lower off-target cleavage than wild-type.

Figure 13:
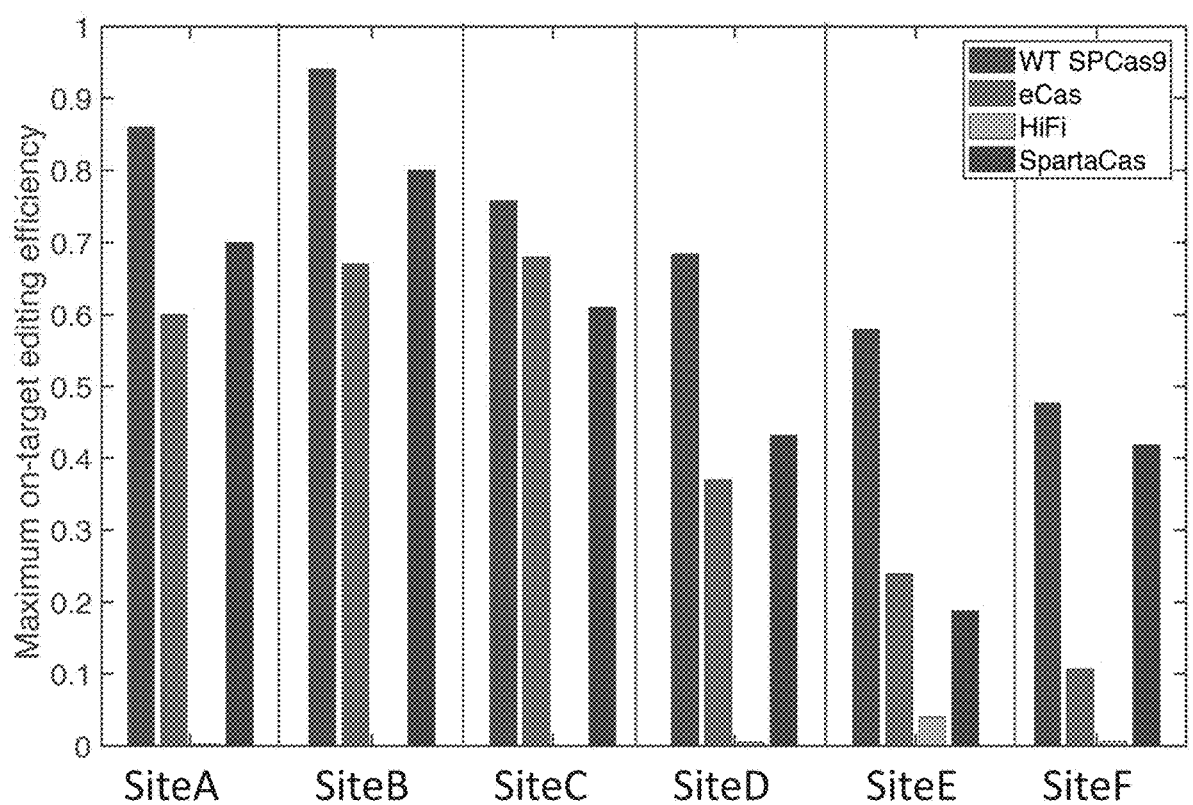
FIG. 13 depicts results of an in vitro editing assay in which cleavage of on-target genomic sequences was assessed in human T cells treated with RNP comprising wild-type S. pyogenes Cas9 (WT SPCas9) or one of three different variant Cas9 proteins.

On target editing at 6 different loci (SiteA, SiteB, SiteC, SiteD, SiteE, and SiteF) was evaluated using wild-type S. pyogenes Cas9 (WT SPCas9), "SpartaCas" (Mut 6) and two known mutant S. pyogenes Cas9 proteins, eCas (Slaymaker et al. Science (2015) 351:84-88) and HF1 Cas9 (Kleinstiver et al. Nature (2016) 529: 490-495). Either 1 μm (locus 1 and 2) or 5 μm (locus 3-6) wild-type or mutant Cas9/guide RNA RNPs was delivered to human T cells. Editing efficiency was locus dependent. The editing efficiency of SpartaCas was higher than that of HF1 Cas9 at all loci and higher than that of eCas at 4 of the 6 loci (FIG. 13).

Figure 14A:
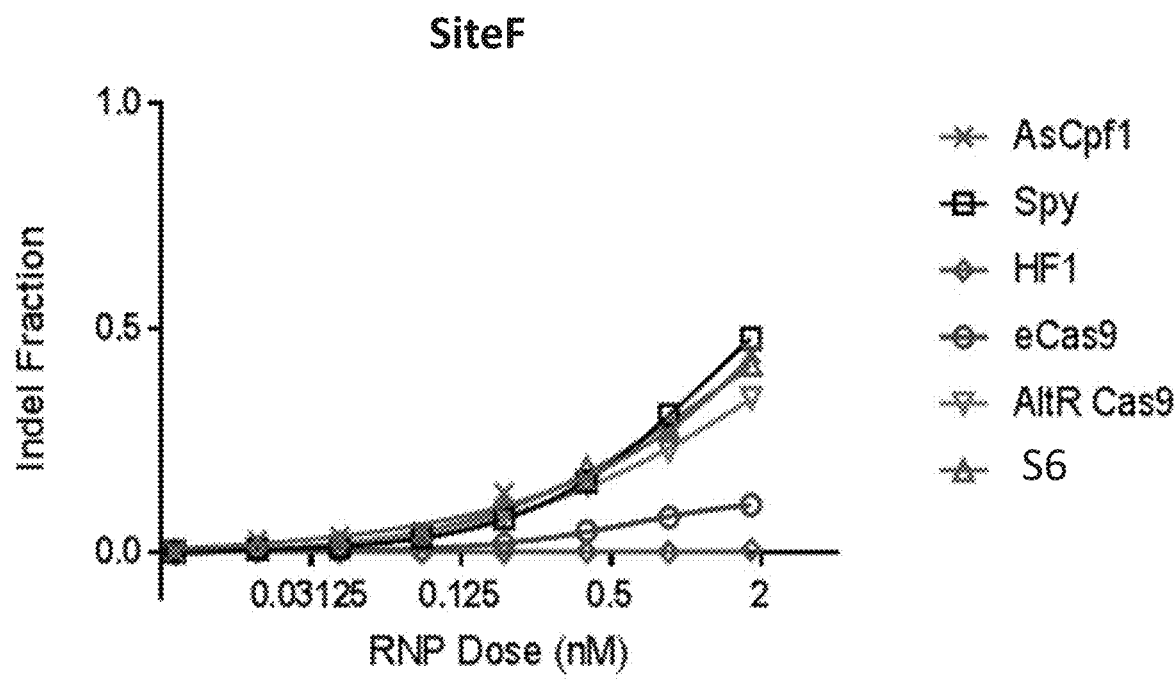
FIGS. 14A-14C depict results of an in vitro editing assay in which cleavage of three on-target genomic sequences was assessed in human T cells treated with increasing doses of RNP comprising wild-type or variant Cas9 proteins.
Figure 14B:
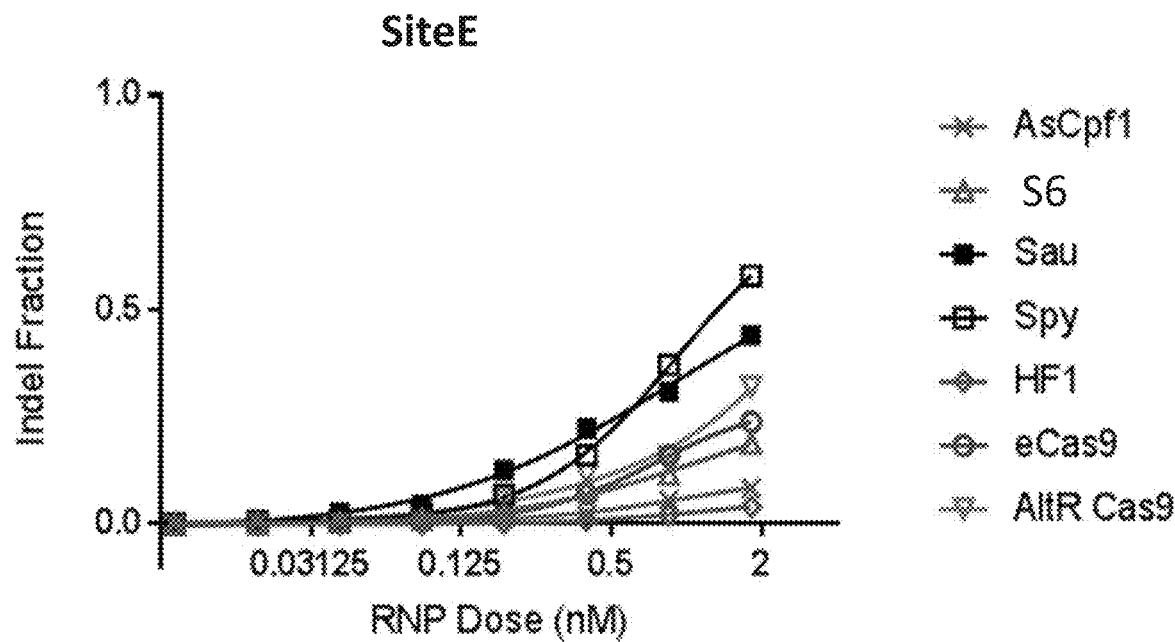
Figure 14C:
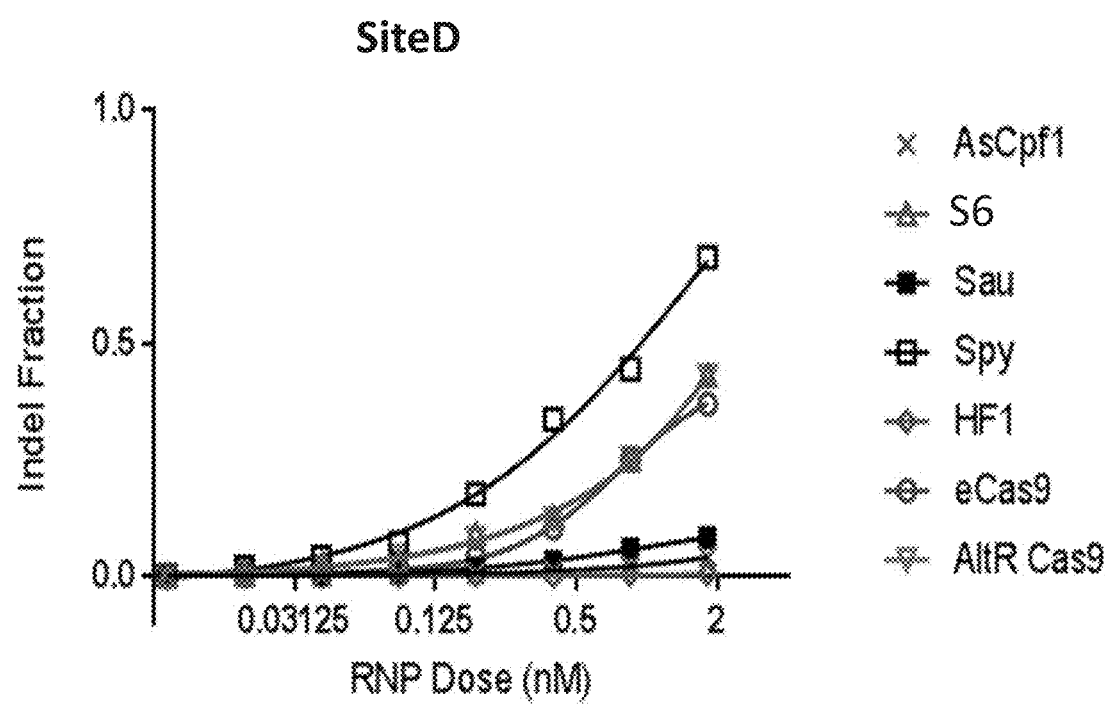

Further on-target editing dose response studies were performed using wild-type S. pyogenes Cas9 ("Spy"), wild-type S. aureus Cas9 ("Sau"), wild-type Acidaminococcus Cpf1 ("AsCpf1"), SpartaCas ("Mut6" or "S6") and alternative mutant S. pyogenes Cas9 proteins including HF1 Cas9, eCas9 and Alt-R® Cas9 ("AltR Cas9") (www.idtdna.com) in human T cells. On-target editing was target dependent and SpartaCas demonstrated high efficiency of on-target editing (FIGS. 14A-14C).

Figure 15A:
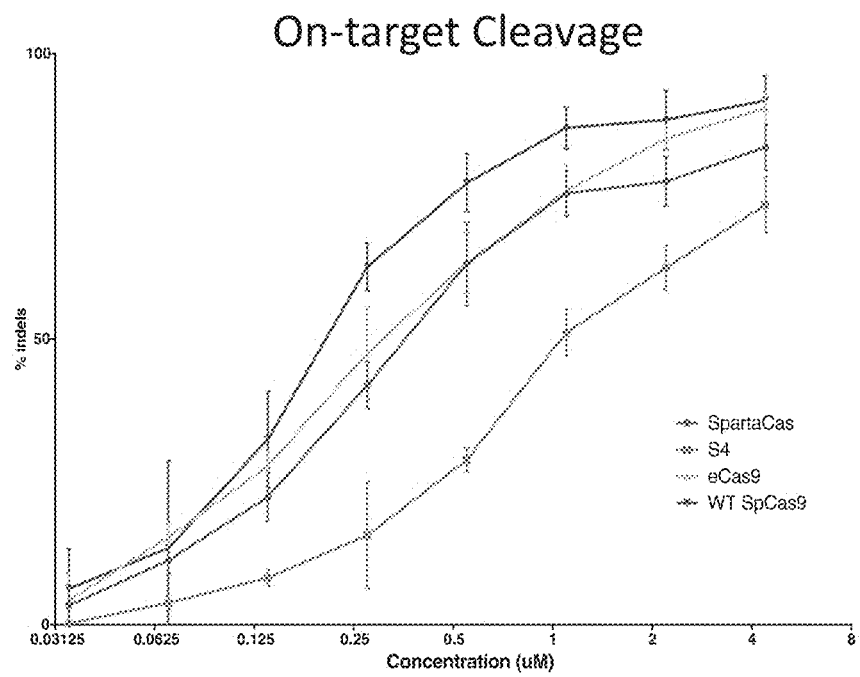
FIGS. 15A and 15B depict results of an in vitro editing assay in which cleavage of an on-target genomic sequence (FIG. 15A) and a known off-target genomic sequence (FIG. 15B) are assessed in human T cells treated with increasing doses of wild-type S. pyogenes Cas9 ("SpCas9") or one of three different variant Cas9/guide RNA ribonucleoprotein complex (RNP).
Figure 15B:
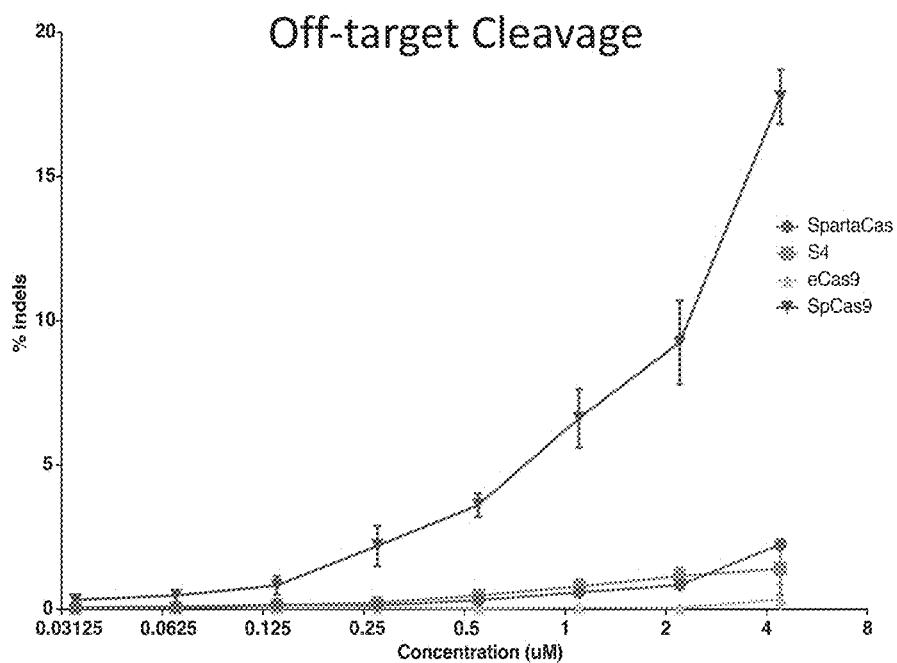

SpartaCas (Mut6) was further evaluated for on-target and off-target cleavage efficiency at RNP doses ranging from 0.03125 μM to 4 μM. On-target cleavage was comparable to wild-type S. pyogenes Cas9 while off-target cleavage was significantly decreased (FIG. 15).

Example 6: Assessment of Off-Target Cutting by S. pyogenes Cas9 Variants Using GUIDE Seq Off-target cutting by wild-type Cas9, eCas, and SpartaCas was assessed using GUIDE-Seq, using the following method.

Complexation of RNPs

RNPs were complexed with two-part gRNA synthesized by Integrated DNA Technologies. All guides were annealed to a final concentration of 200 uM, with a 1:1 ratio of crRNA to tracrRNA. RNPs were complexed to achieve a 1:2 enzyme to guide ratio. A 1:1 volumetric ratio with 100 uM enzyme and 200 uM gRNA was used to achieve a final RNP concentration of 50 uM. The RNPs were allowed to complex for 30 minutes at room temperature. The RNPs were then serially diluted 2-fold across eight concentrations. RNPs were frozen down at −80° C. until nucleofection.

Culture of T-Cells

T-Cells were cultured with Lonza X-Vivo 15 media. The cells were thawed and cultured with Dynabeads Human T-Activator CD3/CD28 for T Cell Expansion and Activation. On day two post thaw the cells were removed from the beads. The cells continued to be cultured to day 4, upon which they were spun down for nucleofection. On day 2 post nucleofection the cell volume was divided in half into a new plate so that they had continued room to expand.

T-Cell Nucleofection

Cells were counted using a BioRad T-20 cell counter. Cells were mixed 1:1 with trypan blue and counted. The total amount of cells needed (enough for 500k cells per well) were aliquoted to a separate tube and then spun down at 1500 RPM for 5 minutes. The cells were then resuspended in Lonza P2 nucleofection solution. The cells were then plated at 20 uL per well in the Lonza 96 well nucleofection plate. Cells and RNP plates were then brought over to a BioMek FX robot. Using the 96-well head 2 µL of each RNP was transferred and mixed into the nucleofection plate. The nucleofection plate was then immediately brought over to the Lonza shuttle system where it was nucleofected with the DS-130 pulse code. Cells were then immediately brought back to the BioMek FX where they were transferred to a pre-warmed 96-well nontreated media plate and mixed. The cell plate was then placed at 37° C. for incubation.

gDNA Extraction

On day 4, cells were spun down in their plates at 2000 RPM for 5 minutes. The media was then decanted. The cell pellets were then resuspended in Agencourt DNAdvance lysis solution. The gDNA was extracted using the DNAdvance protocol on the BioMek FX.

GUIDE-seq

GUIDE-seq was performed based on the protocol of Tsai et al. (*Nat. Biotechnol.* 33:187-197 (2015)) and adapted to T-cells as follows. 10 uL 4.4 uM of RNP were combined with 4 µL of 100 uM dsODN, and 6 µL of 1×H150 buffer for a total volume of the 20 uL. RNPs were placed on ice until nucleofection. T-cells were counted using the BioRad T-20 cell counter. Cells were mixed 1:1 with trypan blue and counted. The total amount of cells needed (enough for 2 million cells per cuvette) were aliquoted to a separate tube and then spun down at 1500 RPM for 5 minutes. The cells were then resuspended in 80 µL of Lonza P2 solution. Cells were then pipetted into their respective cuvettes, and the 20 µL of RNP/dsODN were added to each cuvette, and the whole solution was gently mixed. Cells were then nucleofected using the CA-137 pulse code. Cells were then immediately pipetted into a pre-warmed noncoated media plate. The cell plate was then placed at 37° C. for incubation. gDNA was extracted and analyzed using the protocol of Tsai et al. (Nat. Biotechnol. 33:187-197 (2015)), using only bidirectional reads.

Results

Figure 18A:
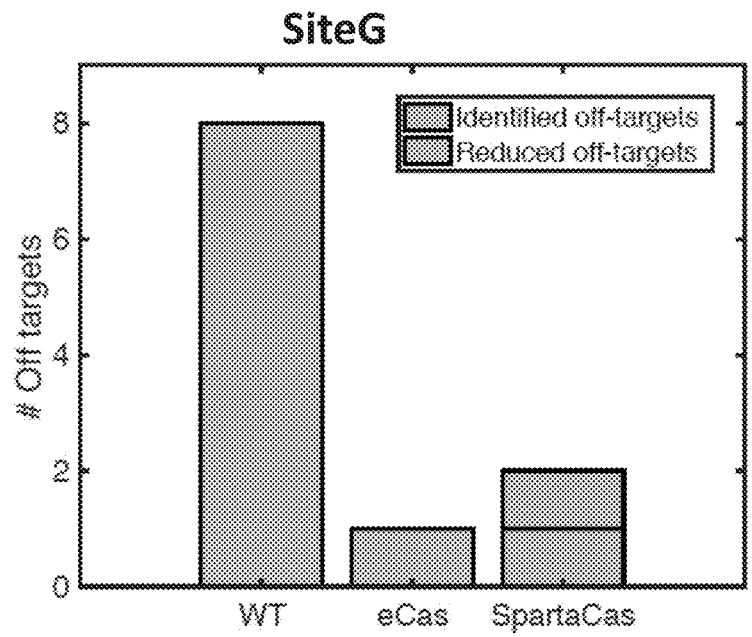
FIGS. 18A and 18B depict off-target cutting for wild-type Cas9 and two Cas9 variants.
Figure 18B:
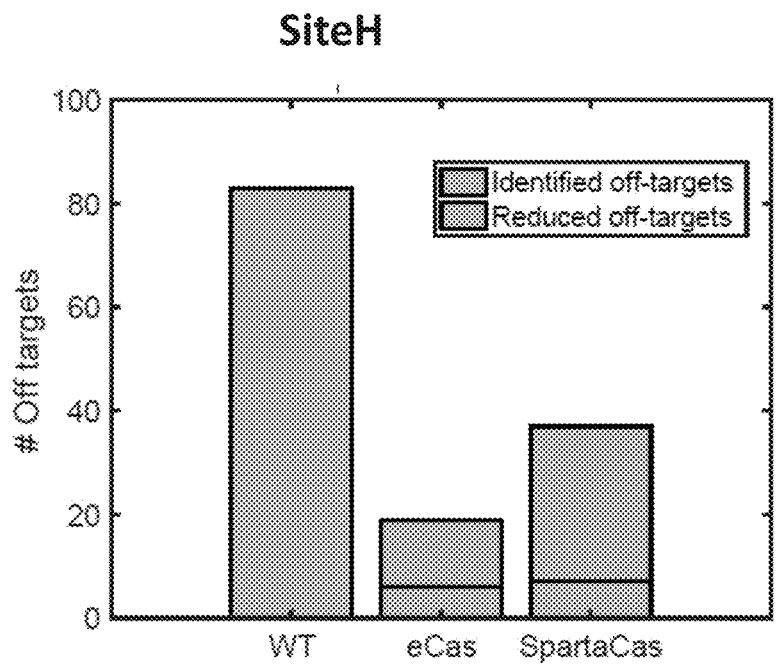

FIGS. 18A and 18B depict off-target cutting for "SiteG" and "SiteH", respectively. As shown in FIGS. 18A and 18B, SpartaCas and eCas both reduced total numbers of off-targets, relative to wild-type Cas9. Further, most of the off-targets that remained had decreased read counts (shown in cyan).

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

| SEQUENCE LISTING |
|---|
| An exemplary codon optimized nucleic acid sequence encoding a Cas9 molecule of S. pyogenes (SEQ ID NO: 9). |

| | | | | | |
|---|---|---|---|---|---|
| atggataaaa | agtacagcat | cgggctggac | atcggtacaa | actcagtggg | gtgggccgtg | 60 |
| attacggacg | agtacaaggt | accctccaaa | aaatttaaag | tgctgggtaa | cacggacaga | 120 |
| cactctataa | agaaaaatct | tattggagcc | ttgctgttcg | actcaggcga | gacagccgaa | 180 |
| gccacaaggt | tgaagcggac | cgccaggagg | cggtatacca | ggagaaagaa | ccgcatatgc | 240 |
| tacctgcaag | aaatcttcag | taacgagatg | gcaaaggttg | acgatagctt | tttccatcgc | 300 |
| ctggaagaat | cctttcttgt | tgaggaagac | aagaagcacg | aacggcaccc | catctttggc | 360 |
| aatattgtcg | acgaagtggc | atatcacgaa | aagtacccga | ctatctacca | cctcaggaag | 420 |
| aagctggtgg | actctaccga | taaggcggac | ctcagactta | tttatttggc | actcgcccac | 480 |
| atgattaaat | ttagaggaca | tttcttgatc | gagggcgacc | tgaacccgga | caacagtgac | 540 |
| gtcgataagc | tgttcatcca | acttgtgcag | acctacaatc | aactgttcga | agaaaaccct | 600 |
| ataaatgctt | caggagtcga | cgctaaagca | atcctgtccg | cgcgcctctc | aaaatctaga | 660 |
| agacttgaga | atctgattgc | tcagttgccc | ggggaaaaga | aaaatggatt | gtttggcaac | 720 |
| ctgatcgccc | tcagtctcgg | actgacccca | aatttcaaaa | gtaacttcga | cctggccgaa | 780 |

```
gacgctaagc tccagctgtc caaggacaca tacgatgacg acctcgacaa tctgctggcc      840
cagattgggg atcagtacgc cgatctcttt ttggcagcaa agaacctgtc cgacgccatc      900
ctgttgagcg atatcttgag agtgaacacc gaaattacta agcacccct tagcgcatct       960 atgatcaagc ggtacgacga gcatcatcag gatctgaccc tgctgaaggc tcttgtgagg     1020
caacagctcc ccgaaaaata caaggaaatc ttctttgacc agagcaaaaa cggctacgct     1080
ggctatatag atggtggggc cagtcaggag gaattctata aattcatcaa gcccattctc     1140
gagaaaatgg acggcacaga ggagttgctg gtcaaactta cagggagga cctgctgcgg     1200 aagcagcgga cctttgacaa cgggtctatc ccccaccaga ttcatctggg cgaactgcac     1260
gcaatcctga ggaggcagga ggatttttat cctttttta aagataaccg cgagaaaata     1320
gaaaagattc ttacattcag gatcccgtac tacgtgggac ctctcgcccg gggcaattca     1380
cggtttgcct ggatgacaag gaagtcagag gagactatta caccttggaa cttcgaagaa     1440
gtggtggaca agggtgcatc tgcccagtct ttcatcgagc ggatgacaaa ttttgacaag     1500
aacctcccta tgagaaggt gctgcccaaa cattctctgc tctacgagta ctttaccgtc     1560
tacaatgaac tgactaaagt caagtacgtc accgagggaa tgaggaagcc ggcattcctt     1620
agtggagaac agaagaaggc gattgtagac ctgttgttca agaccaacag gaaggtgact     1680
gtgaagcaac ttaaagaaga ctactttaag aagatcgaat gttttgacag tgtggaaatt     1740
tcaggggttg aagaccgctt caatgcgtca ttggggactt accatgatct tctcaagatc     1800
ataaaggaca aagacttcct ggacaacgaa gaaaatgagg atattctcga agacatcgtc     1860 ctcacccctga ccctgttcga agacaggaa atgatagaag agcgcttgaa aacctatgcc     1920
cacctcttcg acgataaagt tatgaagcag ctgaagcgca ggagatacac aggatgggga     1980
agattgtcaa ggaagctgat caatggaatt gggataaac agagtggcaa gaccatactg     2040
gatttcctca atctgatgg cttcgccaat aggaacttca tgcaactgat tcacgatgac     2100
tctcttacct tcaaggagga cattcaaaag gctcaggtga gcgggcaggg agactccctt     2160
catgaacaca tcgcgaattt ggcaggttcc cccgctatta aaaagggcat ccttcaaact     2220
gtcaaggtgg tggatgaatt ggtcaaggta atgggcagac ataagccaga aaatattgtg     2280
atcgagatgg cccgcgaaaa ccagaccaca cagaagggcc agaaaaatag tagagagcgg     2340
atgaagagga tcgaggaggg catcaaagag ctgggatctc agattctcaa gaacaccccc     2400
gtagaaaaca cacagctgca gaacgaaaaa ttgtacttgt actatctgca gaacggcaga     2460
gacatgtacg tcgaccaaga acttgatatt aatagactgt ccgactatga cgtagaccat     2520
atcgtgcccc agtccttcct gaaggacgac tccattgata caaagtctt gacaagaagc     2580 gacaagaaca ggggtaaaag tgataatgtg cctagcgagg aggtggtgaa aaaaatgaag     2640
aactactggc gacagctgct taatgcaaag ctcattacac aacggaagtt cgataatctg     2700
acgaaagcag agagaggtgg cttgtctgag ttggacaagg cagggtttat taagcggcag     2760
ctggtggaaa ctaggcagat cacaaagcac gtggcgcaga ttttggacag ccggatgaac     2820
acaaaatacg acgaaaatga taaactgata cgagaggtca agttatcac gctgaaaagc     2880 aagctggtgt ccgatttcg gaaagacttc cagttctaca agttcgcga gattaataac     2940 taccatcatg ctcacgatgc gtacctgaac gctgttgtcg gaccgccctt gataaagaag     3000
tacccaaagc tggaatccga gttcgtatac ggggattaca agtgtacga tgtgaggaaa     3060
```

| | |
|---|---|
| atgatagcca agtccgagca ggagattgga aaggccacag ctaagtactt cttttattct | 3120 |
| aacatcatga atttttttaa gacggaaatt accctggcca acggagagat cagaaagcgg | 3180 |
| cccctttatag agacaaatgg tgaaacaggt gaaatcgtct gggataaggg cagggatttc | 3240 |
| gctactgtga ggaaggtgct gagtatgcca caggtaaata tcgtgaaaaa aaccgaagta | 3300 |
| cagaccggag gattttccaa ggaaagcatt ttgcctaaaa gaaactcaga caagctcatc | 3360 |
| gcccgcaaga aagattggga ccctaagaaa tacgggggat ttgactcacc caccgtagcc | 3420 |
| tattctgtgc tggtggtagc taaggtggaa aaaggaaagt ctaagaagct gaagtccgtg | 3480 |
| aaggaactct tgggaatcac tatcatggaa agatcatcct ttgaaaagaa ccctatcgat | 3540 |
| ttcctggagg ctaagggtta caaggaggtc aagaaagacc tcatcattaa actgccaaaa | 3600 |
| tactctctct tcgagctgga aaatggcagg aagagaatgt tggccagcgc cggagagctg | 3660 |
| caaaagggaa acgagcttgc tctgccctcc aaatatgtta attttctcta tctcgcttcc | 3720 |
| cactatgaaa agctgaaagg gtctcccgaa gataacgagc agaagcagct gttcgtcgaa | 3780 |
| cagcacaagc actatctgga tgaaataatc gaacaaataa gcgagttcag caaaagggtt | 3840 |
| atcctggcgg atgctaattt ggacaaagta ctgtctgctt ataacaagca ccgggataag | 3900 |
| cctattaggg aacaagccga gaatataatt cacctcttta cactcacgaa tctcggagcc | 3960 |
| cccgccgcct tcaaatactt tgatacgact atcgaccgga acggtatac cagtaccaaa | 4020 |
| gaggtcctcg atgccaccct catccaccag tcaattactg gcctgtacga aacacggatc | 4080 |
| gacctctctc aactgggcgg cgactag | 4107 |
| An exemplary codon optimized nucleic acid sequences encoding a Cas9 molecule of S. aureus (SEQ ID NO: 10). | |
| atgaaaagga actacattct ggggctggac atcgggatta caagcgtggg gtatgggatt | 60 |
| attgactatg aaacaaggga cgtgatcgac gcaggcgtca gactgttcaa ggaggccaac | 120 |
| gtggaaaaca atgagggacg gagaagcaag aggggagcca ggcgcctgaa acgacggaga | 180 |
| aggcacagaa tccagagggt gaagaaactg ctgttcgatt acaacctgct gaccgaccat | 240 |
| tctgagctga gtggaattaa tccttatgaa gccagggtga aaggcctgag tcagaagctg | 300 |
| tcagaggaag agttttccgc agctctgctg cacctggcta agcgccgagg agtgcataac | 360 |
| gtcaatgagg tggaagagga caccggcaac gagctgtcta caaaggaaca gatctcacgc | 420 |
| aatagcaaag ctctggaaga gaagtatgtc gcagagctgc agctggaacg gctgaagaaa | 480 |
| gatggcgagg tgagagggtc aattaatagg ttcaagacaa gcgactacgt caaagaagcc | 540 |
| aagcagctgc tgaaagtgca aaaggcttac caccagctgg atcagagctt catcgatact | 600 |
| tatatcgacc tgctggagac tcggagaacc tactatgagg gaccaggaga agggagccccc | 660 |
| ttcggatgga aagacatcaa ggaatggtac gagatgctga tgggacattg cacctatttt | 720 |
| ccagaagagc tgagaagcgt caagtacgct tataacgcag atctgtacaa cgccctgaat | 780 |
| gacctgaaca acctggtcat caccagggat gaaaacgaga actggaata ctatgagaag | 840 |
| ttccagatca tcgaaaacgt gtttaagcag aagaaaaagc ctacactgaa acagattgct | 900 |
| aaggagatcc tggtcaacga agaggacatc aagggctacc gggtgacaag cactggaaaa | 960 |
| ccagagttca ccaatctgaa agtgtatcac gatattaagg acatcacagc acggaaagaa | 1020 |
| atcattgaga cgccgaact gctggatcag attgctaaga tcctgactat ctaccagagc | 1080 |
| tccgaggaca tccaggaaga gctgactaac ctgaacagcg agctgaccca ggaagagatc | 1140 |
| gaacagatta gtaatctgaa ggggtacacc ggaacacaca acctgtccct gaaagctatc | 1200 |

| | |
|---|---|
| aatctgattc tggatgagct gtggcataca aacgacaatc agattgcaat ctttaaccgg | 1260 |
| ctgaagctgg tcccaaaaaa ggtggacctg agtcagcaga agagatccc aaccacactg | 1320 |
| gtggacgatt tcattctgtc acccgtggtc aagcggagct tcatccagag catcaaagtg | 1380 |
| atcaacgcca tcatcaagaa gtacggcctg cccaatgata tcattatcga gctggctagg | 1440 |
| gagaagaaca gcaaggacgc acagaagatg atcaatgaga tgcagaaacg aaaccggcag | 1500 |
| accaatgaac gcattgaaga gattatccga actaccggga agagaacgc aaagtacctg | 1560 |
| attgaaaaaa tcaagctgca cgatatgcag gagggaaagt gtctgtattc tctggaggcc | 1620 |
| atcccctgg aggacctgct gaacaatcca ttcaactacg aggtcgatca tattatcccc | 1680 |
| agaagcgtgt ccttcgacaa ttcctttaac aacaaggtgc tggtcaagca ggaagagaac | 1740 |
| tctaaaaagg gcaataggac tccttccag tacctgtcta gttcagattc caagatctct | 1800 |
| tacgaaacct ttaaaaagca cattctgaat ctggccaaag gaagggccg catcagcaag | 1860 |
| accaaaaagg agtacctgct ggaagagcgg gacatcaaca gattctccgt ccagaaggat | 1920 |
| tttattaacc ggaatctggt ggacacaaga tacgctactc gcggcctgat gaatctgctg | 1980 |
| cgatcctatt tccgggtgaa caatctggat gtgaaagtca agtccatcaa cggcgggttc | 2040 |
| acatctttc tgaggcgcaa atggaagttt aaaaaggagc gcaacaaagg gtacaagcac | 2100 |
| catgccgaag atgctctgat tatcgcaaat gccgacttca tctttaagga gtggaaaaag | 2160 |
| ctggacaaag ccaagaaagt gatggagaac cagatgttcg aagagaagca ggccgaatct | 2220 |
| atgcccgaaa tcgagacaga acaggagtac aaggagattt tcatcactcc tcaccagatc | 2280 |
| aagcatatca aggatttcaa ggactacaag tactctcacc gggtggataa aaagcccaac | 2340 |
| agagagctga tcaatgacac cctgtatagt acaagaaaag acgataaggg gaatacctg | 2400 |
| attgtgaaca atctgaacgg actgtacgac aaagataatg acaagctgaa aaagctgatc | 2460 |
| aacaaaagtc ccgagaagct gctgatgtac caccatgatc ctcagacata tcagaaactg | 2520 |
| aagctgatta tggagcagta cggcgacgag aagaacccac tgtataagta ctatgaagag | 2580 |
| actgggaact acctgaccaa gtatagcaaa aggataatg gccccgtgat caagaagatc | 2640 |
| aagtactatg gaacaagct gaatgcccat ctggacatca cagacgatta ccctaacagt | 2700 |
| cgcaacaagg tggtcaagct gtcactgaag ccatacagat cgatgtcta tctggacaac | 2760 |
| ggcgtgtata aatttgtgac tgtcaagaat ctggatgtca tcaaaaagga gaactactat | 2820 |
| gaagtgaata gcaagtgcta cgaagaggct aaaaagctga aaaagattag caaccaggca | 2880 |
| gagttcatcg cctcctttta caacaacgac ctgattaaga tcaatggcga actgtatagg | 2940 |
| gtcatcgggg tgaacaatga tctgctgaac cgcattgaag tgaatatgat tgacatcact | 3000 |
| taccgagagt atctggaaaa catgaatgat aagcgccccc ctcgaattat caaaacaatt | 3060 |
| gcctctaaga ctcagagtat caaaaagtac tcaaccgaca ttctgggaaa cctgtatgag | 3120 |
| gtgaagagca aaaagcaccc tcagattatc aaaaagggc | 3159 |

An exemplary codon optimized nucleic acid sequences encoding a Cas9 molecule of S. aureus (SEQ ID NO: 11).

| | |
|---|---|
| atgaagcgga actacatcct gggcctggac atcggcatca ccagcgtggg ctacggcatc | 60 |
| atcgactacg agacacggga cgtgatcgat gccggcgtgc ggctgttcaa agaggccaac | 120 |
| gtggaaaaca cgagggcag gcggagcaag agaggcgcca aaggctgaa gcggcggagg | 180 |
| cggcatagaa tccagagagt gaagaagctg ctgttcgact acaacctgct gaccgaccac | 240 |

SEQUENCE LISTING

| | | | | |
|---|---|---|---|---|
| agcgagctga | gcggcatcaa | cccctacgag | gccagagtga | agggcctgag ccagaagctg | 300 |
| agcgaggaag | agttctctgc | cgccctgctg | cacctggcca | agagaagagg cgtgcacaac | 360 |
| gtgaacgagg | tggaagagga | caccggcaac | gagctgtcca | ccaaagagca gatcagccgg | 420 |
| aacagcaagg | ccctggaaga | gaaatacgtg | gccgaactgc | agctggaacg gctgaagaaa | 480 |
| gacggcgaag | tgcggggcag | catcaacaga | ttcaagacca | gcgactacgt gaaagaagcc | 540 |
| aaacagctgc | tgaaggtgca | gaaggcctac | caccagctgg | accagagctt catcgacacc | 600 |
| tacatcgacc | tgctgaaaac | ccggcggacc | tactatgagg | acctggcga gggcagcccc | 660 |
| ttcggctgga | aggacatcaa | agaatggtac | gagatgctga | tgggccactg cacctacttc | 720 |
| cccgaggaac | tgcggagcgt | gaagtacgcc | tacaacgccg | acctgtacaa cgccctgaac | 780 |
| gacctgaaca | atctcgtgat | caccagggac | gagaacgaga | agctggaata ttacgagaag | 840 |
| ttccagatca | tcgagaacgt | gttcaagcag | aagaagaagc | ccacccctgaa gcagatcgcc | 900 |
| aaagaaatcc | tcgtgaacga | agaggatatt | aagggctaca | gagtgaccag caccggcaag | 960 |
| cccgagttca | ccaacctgaa | ggtgtaccac | gacatcaagg | acattaccgc ccggaaagag | 1020 |
| attattgaga | cgccgagct | gctggatcag | attgccaaga | tcctgaccat ctaccagagc | 1080 |
| agcgaggaca | tccaggaaga | actgaccaat | ctgaactccg | agctgaccca ggaagagatc | 1140 |
| gagcagatct | ctaatctgaa | gggctatacc | ggcacccaca | acctgagcct gaaggccatc | 1200 |
| aacctgatcc | tggacgagct | gtggcacacc | aacgacaacc | agatcgctat cttcaaccgg | 1260 |
| ctgaagctgg | tgcccaagaa | ggtggacctg | tcccagcaga | aagagatccc caccaccctg | 1320 |
| gtggacgact | tcatcctgag | ccccgtcgtg | aagagaagct | tcatccagag catcaaagtg | 1380 |
| atcaacgcca | tcatcaagaa | gtacggcctg | cccaacgaca | tcattatcga gctggcccgc | 1440 |
| gagaagaact | ccaaggacgc | ccagaaaatg | atcaacgaga | tgcagaagcg gaaccggcag | 1500 |
| accaacgagc | ggatcgagga | aatcatccgg | accaccggca | aagagaacgc caagtacctg | 1560 |
| atcgagaaga | tcaagctgca | cgacatgcag | gaaggcaagt | gcctgtacag cctggaagcc | 1620 |
| atccctctgg | aagatctgct | gaacaacccc | ttcaactatg | aggtggacca catcatcccc | 1680 |
| agaagcgtgt | ccttcgacaa | cagcttcaac | aacaaggtgc | tcgtgaagca ggaagaaaac | 1740 |
| agcaagaagg | gcaaccggac | cccattccag | tacctgagca | gcagcgacag caagatcagc | 1800 |
| tacgaaacct | tcaagaagca | catcctgaat | ctggccaagg | gcaagggcag aatcagcaag | 1860 |
| accaagaaag | agtatctgct | ggaagaacgg | gacatcaaca | ggttctccgt gcagaaagac | 1920 |
| ttcatcaacc | ggaacctggt | ggataccaga | tacgccacca | gaggcctgat gaacctgctg | 1980 |
| cggagctact | tcagagtgaa | caacctggac | gtgaaagtga | agtccatcaa tggcggcttc | 2040 |
| accagctttc | tgcggcggaa | gtggaagttt | aagaaagagc | ggaacaaggg gtacaagcac | 2100 |
| cacgccgagg | acgccctgat | cattgccaac | gccgatttca | tcttcaaaga gtggaagaaa | 2160 |
| ctggacaagg | ccaaaaaagt | gatggaaaac | cagatgttcg | aggaaaagca ggccgagagc | 2220 |
| atgcccgaga | tcgaaaccga | gcaggagtac | aaagagatct | tcatcacccc ccaccagatc | 2280 |
| aagcacatta | aggacttcaa | ggactacaag | tacagccacc | gggtggacaa gaagcctaat | 2340 |
| agagagctga | ttaacgacac | cctgtactcc | acccggaagg | acgacaaggg caacacccutg | 2400 |
| atcgtgaaca | atctgaacgg | cctgtacgac | aaggacaatg | acaagctgaa aaagctgatc | 2460 |
| aacaagagcc | ccgaaaagct | gctgatgtac | caccacgacc | cccagaccta ccagaaactg | 2520 |
| aagctgatta | tggaacagta | cggcgacgag | aagaatcccc | tgtacaagta ctacgaggaa | 2580 |

SEQUENCE LISTING

```
accgggaact  acctgaccaa  gtactccaaa  aaggacaacg  gccccgtgat  caagaagatt     2640
aagtattacg  gcaacaaact  gaacgcccat  ctggacatca  ccgacgacta  ccccaacagc     2700
agaaacaagg  tcgtgaagct  gtccctgaag  ccctacagat  tcgacgtgta  cctggacaat     2760
ggcgtgtaca  agttcgtgac  cgtgaagaat  ctggatgtga  tcaaaaaaga  aaactactac     2820
gaagtgaata  gcaagtgcta  tgaggaagct  aagaagctga  agaagatcag  caaccaggcc     2880
gagtttatcg  cctccttcta  caacaacgat  ctgatcaaga  tcaacggcga  gctgtataga     2940
gtgatcggcg  tgaacaacga  cctgctgaac  cggatcgaag  tgaacatgat  cgacatcacc     3000
taccgcgagt  acctggaaaa  catgaacgac  aagaggcccc  ccaggatcat  taagacaatc     3060
gcctccaaga  cccagagcat  taagaagtac  agcacagaca  ttctgggcaa  cctgtatgaa     3120
gtgaaatcta  agaagcaccc  tcagatcatc  aaaaagggc                             3159
```

An exemplary codon optimized nucleic acid sequences encoding a Cas9 molecule of *S. aureus* (SEQ ID NO: 12).

```
atgaagcgca  actacatcct  cggactggac  atcggcatta  cctccgtggg  atacggcatc       60
atcgattacg  aaactaggga  tgtgatcgac  gctggagtca  ggctgttcaa  agaggcgaac      120
gtggagaaca  acgaggggcg  cgctcaaag   aggggggccc  gccggctgaa  gcgccgccgc      180
agacatagaa  tccagcgcgt  gaagaagctg  ctgttcgact  acaaccttct  gaccgaccac      240
tccgaacttt  ccggcatcaa  cccatatgag  gctagagtga  agggattgtc  ccaaaagctg      300
tccgaggaag  agttctccgc  cgcgttgctc  cacctcgcca  agcgcagggg  agtgcacaat      360
gtgaacgaag  tggaagaaga  taccggaaac  gagctgtcca  ccaaggagca  gatcagccgg      420
aactccaagg  ccctggaaga  gaaatacgtg  gcggaactgc  aactggagcg  gctgaagaaa      480
gacggagaag  tgcgcggctc  gatcaaccgc  ttcaagacct  cggactacgt  gaaggaggcc      540
aagcagctcc  tgaaagtgca  aaaggcctat  caccaacttg  accagtcctt  tatcgatacc      600
tacatcgatc  tgctcgagac  tcggcggact  tactacgagg  gtccagggga  gggctcccca      660
tttggttgga  aggatattaa  ggagtggtac  gaaatgctga  tgggacactg  cacatacttc      720
cctgaggagc  tgcggagcgt  gaaatacgca  tacaacgcag  acctgtacaa  cgcgctgaac      780
gacctgaaca  atctcgtgat  cacccgggac  gagaacgaaa  agctcgagta  ttacgaaaag      840
ttccagatta  ttgagaacgt  gttcaaacag  aagaagaagc  cgacactgaa  gcagattgcc      900
aaggaaatcc  tcgtaacga   agaggacatc  aagggctatc  gagtgaccta  aacgggaaag      960
ccggagttca  ccaatctgaa  ggtctaccac  gacatcaaag  acattaccgc  ccggaaggag     1020
atcattgaga  acgcggagct  gttggaccag  attgcgaaga  ttctgaccat  ctaccaatcc     1080
tccgaggata  ttcaggaaga  actcaccaac  ctcaacagcg  aactgaccca  ggaggagata     1140
gagcaaatct  ccaacctgaa  gggctacacc  ggaactcata  acctgagcct  gaaggccatc     1200
aacttgatcc  tggacgagct  gtggcacacc  aacgataacc  agatcgctat  tttcaatcgg     1260
ctgaagctgg  tccccaagaa  agtggacctc  tcacaacaaa  aggagatccc  tactacccct     1320
gtggacgatt  tcattctgtc  ccccgtggtc  aagagaagct  tcatacagtc  aatcaaagtg     1380
atcaatgcca  ttatcaagaa  atacggtctg  cccaacgaca  ttatcattga  gctcgcccgc     1440
gagaagaact  cgaaggacgc  ccagaagatg  attaacgaaa  tgcagaagag  gaaccgacag     1500
actaacgaac  ggatcgaaga  aatcatccgg  accaccggga  aggaaaacgc  gaagtacctg     1560
atcgaaaaga  tcaagctcca  tgacatgcag  gaaggaaagt  gtctgtactc  gctggaggcc     1620
```

| SEQUENCE LISTING | |
|---|---|
| attccgctgg aggacttgct gaacaaccct tttaactacg aagtggatca tatcattccg | 1680 |
| aggagcgtgt cattcgacaa ttccttcaac aacaaggtcc tcgtgaagca ggaggaaaac | 1740 |
| tcgaagaagg gaaaccgcac gccgttccag tacctgagca gcagcgactc caagatttcc | 1800 |
| tacgaaacct tcaagaagca catcctcaac ctggcaaagg ggaagggtcg catctccaag | 1860 |
| accaagaagg aatatctgct ggaagaaaga gacatcaaca gattctccgt gcaaaaggac | 1920 |
| ttcatcaacc gcaacctcgt ggatactaga tacgctactc ggggtctgat gaacctcctg | 1980 |
| agaagctact ttagagtgaa caatctggac gtgaaggtca agtcgattaa cggaggtttc | 2040 |
| acctccttcc tgcggcgcaa gtggaagttc aagaaggaac ggaacaaggg ctacaagcac | 2100 |
| cacgccgagg acgccctgat cattgccaac gccgacttca tcttcaaaga atggaagaaa | 2160 |
| cttgacaagg ctaagaaggt catggaaaac cagatgttcg aagaaaagca ggccgagtct | 2220 |
| atgcctgaaa tcgagactga acaggagtac aaggaaatct ttattacgcc acaccagatc | 2280 |
| aaacacatca aggatttcaa ggattacaag tactcacatc gcgtggacaa aaagccgaac | 2340 |
| agggaactga tcaacgacac cctctactcc acccggaagg atgacaaagg gaataccctc | 2400 |
| atcgtcaaca accttaacgg cctgtacgac aaggacaacg ataagctgaa gaagctcatt | 2460 |
| aacaagtcgc ccgaaaagtt gctgatgtac caccacgacc ctcagactta ccagaagctc | 2520 |
| aagctgatca tggagcagta tggggacgag aaaaacccgt tgtacaagta ctacgaagaa | 2580 |
| actgggaatt atctgactaa gtactccaag aaagataacg ccccgtgat taagaagatt | 2640 |
| aagtactacg gcaacaagct gaacgcccat ctggacatca ccgatgacta ccctaattcc | 2700 |
| cgcaacaagg tcgtcaagct gagcctcaag ccctaccggt tgatgtgta ccttgacaat | 2760 |
| ggagtgtaca agttcgtgac tgtgaagaac cttgacgtga tcaagaagga gaactactac | 2820 |
| gaagtcaact ccaagtgcta cgaggaagca aagaagttga agaagatctc gaaccaggcc | 2880 |
| gagttcattg cctccttcta taacaacgac ctgattaaga tcaacggcga actgtaccgc | 2940 |
| gtcattggcg tgaacaacga tctcctgaac cgcatcgaag tgaacatgat cgacatcact | 3000 |
| taccgggaat acctggagaa tatgaacgac aagcgcccgc cccggatcat taagactatc | 3060 |
| gcctcaaaga cccagtcgat caagaagtac agcaccgaca tcctgggcaa cctgtacgag | 3120 |
| gtcaaatcga gaagcaccc ccagatcatc aagaaggga | 3159 |

An exemplary *S. pyogenes* Cas9 amino acid sequence (SEQ ID NO: 13).

| | |
|---|---|
| MDKKYSIGLD IGTNSVGWAV ITDEYKVPSK KFKVLGNTDR HSIKKNLIGA | 50 |
| LLFDSGETAE ATRLKRTARR RYTRRKNRIC YLQEIFSNEM AKVDDSFFHR | 100 |
| LEESFLVEED KKHERHPIFG NIVDEVAYHE KYPTIYHLRK KLVDSTDKAD | 150 |
| LRLIYLALAH MIKFRGHFLI EGDLNPDNSD VDKLFIQLVQ TYNQLFEENP | 200 |
| INASGVDAKA ILSARLSKSR RLENLIAQLP GEKKNGLFGN LIALSLGLTP | 250 |
| NFKSNFDLAE DAKLQLSKDT YDDDLDNLLA QIGDQYADLF LAAKNLSDAI | 300 |
| LLSDILRVNT EITKAPLSAS MIKRYDEHHQ DLTLLKALVR QQLPEKYKEI | 350 |
| FFDQSKNGYA GYIDGGASQE EFYKFIKPIL EKMDGTEELL VKLNREDLLR | 400 |
| KQRTFDNGSI PHQIHLGELH AILRRQEDFY PFLKDNREKI EKILTFRIPY | 450 |
| YVGPLARGNS RFAWMTRKSE ETITPWNFEE VVDKGASAQS FIERMTNFDK | 500 |
| NLPNEKVLPK HSLLYEYFTV YNELTKVKYV TEGMRKPAFL SGEQKKAIVD | 550 |
| LLFKTNRKVT VKQLKEDYFK KIECFDSVEI SGVEDRFNAS LGTYHDLLKI | 600 |

SEQUENCE LISTING

```
IKDKDFLDNE ENEDILEDIV LTLTLFEDRE MIEERLKTYA HLFDDKVMKQ      650

LKRRRYTGWG RLSRKLINGI RDKQSGKTIL DFLKSDGFAN RNFMQLIHDD      700

SLTFKEDIQK AQVSGQGDSL HEHIANLAGS PAIKKGILQT VKVVDELVKV      750

MGRHKPENIV IEMARENQTT QKGQKNSRER MKRIEEGIKE LGSQILKEHP      800

VENTQLQNEK LYLYYLQNGR DMYVDQELDI NRLSDYDVDH IVPQSFLKDD      850

SIDNKVLTRS DKNRGKSDNV PSEEVVKKMK NYWRQLLNAK LITQRKFDNL      900

TKAERGGLSE LDKAGFIKRQ LVETRQITKH VAQILDSRMN TKYDENDKLI      950

REVKVITLKS KLVSDFRKDF QFYKVREINN YHHAHDAYLN AVVGTALIKK     1000

YPKLESEFVY GDYKVYDVRK MIAKSEQEIG KATAKYFFYS NIMNFFKTEI     1050

TLANGEIRKR PLIETNGETG EIVWDKGRDF ATVRKVLSMP QVNIVKKTEV     1100

QTGGFSKESI LPKRNSDKLI ARKKDWDPKK YGGFDSPTVA YSVLVVAKVE     1150

KGKSKKLKSV KELLGITIME RSSFEKNPID FLEAKGYKEV KKDLIIKLPK     1200

YSLFELENGR KRMLASAGEL QKGNELALPS KYVNFLYLAS HYEKLKGSPE     1250

DNEQKQLFVE QHKHYLDEII EQISEFSKRV ILADANLDKV LSAYNKHRDK     1300

PIREQAENII HLFTLTNLGA PAAFKYFDTT IDRKRYTSTK EVLDATLIHQ     1350

SITGLYETRI DLSQLGGD                                         1368
```

An exemplary *Neisseria meningitidis* Cas9 amino acid sequence (SEQ ID NO: 14).

```
AAFKPNSINYILGLDIGIASVGWAMVEIDEEENPIRLIDLGVRVFERAEVPKTGDSLAMARRLA
RSVRRLTRRRAHRLLRTRRLLKREGVLQAANFDENGLIKSLPNTPWQLRAAALDRKLTPLEWSA
VLLHLIKHRGYLSQRKNEGETADKELGALLKGVAGNAHALQTGDFRTPAELALNKFEKESGHIR
NQRSDYSHTFSRKDLQAELILLFEKQKEFGNPHVSGGLKEGIETLLMTQRPALSGDAVQKMLGH
CTFEPAEPKAAKNTYTAERFIWLTKLNNLRILEQGSERPLTDTERATLMDEPYRKSKLTYAQAR
KLLGLEDTAFFKGLRYGKDNAEASTLMEMKAYHAISRALEKEGLKDKKSPLNLSPELQDEIGTA
FSLFKIDEDITGRLKDRIQPEILEALLKHISFDKFVQISLKALRRIVPLMEQGKRYDEACAEIY
GDHYGKKNTEEKIYLPPIPADEIRNPVVLRALSQARKVINGVVRRYGSPARIHIETAREVGKSF
KDRKEIEKRQEENRKDREKAAAKFREYFPNFVGEPKSKDILKLRLYEQQHGKCLYSGKEINLGR
LNEKGYVEIDHALPFSRTWDDSFNNKVLVLGSENQNKGNQTPYEYFNGKDNSREWQEFKARVET
SRFPRSKKQRILLQKFDEDGFKERNLNDTRYVNRFLCQFVADRMRLTGKGKKRVFASNGQITNL
LRGFWGLRKVRAENDRHHALDAVVVACSTVAMQQKITRFVRYKEMNAFDGKTIDKETGEVLHQK
THFPQPWEFFAQEVMIRVFGKPDGKPEFEEADTLEKLRILLAEKLSSRPEAVHEYVTPLFVSRA
PNRKMSGQGHMETVKSAKRLDEGVSVLRVPLTQLKLKDLEKMVNREREPKLYEALKARLEAHKD
DPAKAFAEPFYKYDKAGNRTQQVKAVRVEQVQKTGVWVRNHNGIADNATMVRVDVFEKGDKYYL
VPIYSWQVAKGILPDRAVVQGKDEEDWQLIDDSFNFKFSLHPNDLVEVITKKARMFGYFASCHR
GTGNINIRIHDLDHKIGKNGILEGIGVKTALSFQKYQIDELGKEIRPCRLKKRPPVR
```

The invention claimed is:

1. A method of editing a population of double stranded DNA (dsDNA) molecules, the method comprising contacting the dsDNA molecules with:
   (i) a polypeptide comprising an amino acid sequence having at least 90% identity to SEQ ID NO: 13, wherein the SPCas9-polypeptide comprises an amino acid substitution at two or more of the following positions of SEQ ID NO:13: D23, T67, Y128, and D1251, and
   (ii) a guide nucleic acid having a region complementary to a target sequence of the dsDNA molecules,
   whereby a plurality of the dsDNA molecules are edited.

2. The method of claim 1, wherein a rate of off-target editing by the polypeptide of an off-target sequence is less than the observed rate of off-target editing of the off-target sequence by a polypeptide comprising the amino acid sequence of SEQ ID NO:13.

3. The method of claim 2, wherein the rate of off-target editing by the polypeptide is about 5%, 10%, 15%, 20%, 25%, 30%, 40%, 50%, 60%, 70%, or 80% less than that of the polypeptide comprising the amino acid sequence of SEQ ID NO:13.

4. The method of claim 2, wherein the rate of off-target editing is measured by assessing a level of indels at the off-target sequence.

5. The method of claim 1, comprising contacting the dsDNA molecules with an RNP complex comprising the polypeptide and guide nucleic acid.

6. The method of claim 5, comprising contacting the dsDNA molecules with the RNP complex, wherein the RNP complex is at a dose of $1 \times 10^{-4}$ μM to 1 μM RNP.

* * * * *

SEQUENCE LISTING

<160> NUMBER OF SEQ IDS: 14

<210> SEQ ID NO 1
<211> LENGTH: 20
<212> TYPE: DNA

```
<213> ORGANISM: Artificial Sequence
<220> FEATURE:
<223> OTHER INFORMATION: chemically synthesized oligonucleotide

<400> SEQUENCE: 1
taacctggag gatctgatcc                                            20

<210> SEQ ID NO 2
<211> LENGTH: 26
<212> TYPE: DNA
<213> ORGANISM: Artificial Sequence
<220> FEATURE:
<223> OTHER INFORMATION: chemically synthesized oligonucleotide

<400> SEQUENCE: 2
taacctggag gatctgatcc gggaga                                     26

<210> SEQ ID NO 3
<211> LENGTH: 26
<212> TYPE: DNA
<213> ORGANISM: Artificial Sequence
<220> FEATURE:
<223> OTHER INFORMATION: chemically synthesized oligonucleotide

<400> SEQUENCE: 3
taacctggag gatctgatcc gggagc                                     26

<210> SEQ ID NO 4
<211> LENGTH: 23
<212> TYPE: DNA
<213> ORGANISM: Artificial Sequence
<220> FEATURE:
<223> OTHER INFORMATION: chemically synthesized oligonucleotide
<220> FEATURE:
<221> NAME/KEY: misc_feature
<222> LOCATION: (21)..(21)
<223> OTHER INFORMATION: n is a, c, g, or t

<400> SEQUENCE: 4
gtctgggcgg tgctacaact ngg                                        23

<210> SEQ ID NO 5
<211> LENGTH: 23
<212> TYPE: DNA
<213> ORGANISM: Artificial Sequence
<220> FEATURE:
<223> OTHER INFORMATION: chemically synthesized oligonucleotide

<400> SEQUENCE: 5
aactgggtgg tgctccaact cgg                                        23

<210> SEQ ID NO 6
<211> LENGTH: 23
<212> TYPE: DNA
<213> ORGANISM: Artificial Sequence
<220> FEATURE:
<223> OTHER INFORMATION: chemically synthesized oligonucleotide

<400> SEQUENCE: 6
aacggggcgg tactacaact tgg                                        23

<210> SEQ ID NO 7
<211> LENGTH: 22
<212> TYPE: DNA
<213> ORGANISM: Artificial Sequence
<220> FEATURE:
<223> OTHER INFORMATION: chemically synthesized oligonucleotide
```

<400> SEQUENCE: 7
gtctggtggt gctacaactt gg                                     22

<210> SEQ ID NO 8
<211> LENGTH: 23
<212> TYPE: DNA
<213> ORGANISM: Artificial Sequence
<220> FEATURE:
<223> OTHER INFORMATION: chemically synthesized oligonucleotide

<400> SEQUENCE: 8
acctggacgg tgatacaacc cgg                                    23

<210> SEQ ID NO 9
<211> LENGTH: 4107
<212> TYPE: DNA
<213> ORGANISM: Artificial Sequence
<220> FEATURE:
<223> OTHER INFORMATION: chemically synthesized oligonucleotide

<400> SEQUENCE: 9

```
atggataaaa agtacagcat cgggctggac atcggtacaa actcagtggg gtgggccgtg      60
attacggacg agtacaaggt accctccaaa aatttaaag tgctgggtaa cacggacaga      120
cactctataa agaaaatct tattggagcc ttgctgttcg actcaggcga gacagccgaa      180
gccacaaggt tgaagcggac cgccaggagg cggtatacca ggagaaagaa ccgcatatgc      240
tacctgcaag aaatcttcag taacgagatg gcaaaggttg acgatagctt tttccatcgc      300
ctggaagaat cctttcttgt tgaggaagac aagaagcacg aacggcaccc catctttggc      360
aatattgtcg acgaagtggc atatcacgaa agtacccga ctatctacca cctcaggaag      420
aagctggtgg actctaccga taaggcggac ctcagactta tttatttggc actcgcccac      480
atgattaaat ttagaggaca tttcttgatc gagggcgacc tgaacccgga caacagtgac      540
gtcgataagc tgttcatcca acttgtgcag acctacaatc aactgttcga agaaaaccct      600
ataaatgctt caggagtcga cgctaaagca atcctgtccg cgcgcctctc aaaatctaga      660
agacttgaga atctgattgc tcagttgccc ggggaaaaga aaaatggatt gtttggcaac      720
ctgatcgccc tcagtctcgg actgacccca aatttcaaaa gtaacttcga cctggccgaa      780
gacgctaagc tccagctgtc caaggacaca tacgatgacg acctcgacaa tctgctggcc      840
cagattgggg atcagtacgc cgatctcttt ttggcagcaa gaacctgtc cgacgccatc      900
ctgttgagcg atatccttga agtgaacacc gaaattacta agcacccct tagcgcatct      960
atgatcaagc ggtacgacga gcatcatcag gatctgaccc tgctgaaggc tcttgtgagg     1020
caacagctcc ccgaaaaata caaggaaatc ttctttgacc agagcaaaaa cggctacgct     1080
ggctatatag atggtggggc cagtcaggag gaattctata aattcatcaa gcccattctc     1140
gagaaaatgg acggcacaga ggagttgctg gtcaaactta acagggagga cctgctgcgg     1200
aagcagcgga cctttgacaa cgggtctatc ccccaccaga ttcatctggg cgaactgcac     1260
gcaatcctga ggaggcagga ggatttttat ccttttctta agataaccg cgagaaaata     1320
gaaaagattc ttacattcag gatcccgtac tacgtggac ctctcgcccg ggcaattca      1380
cggtttgcct ggatgacaag gaagtcagag gagactatta caccttggaa cttcgaagaa     1440
gtggtggaca gggtgcatc tgcccagtct ttcatcgagc ggatgacaaa ttttgacaag     1500
aacctcccta tgagaaggt gctgcccaaa cattctctgc tctacgagta ctttaccgtc     1560
```

```
tacaatgaac tgactaaagt caagtacgtc accgagggaa tgaggaagcc ggcattcctt    1620
agtggagaac agaagaaggc gattgtagac ctgttgttca agaccaacag gaaggtgact    1680
gtgaagcaac ttaaagaaga ctactttaag aagatcgaat gttttgacag tgtggaaatt    1740
tcaggggttg aagaccgctt caatgcgtca ttggggactt accatgatct tctcaagatc    1800
ataaaggaca aagacttcct ggacaacgaa gaaaatgagg atattctcga agacatcgtc    1860
ctcaccctga ccctgttcga agacaggaa atgatagaag agcgcttgaa aacctatgcc    1920
cacctcttcg acgataaagt tatgaagcag ctgaagcgca ggagatacac aggatgggga    1980
agattgtcaa ggaagctgat caatggaatt agggataaac agagtggcaa gaccatactg    2040
gatttcctca aatctgatgg cttcgccaat aggaacttca tgcaactgat tcacgatgac    2100
tctcttacct tcaaggagga cattcaaaag gctcaggtga gcgggcaggg agactccctt    2160
catgaacaca tcgcgaattt ggcaggttcc cccgctatta aaagggcat ccttcaaact    2220 gtcaaggtgg tggatgaatt ggtcaaggta atgggcagac ataagccaga aaatattgtg    2280
atcgagatgg cccgcgaaaa ccagaccaca cagaaggggcc agaaaaatag tagagagcgg    2340
atgaagagga tcgaggaggg catcaaagag ctgggatctc agattctcaa agaacacccc    2400
gtagaaaaca cacagctgca gaacgaaaaa ttgtacttgt actatctgca gaacggcaga    2460
gacatgtacg tcgaccaaga acttgatatt aatagactgt ccgactatga cgtagaccat    2520
atcgtgcccc agtccttcct gaaggacgac tccattgata caaagtctt gacaagaagc    2580 gacaagaaca ggggtaaaag tgataatgtg cctagcgagg aggtggtgaa aaaaatgaag    2640
aactactggc gacagctgct taatgcaaag ctcattacac aacggaagtt cgataatctg    2700
acgaaagcag agagaggtgg cttgtctgag ttggacaagg cagggtttat taagcggcag    2760
ctggtggaaa ctaggcagat cacaaagcac gtggcgcaga ttttggacag ccggatgaac    2820
acaaaatacg acgaaaatga taaactgata cgagaggtca agttatcac gctgaaaagc    2880 aagctggtgt ccgattttcg gaaagacttc cagttctaca agttcgcga gattaataac    2940 taccatcatg ctcacgatgc gtacctgaac gctgttgtcg ggaccgcctt gataaagaag    3000
tacccaaagc tggaatccga gttcgtatac ggggattaca agtgtacga tgtgaggaaa    3060 atgatagcca agtccgagca ggagattgga aaggccacag ctaagtactt cttttatcct    3120
aacatcatga ttttttttaa gacgaaaatt accctggcca acggagagat cagaaagcgg    3180
ccccttatag agacaaatgg tgaaacaggt gaaatcgtct gggataaggg cagggatttc    3240
gctactgtga ggaaggtgct gagtatgcca caggtaaata tcgtgaaaaa accgaagta    3300 cagaccggag gattttccaa ggaaagcatt ttgcctaaaa gaaactcaga caagctcatc    3360
gcccgcaaga aagattggga ccctaagaaa tacgggggat ttgactcacc caccgtagcc    3420
tattctgtgc tggtggtagc taaggtggaa aaaggaaagt ctaagaagct gaagtccgtg    3480
aaggaactct tgggaatcac tatcatggaa agatcatcct tgaaaagaa ccctatcgat    3540 ttcctggagg ctaagggtta caaggaggtc aagaaagacc tcatcattaa actgccaaaa    3600
tactctctct tcgagctgga aaatggcagg aagagaatgt tggccagcgc cggagagctg    3660
caaaagggaa acgagcttgc tctgccctcc aaatatgtta atttttctcta tctcgcttcc    3720 cactatgaaa agctgaaagg gtctcccgaa gataacgagc agaagcagct gttcgtcgaa    3780
cagcacaagc actatctgga tgaaataatc gaacaaataa gcgagttcag caaaagggtt    3840
atcctggcgg atgctaattt ggacaaagta ctgtctgctt ataacaagca ccgggataag    3900
cctattaggg aacaagccga gaatataatt cacctcttta cactcacgaa tctcggagcc    3960
```

| | |
|---|---|
| cccgccgcct tcaaatactt tgatacgact atcgaccgga aacggtatac cagtaccaaa | 4020 |
| gaggtcctcg atgccaccct catccaccag tcaattactg gcctgtacga aacacggatc | 4080 |
| gacctctctc aactgggcgg cgactag | 4107 |

<210> SEQ ID NO 10
<211> LENGTH: 3159
<212> TYPE: DNA
<213> ORGANISM: Artificial Sequence
<220> FEATURE:
<223> OTHER INFORMATION: chemically synthesized oligonucleotide

<400> SEQUENCE: 10

| | |
|---|---|
| atgaaaagga actacattct ggggctggac atcgggatta caagcgtggg gtatgggatt | 60 |
| attgactatg aaacaaggga cgtgatcgac gcaggcgtca gactgttcaa ggaggccaac | 120 |
| gtggaaaaca atgagggacg gagaagcaag aggggagcca ggcgcctgaa acgacggaga | 180 |
| aggcacagaa tccagagggt gaagaaactg ctgttcgatt acaacctgct gaccgaccat | 240 |
| tctgagctga gtggaattaa tccttatgaa gccagggtga aaggcctgag tcagaagctg | 300 |
| tcagaggaag agttttccgc agctctgctg caccggcta gcgccgagg agtgcataac | 360 |
| gtcaatgagg tggaagagga caccggcaac gagctgtcta caaaggaaca gatctcacgc | 420 |
| aatagcaaag ctctggaaga gaagtatgtc gcagagctgc agctggaacg gctgaagaaa | 480 |
| gatggcgagg tgagagggtc aattaatagg ttcaagacaa gcgactacgt caaagaagcc | 540 |
| aagcagctgc tgaaagtgca gaaggcttac caccagctgg atcagagctt catcgatact | 600 |
| tatatcgacc tgctggagac tcggagaacc tactatgagg accaggaga agggagcccc | 660 |
| ttcggatgga agacatcaa ggaatggtac gagatgctga tgggacattg cacctatttt | 720 |
| ccagaagagc tgagaagcgt caagtacgct tataacgcag atctgtacaa cgccctgaat | 780 |
| gacctgaaca acctggtcat caccagggat gaaaacgaga actggaata ctatgagaag | 840 |
| ttccagatca tcgaaaacgt gtttaagcag aagaaaagc ctacactgaa acagattgct | 900 |
| aaggagatcc tggtcaacga agaggacatc aagggctacc gggtgacaag cactggaaaa | 960 |
| ccagagttca ccaatctgaa agtgtatcac gatattaagg acatcacagc acggaaagaa | 1020 |
| atcattgaga cgccgaact gctggatcag attgctaaga tcctgactat ctaccagagc | 1080 |
| tccgaggaca tccaggaaga gctgactaac ctgaacagcg agctgaccca ggaagagatc | 1140 |
| gaacagatta gtaatctgaa ggggtacacc ggaacacaca acctgtccct gaaagctatc | 1200 |
| aatctgattc tggatgagct gtggcataca acgacaatc agattgcaat ctttaaccgg | 1260 |
| ctgaagctgg tcccaaaaaa ggtggacctg agtcagcaga agagatccc aaccacactg | 1320 |
| gtggacgatt tcattctgtc acccgtggtc aagcggagct tcatccagag catcaaagtg | 1380 |
| atcaacgcca tcatcaagaa gtacggcctg cccaatgata tcattatcga gctggctagg | 1440 |
| gagaagaaca gcaaggacgc acagaagatg atcaatgaga tgcagaaacg aaaccggcag | 1500 |
| accaatgaac gcattgaaga gattatccga actaccggga agagaacgc aaagtacctg | 1560 |
| attgaaaaaa tcaagctgca cgatatgcag gagggaaagt gtctgtattc tctggaggcc | 1620 |
| atcccctgg aggacctgct gaacaatcca ttcaactacg aggtcgatca tattatcccc | 1680 |
| agaagcgtgt ccttcgacaa ttcctttaac aacaaggtgc tggtcaagca ggaagagaac | 1740 |
| tctaaaaagg gcaataggac tccttttccag tacctgtcta gttcagattc caagatctct | 1800 |
| tacgaaacct ttaaaaagca cattctgaat ctggccaaag gaaagggccg catcagcaag | 1860 |

| | |
|---|---|
| accaaaaagg agtacctgct ggaagagcgg gacatcaaca gattctccgt ccagaaggat | 1920 |
| tttattaacc ggaatctggt ggacacaaga tacgctactc gcggcctgat gaatctgctg | 1980 |
| cgatcctatt tccgggtgaa caatctggat gtgaaagtca agtccatcaa cggcgggttc | 2040 |
| acatcttttc tgaggcgcaa atggaagttt aaaaaggagc gcaacaaagg gtacaagcac | 2100 |
| catgccgaag atgctctgat tatcgcaaat gccgacttca tctttaagga gtggaaaaag | 2160 |
| ctggacaaag ccaagaaagt gatggagaac cagatgttcg aagagaagca ggccgaatct | 2220 |
| atgcccgaaa tcgagacaga acaggagtac aaggagattt tcatcactcc tcaccagatc | 2280 |
| aagcatatca aggatttcaa ggactacaag tactctcacc gggtggataa aaagcccaac | 2340 |
| agagagctga tcaatgacac cctgtatagt acaagaaaag acgataaggg gaataccctg | 2400 |
| attgtgaaca atctgaacgg actgtacgac aaagataatg acaagctgaa aaagctgatc | 2460 |
| aacaaaagtc ccgagaagct gctgatgtac caccatgatc ctcagacata tcagaaactg | 2520 |
| aagctgatta tggagcagta cggcgacgag aagaacccac tgtataagta ctatgaagag | 2580 |
| actgggaact acctgaccaa gtatagcaaa aaggataatg gccccgtgat caagaagatc | 2640 |
| aagtactatg gaacaagct gaatgcccat ctggacatca cagacgatta ccctaacagt | 2700 |
| cgcaacaagg tggtcaagct gtcactgaag ccatacagat cgatgtcta tctggacaac | 2760 |
| ggcgtgtata aatttgtgac tgtcaagaat ctggatgtca tcaaaaagga gaactactat | 2820 |
| gaagtgaata gcaagtgcta cgaagaggct aaaaagctga aaagattag caaccaggca | 2880 |
| gagttcatcg cctccttta caacaacgac ctgattaaga tcaatggcga actgtatagg | 2940 |
| gtcatcgggg tgaacaatga tctgctgaac cgcattgaag tgaatatgat tgacatcact | 3000 |
| taccgagagt atctggaaaa catgaatgat aagcgcccc ctcgaattat caaaacaatt | 3060 |
| gcctctaaga ctcagagtat caaaaagtac tcaaccgaca ttctgggaaa cctgtatgag | 3120 |
| gtgaagagca aaaagcaccc tcagattatc aaaaagggc | 3159 |

<210> SEQ ID NO 11
<211> LENGTH: 3159
<212> TYPE: DNA
<213> ORGANISM: Artificial Sequence
<220> FEATURE:
<223> OTHER INFORMATION: chemically synthesized oligonucleotide

<400> SEQUENCE: 11

| | |
|---|---|
| atgaagcgga actacatcct gggcctggac atcggcatca ccagcgtggg ctacggcatc | 60 |
| atcgactacg agacacggga cgtgatcgat gccggcgtgc ggctgttcaa agaggccaac | 120 |
| gtggaaaaca cgagggcag gcggagcaag agaggcgcca aaggctgaa gcggcggagg | 180 |
| cggcatagaa tccagagagt gaagaagctg ctgttcgact acaacctgct gaccgaccac | 240 |
| agcgagctga gcggcatcaa ccctacgag gccgagtga agggcctgag ccagaagctg | 300 |
| agcgaggaag agttctctgc cgccctgctg cacctggcca agagaagagg cgtgcacaac | 360 |
| gtgaacgagt ggaagagga caccggcaac gagctgtcca ccaaagagca gatcagccgg | 420 |
| aacagcaagg ccctggaaga gaaatacgtg gccgaactgc agctggaacg gctgaagaaa | 480 |
| gacggcgaag tgcggggcag catcaacaga ttcaagacca cgactacgt gaagaagcc | 540 |
| aaacagctgc tgaaggtgca aaggcctac accagctgg accagagctt catcgacacc | 600 |
| tacatcgacc tgctggaaac ccggcggacc tactatgagg gacctggcga gggcagcccc | 660 |
| ttcggctgga ggacatcaa agaatggtac gagatgctga tgggccactg cacctacttc | 720 |
| cccgaggaac tgcggagcgt gaagtacgcc tacaacgccg acctgtacaa cgccctgaac | 780 |

```
gacctgaaca atctcgtgat caccagggac gagaacgaga agctggaata ttacgagaag     840
ttccagatca tcgagaacgt gttcaagcag aagaagaagc ccacccctgaa gcagatcgcc    900 aaagaaatcc tcgtgaacga agaggatatt aagggctaca gagtgaccag caccggcaag     960
cccgagttca ccaacctgaa ggtgtaccac gacatcaagg acattaccgc ccggaaagag    1020
attattgaga cgccgagct gctggatcag attgccaaga tcctgaccat ctaccagagc     1080
agcgaggaca tccaggaaga actgaccaat ctgaactccg agctgaccca ggaagagatc    1140
gagcagatct ctaatctgaa gggctatacc ggcacccaca acctgagcct gaaggccatc    1200
aacctgatcc tggacgagct gtggcacacc aacgacaacc agatcgctat cttcaaccgg    1260
ctgaagctgg tgcccaagaa ggtggacctg tcccagcaga aagagatccc caccaccctg    1320
gtggacgact tcatcctgag ccccgtcgtg aagagaagct tcatccagag catcaaagtg    1380
atcaacgcca tcatcaagaa gtacggcctg cccaacgaca tcattatcga gctggcccgc    1440
gagaagaact ccaaggacgc ccagaaaatg atcaacgaga tgcagaagcg gaaccggcag    1500
accaacgagc ggatcgagga aatcatccgg accaccggca agagaacgc caagtacctg    1560 atcgagaaga tcaagctgca cgacatgcag gaaggcaagt gcctgtacag cctggaagcc    1620
atccctctgg aagatctgct gaacaacccc ttcaactatg aggtggacca catcatcccc    1680
agaagcgtgt ccttcgacaa cagcttcaac aacaaggtgc tcgtgaagca ggaagaaaac    1740
agcaagaagg gcaaccggac cccattccag tacctgagca gcagcgacag caagatcagc    1800
tacgaaacct tcaagaagca catcctgaat ctggccaagg gcaagggcag aatcagcaag    1860
accaagaaag agtatctgct ggaagaacgg gacatcaaca ggttctccgt gcagaaagac    1920
ttcatcaacc ggaacctggt ggataccaga tacgccacca gaggcctgat gaacctgctg    1980
cggagctact tcagagtgaa caacctggac gtgaaagtga agtccatcaa tggcggcttc    2040
accagctttc tgcggcggaa gtggaagttt aagaaagagc ggaacaaggg gtacaagcac    2100
cacgccgagg acgccctgat cattgccaac gccgatttca tcttcaaaga gtggaagaaa    2160
ctggacaagg ccaaaaaagt gatggaaaac cagatgttcg aggaaaagca ggccgagagc    2220
atgcccgaga tcgaaaccga gcaggagtac aaagagatct tcatcacccc ccaccagatc    2280
aagcacatta aggacttcaa ggactacaag tacagccacc gggtggacaa gaagcctaat    2340
agagagctga ttaacgacac cctgtactcc acccggaagg acgacaaggg caacaccctg    2400
atcgtgaaca atctgaacgg cctgtacgac aaggacaatg acaagctgaa aaagctgatc    2460
aacaagagcc ccgaaaagct gctgatgtac caccacgacc cccagaccta ccagaaactg    2520
aagctgatta tggaacagta cggcgacgag aagaatcccc tgtacaagta ctacgaggaa    2580
accgggaact acctgaccaa gtactccaaa aaggacaacg gccccgtgat caagaagatt    2640
aagtattacg gcaacaaact gaacgcccat ctggacatca ccgacgacta ccccaacagc    2700
agaaacaagg tcgtgaagct gtccctgaag ccctacagat cgacgtgta cctggacaat    2760 ggcgtgtaca agttcgtgac cgtgaagaat ctggatgtga tcaaaaaaga aaactactac    2820
gaagtgaata gcaagtgcta tgaggaagct aagaagctga aagatcag caaccaggcc     2880 gagtttatcg cctccttcta caacaacgat ctgatcaaga tcaacggcga gctgtataga    2940
gtgatcggcg tgaacaacga cctgctgaac cggatcgaag tgaacatgat cgacatcacc    3000
taccgcgagt acctggaaaa catgaacgac aagaggcccc ccaggatcat aagacaatc    3060 gcctccaaga cccagagcat aagaagtac agcacagaca ttctgggcaa cctgtatgaa    3120
```

```
gtgaaatcta agaagcaccc tcagatcatc aaaaagggc                          3159
```

<210> SEQ ID NO 12
<211> LENGTH: 3159
<212> TYPE: DNA
<213> ORGANISM: Artificial Sequence
<220> FEATURE:
<223> OTHER INFORMATION: chemically synthesized oligonucleotide

<400> SEQUENCE: 12

```
atgaagcgca actacatcct cggactggac atcggcatta cctccgtggg atacggcatc      60
atcgattacg aaactaggga tgtgatcgac gctggagtca ggctgttcaa agaggcgaac     120
gtggagaaca acgaggggcg gcgctcaaag aggggggccc gccggctgaa gcgccgccgc     180
agacatagaa tccagcgcgt gaagaagctg ctgttcgact acaaccttct gaccgaccac     240
tccgaacttt ccggcatcaa cccatatgag gctagagtga agggattgtc ccaaaagctg     300
tccgaggaag agttctccgc cgcgttgctc cacctcgcca agcgcagggg agtgcacaat     360
gtgaacgaag tggaagaaga taccggaaac gagctgtcca ccaaggagca gatcagccgg     420
aactccaagg ccctggaaga gaaatacgtg gcggaactgc aactggagcg gctgaagaaa     480
gacgagaagt gcgcggctc gatcaaccgc ttcaagacct cggactacgt gaaggaggcc     540
aagcagctcc tgaaagtgca aaaggcctat caccaacttg accagtcctt tatcgatacc     600
tacatcgatc tgctcgagac tcggcggact actacgaggg tccaggggga gggctcccca     660
tttggttgga aggatattaa ggagtggtac gaaatgctga tgggacactg cacatacttc     720
cctgaggagc tgcggagcgt gaaatacgca taacgcag acctgtacaa cgcgctgaac     780
gacctgaaca atctcgtgat cacccgggac gagaacgaaa agctcgagta ttacgaaaag     840
ttccagatta ttgagaacgt gttcaaacag aagaagaagc cgacactgaa gcagattgcc     900
aaggaaatcc tcgtgaacga gaggacatc aagggctatc gagtgaccte aacgggaaag     960
ccggagttca ccaatctgaa ggtctaccac gacatcaaag acattaccgc ccggaaggag    1020
atcattgaga acgcggagct gttggaccag attgcgaaga ttctgaccat ctaccaatcc    1080
tccgaggata ttcaggaaga actccaccaac ctcaacagcg aactgaccca ggaggagata    1140
gagcaaatct ccaacctgaa gggctacacc ggaactcata acctgagcct gaaggccatc    1200
aacttgatcc tggacgagct gtggcacacc aacgataacc agatcgctat tttcaatcgg    1260
ctgaagctgg tccccaagaa agtggacctc tcacaacaaa aggagatccc tactaccctt    1320
gtggacgatt tcattctgtc ccccgtggtc aagagaagct tcatacagtc aatcaaagtg    1380
atcaatgcca ttatcaagaa atacggtctg cccaacgaca ttatcattga gctcgcccgc    1440
gagaagaact cgaaggacgc ccagaagatg attaacgaaa tgcagaagag gaaccgacag    1500
actaacgaac ggatcgaaga atcatccgg accaccggga aggaaaacgc gaagtacctg    1560
atcgaaaaga tcaagctcca tgacatgcag gaaggaaagt gtctgtactc gctggaggcc    1620
attccgctgg aggacttgct gaacaaccct tttaactacg aagtggatca tatcattccg    1680
aggagcgtgt cattcgacaa ttccttcaac aacaaggtcc tcgtgaagca ggaggaaaac    1740
tcgaagaagg aaaccgcac gccgttccag tacctgagca gcagcgactc caagatttcc    1800
tacgaaacct tcaagaagca catcctcaac ctggcaaagg ggaagggtcg catctccaag    1860
accaagaagg aatatctgct ggaagaaaga gacatcaaca gattctccgt gcaaaaggac    1920
ttcatcaacc gcaacctcgt ggatactaga tacgctactc ggggtctgat gaacctcctg    1980
agaagctact ttagagtgaa caatctggac gtgaaggtca agtcgattaa cggaggtttc    2040
```

```
acctccttcc tgcggcgcaa gtggaagttc aagaaggaac ggaacaaggg ctacaagcac    2100
cacgccgagg acgccctgat cattgccaac gccgacttca tcttcaaaga atggaagaaa    2160
cttgacaagg ctaagaaggt catggaaaac cagatgttcg aagaaaagca ggccgagtct    2220
atgcctgaaa tcgagactga acaggagtac aaggaaatct ttattacgcc acaccagatc    2280
aaacacatca aggatttcaa ggattacaag tactcacatc gcgtggacaa aaagccgaac    2340
agggaactga tcaacgacac cctctactcc acccggaagg atgacaaagg gaataccctc    2400
atcgtcaaca accttaacgg cctgtacgac aaggacaacg ataagctgaa gaagctcatt    2460
aacaagtcgc ccgaaaagtt gctgatgtac caccacgacc ctcagactta ccagaagctc    2520
aagctgatca tggagcagta tggggacgag aaaaacccgt tgtacaagta ctacgaagaa    2580
actgggaatt atctgactaa gtactccaag aaagataacg gccccgtgat taagaagatt    2640
aagtactacg gcaacaagct gaacgcccat ctggacatca ccgatgacta ccctaattcc    2700
cgcaacaagg tcgtcaagct gagcctcaag ccctaccggt tgatgtgta ccttgacaat    2760 ggagtgtaca agttcgtgac tgtgaagaac cttgacgtga tcaagaagga gaactactac    2820
gaagtcaact ccaagtgcta cgaggaagca aagaagttga agaagatctc gaaccaggcc    2880
gagttcattg cctccttcta taacaacgac ctgattaaga tcaacggcga actgtaccgc    2940
gtcattggcg tgaacaacga tctcctgaac cgcatcgaag tgaacatgat cgacatcact    3000
taccgggaat acctggagaa tatgaacgac aagcgcccgc cccggatcat taagactatc    3060
gcctcaaaga cccagtcgat caagaagtac agcaccgaca tcctgggcaa cctgtacgag    3120
gtcaaatcga agaagcaccc ccagatcatc aagaaggga                           3159
```

<210> SEQ ID NO 13
<211> LENGTH: 1368
<212> TYPE: PRT
<213> ORGANISM: Streptococcus pyogenes

<400> SEQUENCE: 13

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175
```

-continued

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

-continued

```
Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
```

```
                  1010                1015                1020
Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 14
<211> LENGTH: 1081
<212> TYPE: PRT
<213> ORGANISM: Neisseria meningitidis

<400> SEQUENCE: 14
```

```
Ala Ala Phe Lys Pro Asn Ser Ile Asn Tyr Ile Leu Gly Leu Asp Ile
 1               5                  10                  15

Gly Ile Ala Ser Val Gly Trp Ala Met Val Glu Ile Asp Glu Glu
            20                  25                  30

Asn Pro Ile Arg Leu Ile Asp Leu Gly Val Arg Val Phe Glu Arg Ala
                35                  40                  45

Glu Val Pro Lys Thr Gly Asp Ser Leu Ala Met Ala Arg Arg Leu Ala
 50                  55                  60

Arg Ser Val Arg Arg Leu Thr Arg Arg Ala His Arg Leu Leu Arg
 65                  70                  75                  80

Thr Arg Arg Leu Leu Lys Arg Glu Gly Val Leu Gln Ala Ala Asn Phe
                85                  90                  95

Asp Glu Asn Gly Leu Ile Lys Ser Leu Pro Asn Thr Pro Trp Gln Leu
                100                 105                 110

Arg Ala Ala Ala Leu Asp Arg Lys Leu Thr Pro Leu Glu Trp Ser Ala
                115                 120                 125

Val Leu Leu His Leu Ile Lys His Arg Gly Tyr Leu Ser Gln Arg Lys
 130                 135                 140

Asn Glu Gly Glu Thr Ala Asp Lys Glu Leu Gly Ala Leu Leu Lys Gly
145                 150                 155                 160

Val Ala Gly Asn Ala His Ala Leu Gln Thr Gly Asp Phe Arg Thr Pro
                165                 170                 175

Ala Glu Leu Ala Leu Asn Lys Phe Glu Lys Glu Ser Gly His Ile Arg
                180                 185                 190

Asn Gln Arg Ser Asp Tyr Ser His Thr Phe Ser Arg Lys Asp Leu Gln
                195                 200                 205

Ala Glu Leu Ile Leu Leu Phe Glu Lys Gln Lys Glu Phe Gly Asn Pro
 210                 215                 220

His Val Ser Gly Gly Leu Lys Glu Gly Ile Glu Thr Leu Leu Met Thr
225                 230                 235                 240

Gln Arg Pro Ala Leu Ser Gly Asp Ala Val Gln Lys Met Leu Gly His
                245                 250                 255

Cys Thr Phe Glu Pro Ala Glu Pro Lys Ala Ala Lys Asn Thr Tyr Thr
                260                 265                 270

Ala Glu Arg Phe Ile Trp Leu Thr Lys Leu Asn Asn Leu Arg Ile Leu
                275                 280                 285

Glu Gln Gly Ser Glu Arg Pro Leu Thr Asp Thr Glu Arg Ala Thr Leu
 290                 295                 300

Met Asp Glu Pro Tyr Arg Lys Ser Lys Leu Thr Tyr Ala Gln Ala Arg
305                 310                 315                 320

Lys Leu Leu Gly Leu Glu Asp Thr Ala Phe Phe Lys Gly Leu Arg Tyr
                325                 330                 335

Gly Lys Asp Asn Ala Glu Ala Ser Thr Leu Met Glu Met Lys Ala Tyr
                340                 345                 350

His Ala Ile Ser Arg Ala Leu Glu Lys Glu Gly Leu Lys Asp Lys
                355                 360                 365

Ser Pro Leu Asn Leu Ser Pro Glu Leu Gln Asp Glu Ile Gly Thr Ala
 370                 375                 380

Phe Ser Leu Phe Lys Thr Asp Glu Asp Ile Thr Gly Arg Leu Lys Asp
385                 390                 395                 400

Arg Ile Gln Pro Glu Ile Leu Glu Ala Leu Leu Lys His Ile Ser Phe
                405                 410                 415

Asp Lys Phe Val Gln Ile Ser Leu Lys Ala Leu Arg Arg Ile Val Pro
```

```
            420             425             430
Leu Met Glu Gln Gly Lys Arg Tyr Asp Glu Ala Cys Ala Glu Ile Tyr
            435             440             445

Gly Asp His Tyr Gly Lys Lys Asn Thr Glu Glu Lys Ile Tyr Leu Pro
450             455             460

Pro Ile Pro Ala Asp Glu Ile Arg Asn Pro Val Val Leu Arg Ala Leu
465             470             475             480

Ser Gln Ala Arg Lys Val Ile Asn Gly Val Val Arg Arg Tyr Gly Ser
            485             490             495

Pro Ala Arg Ile His Ile Glu Thr Ala Arg Glu Val Gly Lys Ser Phe
            500             505             510

Lys Asp Arg Lys Glu Ile Glu Lys Arg Gln Glu Asn Arg Lys Asp
            515             520             525

Arg Glu Lys Ala Ala Lys Phe Arg Glu Tyr Phe Pro Asn Phe Val
            530             535             540

Gly Glu Pro Lys Ser Lys Asp Ile Leu Lys Leu Arg Leu Tyr Glu Gln
545             550             555             560

Gln His Gly Lys Cys Leu Tyr Ser Gly Lys Glu Ile Asn Leu Gly Arg
            565             570             575

Leu Asn Glu Lys Gly Tyr Val Glu Ile Asp His Ala Leu Pro Phe Ser
            580             585             590

Arg Thr Trp Asp Asp Ser Phe Asn Asn Lys Val Leu Val Leu Gly Ser
            595             600             605

Glu Asn Gln Asn Lys Gly Asn Gln Thr Pro Tyr Glu Tyr Phe Asn Gly
            610             615             620

Lys Asp Asn Ser Arg Glu Trp Gln Glu Phe Lys Ala Arg Val Glu Thr
625             630             635             640

Ser Arg Phe Pro Arg Ser Lys Lys Gln Arg Ile Leu Leu Gln Lys Phe
            645             650             655

Asp Glu Asp Gly Phe Lys Glu Arg Asn Leu Asn Asp Thr Arg Tyr Val
            660             665             670

Asn Arg Phe Leu Cys Gln Phe Val Ala Asp Arg Met Arg Leu Thr Gly
            675             680             685

Lys Gly Lys Lys Arg Val Phe Ala Ser Asn Gly Gln Ile Thr Asn Leu
            690             695             700

Leu Arg Gly Phe Trp Gly Leu Arg Lys Val Arg Ala Glu Asn Asp Arg
705             710             715             720

His His Ala Leu Asp Ala Val Val Val Ala Cys Ser Thr Val Ala Met
            725             730             735

Gln Gln Lys Ile Thr Arg Phe Val Arg Tyr Lys Glu Met Asn Ala Phe
            740             745             750

Asp Gly Lys Thr Ile Asp Lys Glu Thr Gly Glu Val Leu His Gln Lys
            755             760             765

Thr His Phe Pro Gln Pro Trp Glu Phe Phe Ala Gln Glu Val Met Ile
            770             775             780

Arg Val Phe Gly Lys Pro Asp Gly Lys Pro Glu Phe Glu Glu Ala Asp
785             790             795             800

Thr Leu Glu Lys Leu Arg Thr Leu Leu Ala Glu Lys Leu Ser Ser Arg
            805             810             815

Pro Glu Ala Val His Glu Tyr Val Thr Pro Leu Phe Val Ser Arg Ala
            820             825             830

Pro Asn Arg Lys Met Ser Gly Gln Gly His Met Glu Thr Val Lys Ser
            835             840             845
```

```
Ala Lys Arg Leu Asp Glu Gly Val Ser Val Leu Arg Val Pro Leu Thr
            850                 855                 860

Gln Leu Lys Leu Lys Asp Leu Glu Lys Met Val Asn Arg Glu Arg Glu
865                 870                 875                 880

Pro Lys Leu Tyr Glu Ala Leu Lys Ala Arg Leu Glu Ala His Lys Asp
                885                 890                 895

Asp Pro Ala Lys Ala Phe Ala Glu Pro Phe Tyr Lys Tyr Asp Lys Ala
            900                 905                 910

Gly Asn Arg Thr Gln Gln Val Lys Ala Val Arg Val Glu Gln Val Gln
            915                 920                 925

Lys Thr Gly Val Trp Val Arg Asn His Asn Gly Ile Ala Asp Asn Ala
    930                 935                 940

Thr Met Val Arg Val Asp Val Phe Glu Lys Gly Asp Lys Tyr Tyr Leu
945                 950                 955                 960

Val Pro Ile Tyr Ser Trp Gln Val Ala Lys Gly Ile Leu Pro Asp Arg
                965                 970                 975

Ala Val Val Gln Gly Lys Asp Glu Glu Asp Trp Gln Leu Ile Asp Asp
            980                 985                 990

Ser Phe Asn Phe Lys Phe Ser Leu His Pro Asn Asp Leu Val Glu Val
        995                 1000                1005

Ile Thr Lys Lys Ala Arg Met Phe Gly Tyr Phe Ala Ser Cys His
    1010                1015                1020

Arg Gly Thr Gly Asn Ile Asn Ile Arg Ile His Asp Leu Asp His
    1025                1030                1035

Lys Ile Gly Lys Asn Gly Ile Leu Glu Gly Ile Gly Val Lys Thr
    1040                1045                1050

Ala Leu Ser Phe Gln Lys Tyr Gln Ile Asp Glu Leu Gly Lys Glu
    1055                1060                1065

Ile Arg Pro Cys Arg Leu Lys Lys Arg Pro Pro Val Arg
    1070                1075                1080
```